US011974857B2

(12) United States Patent
LaChappelle et al.

(10) Patent No.: US 11,974,857 B2
(45) Date of Patent: May 7, 2024

(54) BIOMETRIC SENSOR ARRAY

(71) Applicant: Unlimited Tomorrow, Inc., Rhinebeck, NY (US)

(72) Inventors: Easton J. LaChappelle, Rhinebeck, NY (US); Alexandru Stefan Malcoci, Rhinebeck, NY (US); Kornelis Maarten Poort, Woodstock, NY (US)

(73) Assignee: Unlimited Tomorrow, Inc., Rhinebeck, NY (US)

( * ) Notice: Subject to any disclaimer, the term of this patent is extended or adjusted under 35 U.S.C. 154(b) by 759 days.

(21) Appl. No.: 17/064,713

(22) Filed: Oct. 7, 2020

(65) Prior Publication Data

US 2021/0100499 A1 Apr. 8, 2021

Related U.S. Application Data

(60) Provisional application No. 62/912,177, filed on Oct. 8, 2019.

(51) Int. Cl.
*A61B 5/00* (2006.01)
*A61F 2/70* (2006.01)
*A61F 2/80* (2006.01)
*A61B 90/00* (2016.01)
(Continued)

(52) U.S. Cl.
CPC .............. *A61B 5/4851* (2013.01); *A61F 2/70* (2013.01); *A61F 2/80* (2013.01); *A61B 2090/064* (2016.02); *A61B 2562/164* (2013.01); *A61B 2562/166* (2013.01); *A61F 2002/543* (2013.01); *A61F 2/72* (2013.01)

(58) Field of Classification Search
CPC ........................................................ A61F 2/54
See application file for complete search history.

(56) References Cited

U.S. PATENT DOCUMENTS 2,853,711 A 9/1958 Becker
4,426,884 A 1/1984 Polchaninoff
8,161,826 B1 4/2012 Taylor
(Continued)

FOREIGN PATENT DOCUMENTS

WO 2008030419 A2 3/2008
WO 2015060793 A1 4/2015

OTHER PUBLICATIONS

International Search Report including Written Opinion for PCT/US20/54534 dated Feb. 22, 2021; 13 pages.
(Continued)

*Primary Examiner* — Brian A Dukert
*Assistant Examiner* — Melissa A Hoban
(74) *Attorney, Agent, or Firm* — Lerner David LLP

(57) ABSTRACT

A biometric sensor array system may include a skin contact layer, a flexible printed circuit board ("PCB"), and a plurality of force sensing resistors ("FSRs"). The flexible PCB may be positioned adjacent the skin contact layer and may have a connector tail. Each FSR may be positioned on the flexible PCB. The connector tail may be adapted to electrically connect the plurality of FSRs to a signal receiving component. The flexible PCB may be configured so that one or more of the plurality of FSRs may be trimmed away from the flexible PCB so that the connector tail is still adapted to electrically connect a remaining one or more of the plurality of FSRs to the signal receiving component.

11 Claims, 36 Drawing Sheets

(51) Int. Cl.
*A61F 2/54* (2006.01)
*A61F 2/72* (2006.01)

(56) References Cited

U.S. PATENT DOCUMENTS

| | | |
|---|---|---|
| 8,607,651 B2 | 12/2013 | Eventoff |
| D717,685 S | 11/2014 | Bailey et al. |
| 8,987,577 B2 | 3/2015 | Eventoff |
| D742,272 S | 11/2015 | Bailey et al. |
| 9,214,146 B2 | 12/2015 | Eventoff |
| 9,299,248 B2 | 3/2016 | Lake et al. |
| D756,359 S | 5/2016 | Bailey et al. |
| 9,361,870 B2 | 6/2016 | Eventoff |
| 9,367,139 B2 | 6/2016 | Ataee et al. |
| 9,372,535 B2 | 6/2016 | Bailey et al. |
| 9,389,694 B2 | 7/2016 | Ataee et al. |
| 9,408,316 B2 | 8/2016 | Bailey et al. |
| 9,477,079 B2 | 10/2016 | Bailey et al. |
| 9,483,123 B2 | 11/2016 | Aleem et al. |
| 9,589,554 B2 | 3/2017 | Eventoff |
| 9,599,525 B2 | 3/2017 | Eventoff |
| 9,600,030 B2 | 3/2017 | Bailey et al. |
| 9,766,449 B2 | 9/2017 | Bailey et al. |
| 9,788,789 B2 | 10/2017 | Bailey |
| 9,807,221 B2 | 10/2017 | Bailey et al. |
| 9,842,578 B2 | 12/2017 | Eventoff |
| 9,874,744 B2 | 1/2018 | Bailey et al. |
| 9,880,632 B2 | 1/2018 | Ataee et al. |
| 9,903,771 B2 | 2/2018 | Eventoff |
| 9,904,051 B2 | 2/2018 | Aleem et al. |
| 9,958,682 B1 | 5/2018 | Moore et al. |
| 9,989,764 B2 | 6/2018 | Alexander et al. |
| 10,012,829 B2 | 7/2018 | Bailey et al. |
| 10,031,338 B2 | 7/2018 | Alexander et al. |
| 10,042,422 B2 | 8/2018 | Morun et al. |
| 10,054,788 B2 | 8/2018 | Bailey et al. |
| 10,067,337 B2 | 9/2018 | Bailey et al. |
| 10,073,268 B2 | 9/2018 | Alexander et al. |
| 10,078,219 B2 | 9/2018 | Alexander et al. |
| 10,078,220 B2 | 9/2018 | Alexander et al. |
| 10,078,435 B2 | 9/2018 | Noel |
| 10,101,809 B2 | 10/2018 | Morun et al. |
| 10,114,222 B2 | 10/2018 | Alexander et al. |
| 10,126,815 B2 | 11/2018 | Vidal et al. |
| 10,133,075 B2 | 11/2018 | Bailey et al. |
| 10,139,633 B2 | 11/2018 | Alexander et al. |
| 10,181,311 B2 | 1/2019 | Eventoff |
| 10,352,788 B2 | 7/2019 | Eventoff et al. |
| 10,362,958 B2 | 7/2019 | Morun et al. |
| 10,409,371 B2 | 9/2019 | Kaifosh et al. |
| 10,429,928 B2 | 10/2019 | Morun et al. |
| 10,460,455 B2 | 10/2019 | Giurgica-Tiron et al. |
| 10,489,986 B2 | 11/2019 | Kaifosh et al. |
| 10,496,168 B2 | 12/2019 | Kaifosh et al. |
| 10,504,286 B2 | 12/2019 | Kaifosh et al. |
| 10,528,135 B2 | 1/2020 | Bailey et al. |
| 2005/0043822 A1 | 2/2005 | Didrick |
| 2006/0129248 A1 | 6/2006 | Stark |
| 2008/0200994 A1* | 8/2008 | Colgate .............. A61F 2/70 623/24 |
| 2010/0274364 A1* | 10/2010 | Pacanowsky .......... A61F 2/80 600/595 |
| 2011/0167992 A1* | 7/2011 | Eventoff .............. G10H 1/0558 84/723 |
| 2012/0038469 A1 | 2/2012 | Dehmoubed et al. |
| 2012/0150322 A1 | 6/2012 | Goldfarb et al. |
| 2013/0053984 A1 | 2/2013 | Hunter et al. |
| 2013/0167663 A1 | 7/2013 | Eventoff |
| 2014/0083207 A1 | 3/2014 | Eventoff |
| 2014/0198034 A1 | 7/2014 | Bailey et al. |
| 2014/0198035 A1 | 7/2014 | Bailey et al. |
| 2014/0240103 A1 | 8/2014 | Lake et al. |
| 2014/0240223 A1 | 8/2014 | Lake et al. |
| 2014/0249397 A1 | 9/2014 | Ake et al. |
| 2014/0277589 A1 | 9/2014 | Veatch |
| 2014/0283670 A1 | 9/2014 | Eventoff |
| 2014/0334083 A1 | 11/2014 | Bailey |
| 2015/0199947 A1 | 7/2015 | Eventoff |
| 2015/0323391 A1 | 11/2015 | McCulloch et al. |
| 2015/0351935 A1 | 12/2015 | Donati et al. |
| 2016/0078854 A1 | 3/2016 | Eventoff |
| 2016/0284330 A1 | 9/2016 | Eventoff |
| 2017/0049583 A1 | 2/2017 | Belter et al. |
| 2017/0153153 A1 | 6/2017 | Eventoff et al. |
| 2017/0178611 A1 | 6/2017 | Eventoff |
| 2017/0184462 A1 | 6/2017 | Eventoff |
| 2017/0266020 A1 | 9/2017 | Glasgow |
| 2017/0290685 A1* | 10/2017 | Montez .................... A61F 2/80 |
| 2018/0102120 A1 | 4/2018 | Eventoff |
| 2018/0323365 A1 | 11/2018 | Roche et al. |
| 2019/0104982 A1 | 4/2019 | Dunn et al. |
| 2019/0121305 A1 | 4/2019 | Kaifosh et al. |
| 2019/0121306 A1 | 4/2019 | Kaifosh et al. |
| 2019/0150777 A1 | 5/2019 | Guo et al. |
| 2019/0209345 A1 | 7/2019 | LaChappelle |
| 2019/0212817 A1 | 7/2019 | Kaifosh et al. |
| 2019/0223748 A1 | 7/2019 | Al-natsheh et al. |
| 2019/0227627 A1 | 7/2019 | Kaifosh et al. |
| 2019/0228330 A1 | 7/2019 | Kaifosh et al. |
| 2019/0228533 A1 | 7/2019 | Giurgica-Tiron et al. |
| 2019/0228579 A1 | 7/2019 | Kaifosh et al. |
| 2019/0228590 A1 | 7/2019 | Kaifosh et al. |
| 2019/0228591 A1 | 7/2019 | Giurgica-Tiron et al. |
| 2019/0348025 A1 | 11/2019 | Berenzweig et al. |
| 2019/0348026 A1 | 11/2019 | Berenzweig et al. |
| 2019/0348027 A1 | 11/2019 | Berenzweig et al. |
| 2019/0354182 A1 | 11/2019 | Kaifosh et al. |
| 2019/0365318 A1 | 12/2019 | Guo et al. |
| 2019/0384901 A1 | 12/2019 | Osborn et al. |
| 2020/0022606 A1 | 1/2020 | Barbre et al. |
| 2020/0034978 A1 | 1/2020 | Giurgica-Tiron et al. |
| 2020/0046265 A1 | 2/2020 | Kaifosh et al. |
| 2020/0069210 A1 | 3/2020 | Berenzweig et al. |
| 2020/0069211 A1 | 3/2020 | Berenzweig et al. |
| 2020/0073483 A1 | 3/2020 | Berenzweig et al. |
| 2020/0118334 A1 | 4/2020 | Kaifosh et al. |
| 2020/0118350 A1 | 4/2020 | Kaifosh et al. |
| 2020/0125172 A1 | 4/2020 | Kaifosh et al. |

OTHER PUBLICATIONS

International Search Report and Written Opinion for PCT/US19/12603, dated Apr. 9, 2019, 15 pages.

\* cited by examiner

BIOMETRIC SENSOR ARRAY

CROSS-REFERENCE TO RELATED APPLICATIONS

This application claims the benefit of the filing date of U.S. Provisional Patent Application No. 62/912,177, filed Oct. 8, 2019, the disclosure of which is hereby incorporated by reference herein.

BACKGROUND OF THE DISCLOSURE

The present disclosure is directed to biometric sensor arrays, particularly for use with prostheses, although the sensor arrays described herein may be useful in various devices and products outside of prostheses. However, the general description of the sensor arrays described herein is provided in the context of prostheses, although their use is not so limited.

Prosthetic arms have been available for use, for example by amputees, for many years. More recently, mechanical and robotic components have been introduced into prosthetic arms to provide a wide range of functionality to the prosthetic arm, for example, with individual finger joints with various mechanisms of control, including based on the user's muscle control.

Conventional upper extremity prosthetic devices can be expensive and can take a long time to produce, which may make them unsuitable or undesirable for many uses. Some advanced electric hands on the market use a linkage mechanism to move the fingers to grab objects and perform tasks. This generally means that the fingers have a predetermined motion path and are unable to conform to objects. These hands may cost between $10,000 and $30,000, not including the cost to create the socket which couples to the residual limb of the user. The socket creation may result in even more time and even more cost to the prosthesis. As a result, many child amputees do not use these existing market devices. The conventional socket system is generally created by hand and is manual labor intensive. This may include making a plaster negative mold of the user's residual limb, then casting a positive, and molding a thermal plastic around this positive. From there, the socket may be tested and the process repeated until the socket fits properly and is comfortable. Muscle sensors may be molded into the socket to sense specific muscles that are used to control the hand. These sensors may use surface electrodes to sense the electrical activity of the user's muscle. The result of all of this is a generic and heavy robotic-looking device. In order to provide a more natural appearance of the prosthesis, custom silicon gloves have been created to match the user's skin tone, but this can dramatically increase costs and the glove often wears and breaks down rapidly. Thus, there is much room for improvement in robotic upper extremity prosthetic devices. Such improvements may include biometric sensor arrays described herein, and it will be clear that these improvements may be particularly suited for prosthetic extremities, but may find use in various other devices outside of the realm of prostheses.

BRIEF SUMMARY

According to one aspect of the disclosure, a system may include a first layer of material having a first surface, a second surface opposite the first surface, a central base area, and a plurality of arms extending radially outward from the central base area. Each of the plurality of arms may be spaced apart from an adjacent one of the plurality of arms and may have at least one recess formed therein extending from the first surface to the second. A flexible printed circuit board ("PCB") may be positioned adjacent the first layer of material so that a first surface of the flexible PCB confronts the second surface of the first layer of material. The flexible PCB may have a central base area and a plurality of arms extending radially outward from the central base area of the flexible PCB. Each of the plurality of arms of the flexible PCB may be spaced apart from an adjacent one of the plurality of arms of the flexible PCB. A plurality of force sensing resistors ("FSRs") may each be positioned adjacent a corresponding one of the recesses. A contact member may be positioned at least partially within each of the recesses. Each contact member may have a first dome-shaped end that protrudes above the first surface of the first layer, and a second end that confronts a corresponding one of the FSRs. Each FSR may include a copper layer coupled to a carbon film layer via an adhesive layer. The adhesive layer may have an opening so that the carbon film layer can directly contact the copper layer.

The system may further include a second layer of material having a first surface, a second surface opposite the first surface, a central base area, and a plurality of arms extending radially outward from the central base area of the second layer of material. Each of the plurality of arms of the second layer may be spaced apart from an adjacent one of the plurality of arms of the second layer. The second surface of the second layer of material may confront the first surface of the first layer of material. The first surface of the second layer of material may be configured to contact skin of a user of the system, and the first layer of material may be an intermediate layer of material sandwiched between the second layer of material and the flexible PCB. The central base area of the first layer of material and the central base area of the flexible PCB may each include a central aperture extending entirely therethrough, the central apertures being configured to receive a fastener therethrough.

The first layer of material may be formed of a foam material. The contact members may be translucent or transparent. The contact members may be formed of silicone. The plurality of FSRs may be part of a sensor layer positioned between the flexible PCB and the first layer of material. The sensor layer may include a plurality of sensors. All of the plurality of sensors may be FSRs. The plurality of sensors may include the plurality of FSRs, and at least one other sensor type. The at least one other sensor type may be selected from the group consisting of temperature sensors, optical sensors, acoustic sensors, electromyography ("EMG") sensors, accelerometers, pressure sensors, and microphones.

The system may further include a prosthetic limb and a socket. The socket may have a first portion adapted to couple to the prosthetic limb, and a second portion adapted to receive an amputee's residual limb. The central base areas of the first layer and the flexible PCB may be adapted to be received within the second portion of the socket so that, when the residual limb is positioned within the second portion of the socket, the central base areas of the first layer and the flexible PCB are sandwiched between the socket and a terminal end of the residual limb. The arms of the first layer and the flexible PCB may be adapted to extend up the user's residual limb in a direction away from the terminal end of the residual limb when the residual limb is positioned within the second portion of the socket. The flexible PCB may include a connector member adapted to operatively connect the flexible PCB to a controllable element of the prosthetic limb. The flexible PCB may be adapted to cause flexion or extension of one or more prosthetic fingers of the prosthetic limb based upon input received from at least one of the FSRs.

According to a further aspect of the disclosure, a system may include a first layer of material having a central base area and a plurality of arms extending radially outward from the central base area, each of the plurality of arms being spaced apart from an adjacent one of the plurality of arms. The system may also include a flexible printed circuit board ("PCB") positioned adjacent the first layer of material so that a first surface of the flexible PCB confronts a surface of the first layer of material. The flexible PCB may have a central base area and a plurality of arms extending radially outward from the central base area of the flexible PCB, each of the plurality of arms of the flexible PCB being spaced apart from an adjacent one of the plurality of arms of the flexible PCB. A plurality of force sensing resistors ("FSRs") may each be positioned at least partially between the first layer of material and the flexible PCB. A plurality of contact members may be positioned at least partially between the first layer of material and the flexible PCB. Each contact member may have a first dome-shaped end, and a second end that confronts a corresponding one of the FSRs. The first layer of material may be overmolded onto the flexible PCB layer. The first layer of material may be silicone, such as clear silicone. The plurality of contact members may be retained in their position by the first layer of material. A stiffening layer may be positioned beneath the flexible PCB. The stiffening layer may include a plurality of individual stiffening elements. The individual stiffening elements may have a shape that corresponds to a shape of the FSRs. Rivets may extend from one or more of the individual stiffening elements.

According to a further aspect of the disclosure, a sensor array system may include a skin contact layer, a flexible printed circuit board ("PCB"), and a plurality of force sensing resistors ("FSRs"). The flexible PCB may be positioned adjacent the skin contact layer and may have a connector tail. Each FSR may be positioned on the flexible PCB. The connector tail may be adapted to electrically connect the plurality of FSRs to a signal receiving component. The flexible PCB may be configured so that one or more of the plurality of FSRs may be trimmed away from the flexible PCB so that the connector tail is still adapted to electrically connect a remaining one or more of the plurality of FSRs to the signal receiving component. The sensor array may include a plurality of indicia on at least one of the skin contact layer and the flexible PCB. The plurality of indicia may be indicative of pathways along which the flexible PCB may be cut to remove the one or more of the plurality of FSRs from the flexible PCB so that the connector tail is still adapted to electrically connect the remaining one or more of the plurality of FSRs to the signal receiving component. The skin contact layer may be formed with a generally rectangular shape. The skin contact layer may include a first skin contact layer on a first side of the flexible PCB, and a second skin contact layer on a second side of the flexible PCB, so that the flexible PCB is sandwiched between the first and second skin contact layers. The first and second skin contact layers may each be formed of biocompatible foam. The skin contact layer may be an overmold layer that is overmolded on the flexible PCB. The skin contact layer may include a plurality of slits extending inward from an outer edge thereof, so that a plurality of individual areas are formed between adjacent ones of the plurality of slits. Each individual area of the skin contact layer may correspond with a location of at least one of the plurality of FSRs. Each of the plurality of slits may align with a corresponding cutout in the flexible PCB. The flexible PCB may include a first arm and a second arm extending radially outwardly from a center base, the first arm including a first group of the plurality of FSRs, the second arm including a second group of the plurality of FSRs. The first arm and the second arm may be positioned about 180 degrees relative to each other. The sensor array may include a first group of indicia, each indicium of the first group including a line extending transverse the first arm between each adjacent pair of FSRs in the first group of the plurality of FSRs, each being line indicative of a pathway along which the flexible PCB may be cut to remove the one or more of the plurality of FSRs from the flexible PCB so that the connector tail is still adapted to electrically connect the remaining one or more of the plurality of FSRs to the signal receiving component. The connector tail may include a first connector tail adapted to electrically connect the first group of the plurality of FSRs to the signal receiving component, and a second connector tail adapted to electrically connect the second group of the plurality of FSRs to the signal receiving component. The center base may be configured so that the second arm may be trimmed away from the flexible PCB so that the first group of the plurality of FSRs on the first arm remain electrically connected to the first connector tail. The plurality of FSRs may be provided as shunt mode FSRs. A prosthetic device may include a socket for receiving a residual limb of a user, the socket having a plurality of panels configured to directly or indirectly contact the residual limb of the user; and a plurality of the sensor array systems described above, each of the plurality of sensor array systems described above being coupled to a surface of a corresponding on of the plurality of panels. The socket may include a distal linking portion configured to couple to a prosthetic limb. The distal linking portion may include a recess therein, the signal receiving component being positioned within the recess. The connector tail of each one of the plurality of sensor array systems described above may pass through an opening in the distal linking portion of the socket and connects to the signal receiving component positioned within the recess.

DETAILED DESCRIPTION

Figure 1A:
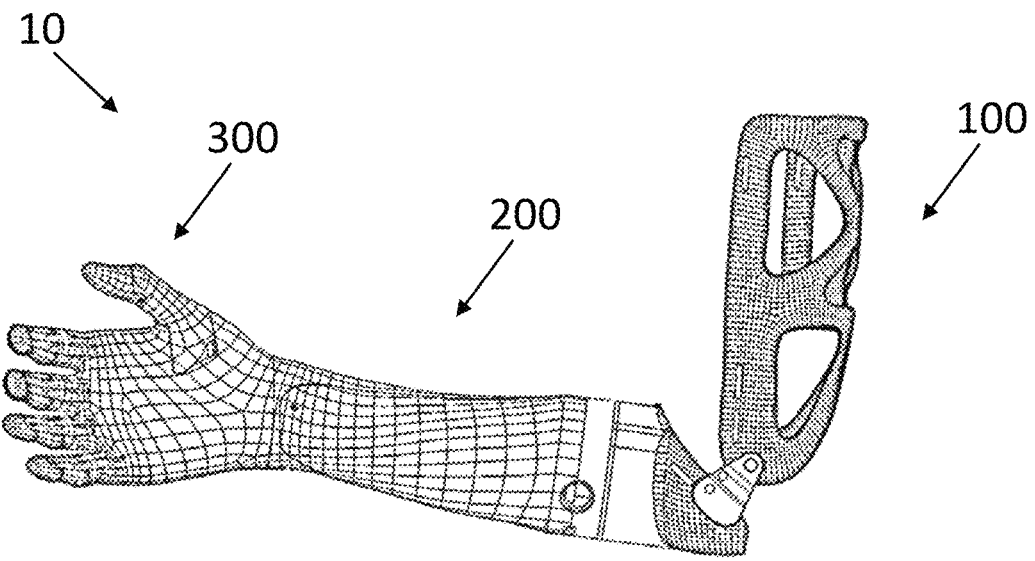
FIGS. 1A-C are views of a prosthetic upper extremity according to an aspect of the disclosure.
Figure 1B:
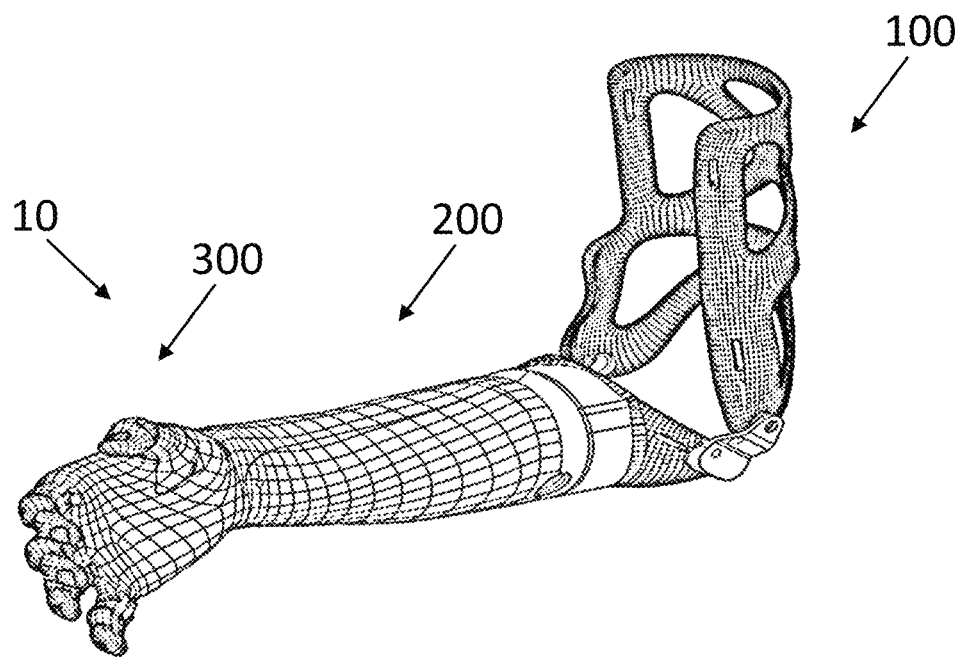
Figure 1C:
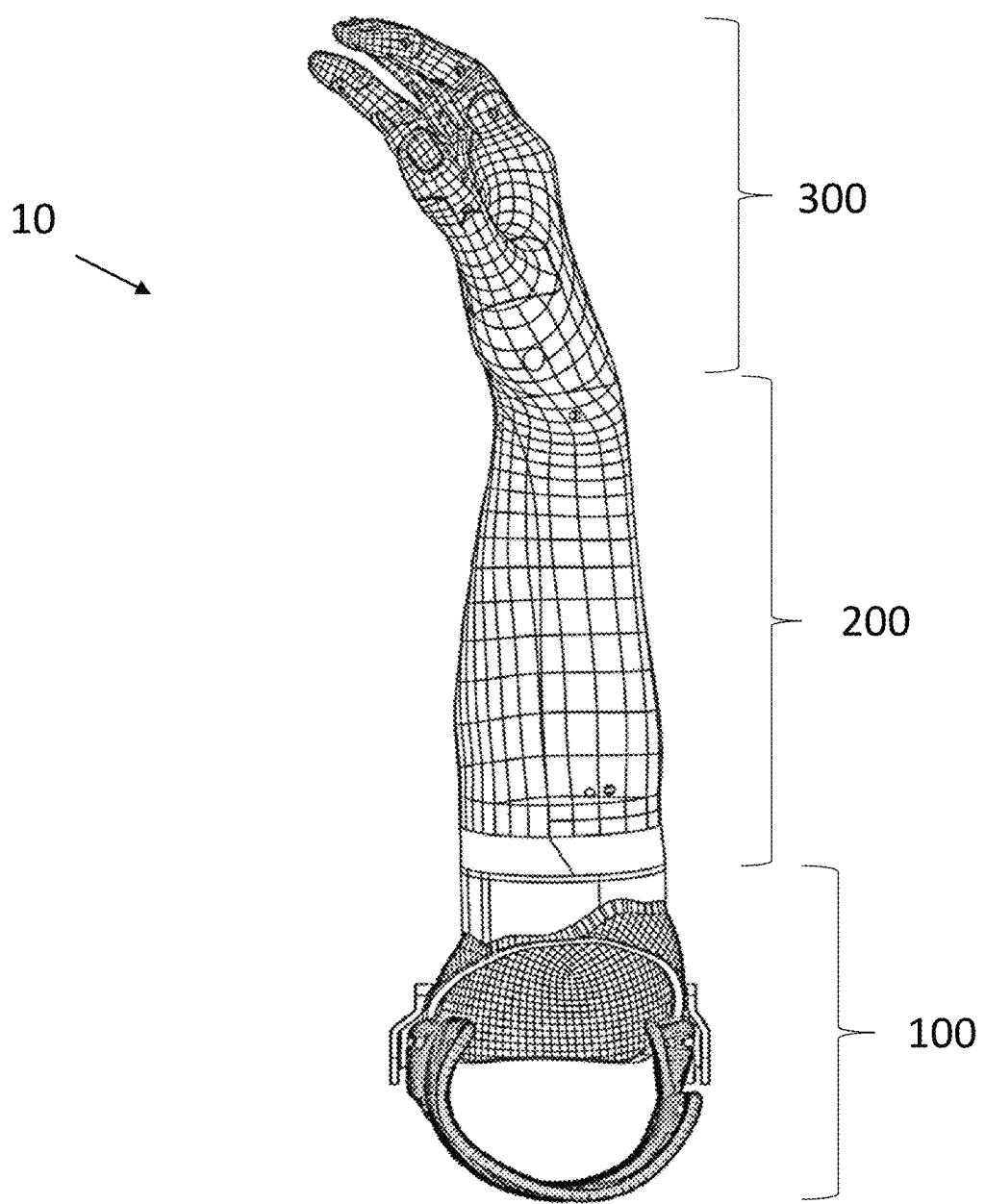

FIGS. 1A-C show an embodiment of a prosthetic upper extremity 10 for use in humans. Generally, prosthetic upper extremity 10 may include a socket 100, a prosthetic forearm 200, and a prosthetic hand 300. Prosthetic upper extremity 10, as well as related components and accessories thereof, are described in greater detail in U.S. Patent Application Publication No. 2019/0209345 and U.S. patent application Ser. No. 16/992,253, filed Aug. 13, 2020 and titled "Socket for Upper Extremity Prosthesis," the disclosures of which are hereby incorporated by reference herein.

Generally, the socket 100 of prosthetic upper arm extremity 10 is adapted for coupling to a user's residual limb to help secure the residual limb to the prosthetic upper arm extremity 10. Prosthetic upper arm extremity 10 may also include a prosthetic forearm 200 coupled, for example via a joint, to the socket 100, and a prosthetic hand 300 coupled to the prosthetic forearm 200. Various mechanical and electronic components can be housed within, or otherwise operably coupled to, any of the components of prosthetic upper arm extremity 10 to assist in allowing a user to control movements of the prosthesis, for example controlling flexion and extension of one or more fingers (or thumb) or groups of fingers of the prosthetic hand 300.

Figure 2A:
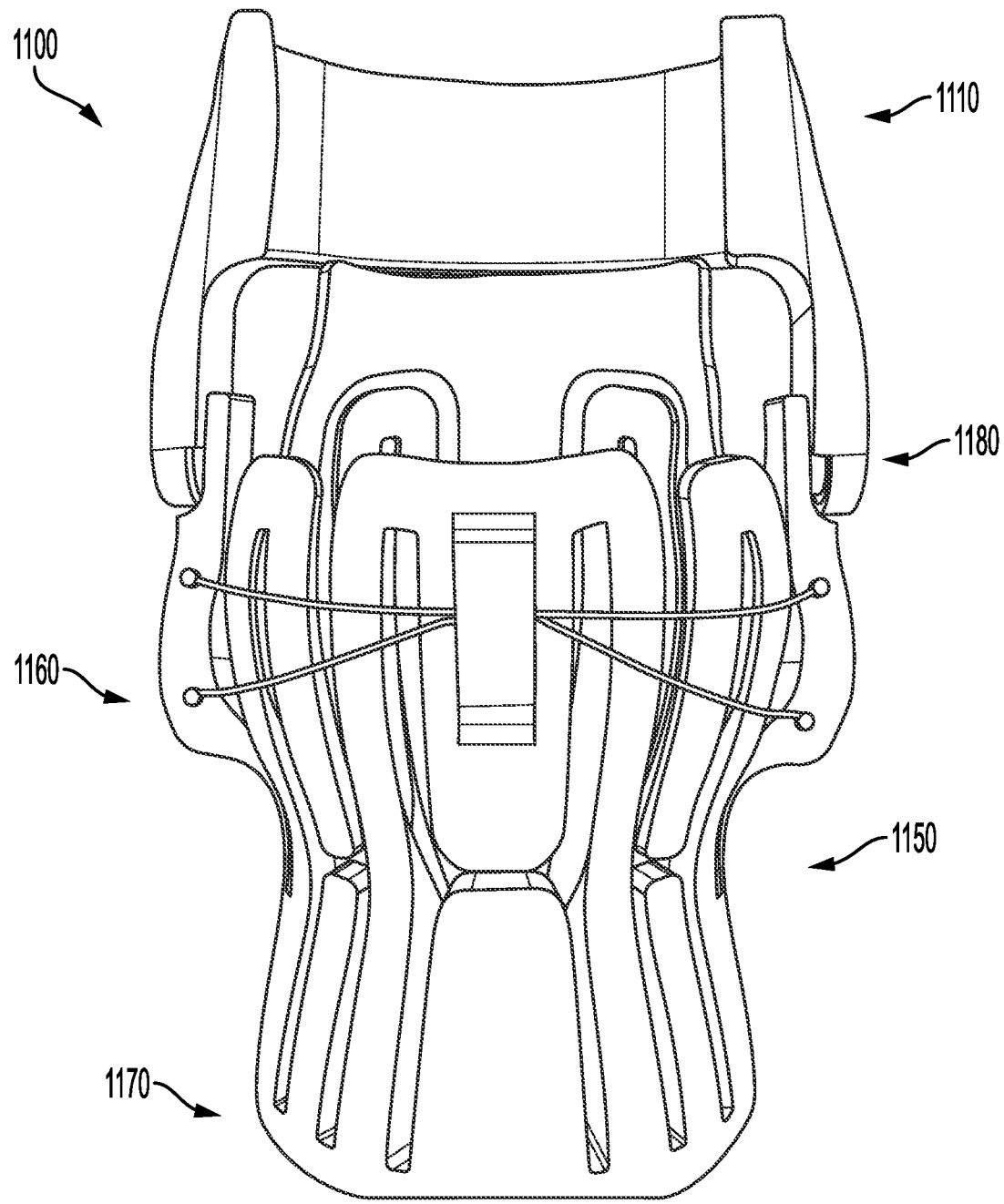
FIG. 2A is a perspective view of am assembled socket according to another aspect of the disclosure.

Although FIGS. 1A-C illustrate one type of socket 100, other types of sockets may be used to assist in coupling a prosthetic extremity to a user's residual limb. For example, FIG. 2A illustrates an alternate version of a socket 1100 that has been morphed, conformed, or otherwise modified from a generic model so that the portions of the socket 1100 in contact with the user's residual limb are specifically shaped and sized to correspond to the shape and size of the user's residual limb, and so that portions of the socket 1100 configured to couple to the remainder of the upper extremity prosthesis (e.g. a prosthetic forearm) are specifically sized and shaped to correspond to the size and shape of the remainder of the upper extremity prosthesis. Socket 1100 may include a proximal socket 1110 and a distal socket 1150, the proximal socket 1110 and distal socket 1150 being coupled by one or more joints 1180.

Proximal socket 1110 may be intended to fit over or otherwise couple to a user's upper arm. Proximal socket 1110 may also include extension members that each form part of a corresponding joint 1180. Proximal socket 1110 may include an interior surface adapted to directly or indirectly couple to the user's upper arm. The interior surface may be user-specific in the sense that it is shaped and contoured to match the shape of the portions of the user's upper arm that will contact the interior surface of the proximal socket 1110. A pre-determined offset may be introduced into proximal socket 1110. In other words, rather than produce proximal socket 1110 to include an interior surface that exactly matches the contours of the user's upper arm, the surface may be offset a fixed distance to allow for foam or other compressible or moldable material to be positioned as an interface between the user's upper arm and the interior surface of the proximal socket 1110. The thickness of the foam or other interference material may be equal or substantially equal to the amount of fixed distance offset.

Figure 2B:
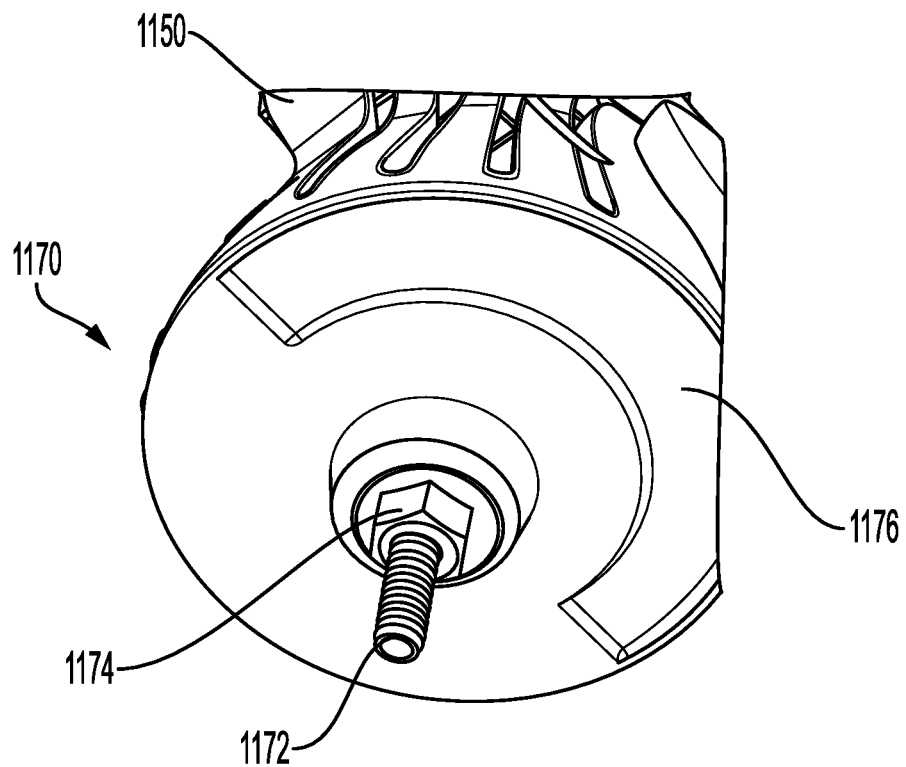
FIG. 2B is a bottom perspective view of the distal socket of FIG. 2A.

Referring to FIGS. 2A-B, distal socket 1150 is preferably (but not necessarily) formed of a single integral member. Distal socket 1150 may generally include a coupling portion 1160 for directly or indirectly attaching to the residual limb of a user (such as the distal-most end of the residual limb), and a linking portion 1170 for coupling to the remainder of the prosthetic upper extremity, such as prosthetic forearm 200. As with proximal socket 1110, the morphed or conformed geometry of coupling portion 1160 may be sized and shaped to receive the distal end of a particular user's limb therein, while linking portion 1170 may be sized and shaped to provide a smooth transition between the distal socket 1150 and the prosthesis coupled thereto. Also similar to proximal socket 1110, an offset may be introduced into the contact surface of the coupling portion 1160 in order to account for one or more additional interface layers, such as foam or another compressible or moldable material, which may be positioned between the user's residual limb and the interior surface of coupling portion 1160. Although not separately labeled, the coupling portion 1160 may include a lace or other tensioning system that may be tensioned while the user's residual limb is positioned within the coupling portion 1160 to further secure the socket 1100 to the user's residual limb.

Figure 2C:
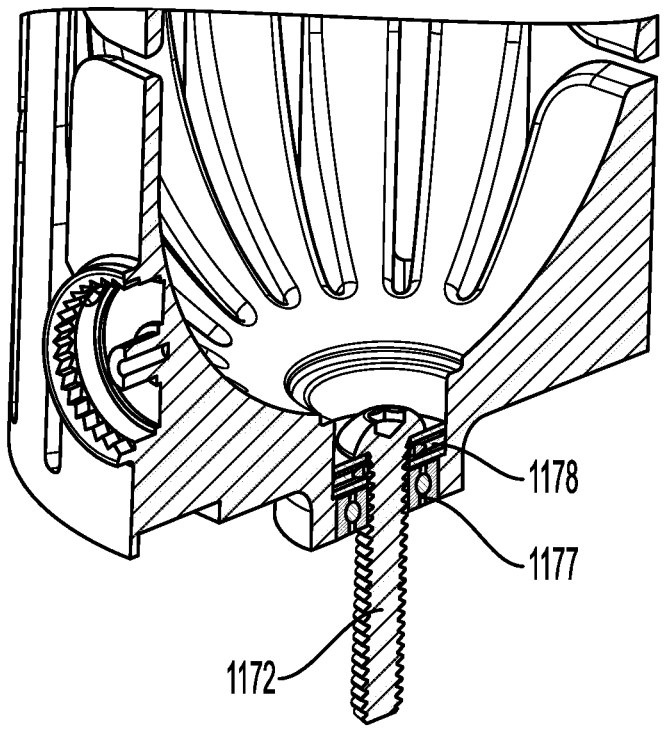
FIG. 2C is a cross-section of the distal socket illustrating a bolt and bearing accessories

Referring to FIG. 2B, a distal end of the linking portion 1170 of distal socket 1150 is illustrated. As noted above, linking portion 1170 may be configured to couple to a prosthetic upper extremity member, such as prosthetic forearm 200, or a similar component. The distal face of linking portion 1170 may include a central aperture for receiving a screw or bolt 1172 therethrough. Bolt 1172 may extend into a corresponding aperture in a prosthetic forearm, and a nut 1174 may be used to couple the prosthetic forearm to the linking portion 1170. Further, the distal face of linking portion 1170 may include a recess or track 1176, which in the illustrated embodiment is provided as a semi-circular or arcuate track extending about 180 degrees. The track 1176 may be adapted to receive a corresponding protrusion or other member of the prosthetic forearm. When the prosthetic forearm is assembled to the linking portion 1170, the prosthetic forearm may be manually rotated up to about 180 degrees, with the protrusion on the prosthetic forearm moving along the arc of track 1176. FIG. 2C illustrates a first bearing 1178 that may be used with bolt 1172. For example, in the illustrated embodiment, first bearing 1178 is a thrust bearing, for example a thrust needle roller bearing, which may be positioned within or on a lip of distal linking portion 1170. A second bearing 1177 may also be used with bolt 1172. For example, in the illustrated embodiment, second bearing 1177 is a radial bearing, for example a ball bearing. The radial bearing 1177 may allow for free axial rotation and resists lateral forces. The thrust bearing 1178 may allow for reliable reaction against axial forces while not disturbing axial rotation. Axial forces, in this case, may come both from prosthetic arm weight/movement/held objects and the tension of the screw or bolt 1172 tightened into the prosthetic arm to hold the assembly together. Although not illustrated in FIG. 2C, thrust bearing 1178 may be used with washers on either side of thrust bearing. In the illustrated embodiment, the radial bearing 1177 and thrust bearing 1178 are stacked on one another, with the thrust bearing 11788 being proximal to the radial bearing 1177, although other stacked configurations may be suitable. As best shown in FIG. 2C, the bearings 1178, 1177 may be positioned within a lip of the linking portion 1170.

Generally, when a user's residual limb is positioned within a socket, such as socket 100 or socket 1100, one or more sensors are attached to or otherwise in contact with the user's limb. For example, one or more sensors may be provided in or on distal socket 1150 to be in direct or indirect contact with the user's residual limb in order to assist the user in providing input for controlling the prosthetic extremity, such as prosthetic hand 300 (including, for example, flexion and extension of individual prosthetic fingers, prosthetic thumb, or groups of prosthetic fingers). In one example, a force sensor may be used to sense the force of a muscle contraction by the user. When the user flexes the muscle, the muscle changes shape and can expand. The force sensor(s) may work when a force is exerted from the user's muscle onto the surface of the force sensor(s), the force being transmitted into layers of a conductive polymer that change resistance based on the amount of force applied. One or more force sensors may be anchored to an elastic band, for example on a surface of distal socket 1150 intended to contact the user's residual limb, the elastic band helping to provide consistent pressure of the force sensor to the user's skin. The reading of the force sensor(s) once the elastic band is in the desired position and the user's muscles are in a resting state may be used as a zero point within software to track changes. A small cylindrical shaped foam piece may also be used to concentrate the force from the user's muscle to the force sensing area of the force sensor. By using a smaller diameter piece of foam than the diameter of the sensing area, contact with the muscle is improved and smaller changes may be detected. When a muscle is flexed, the muscle pushes on this piece of foam that pushes on the force sensor. This may also provide proportional data of the amount of muscle activity. In other words, instead of being a binary on/off signal, this above-described sensor configuration may provide data regarding the intensity of the muscle flex, the duration of flexing, and any kind of ramping of the flexing. This data may be used, alone or in combination with other data, to provide information to a controller, such as a controller within (or operably coupled to) the prosthetic forearm 200 or the prosthetic hand 300, and in turn to accurately control one or more actuators to accurately flex or extend the prosthetic fingers and/or thumb of prosthetic hand 300. It should be understood that any sensors in socket 1100 may be coupled to electronics within (or operably coupled to) prosthetic forearm 200 or prosthetic hand 300, either wirelessly or in a wired fashion.

Another sensor that may be used in order to help a user control the flexion and extension of the prosthetic fingers and/or thumb is an electromyography ("EMG") sensor, which detects the electrical potential generated by muscle cells. In one example, the EMG sensor may include three surface electrodes, including positive, negative, and reference. The positive and negative electrodes may be placed on the desired muscle and the reference electrode may be placed somewhere without muscles, such as the elbow area. The EMG sensor may detect muscle activity and provide information to the electronics within (or operably coupled to) prosthetic forearm 200 or prosthetic hand 300 in order to control the actuation that controls the flexion and/or extension of the prosthetic fingers and/or prosthetic thumb.

In one embodiment, one or more force sensors may be used along with one or more EMG sensors. In one example, the electrodes of the EMG sensor may be placed on the force sensors so that when a user flexes the muscle, the electrodes make consistent contact and push into the force sensor. This may provide two different types of data to analyze and to translate into desired movement of the prosthetic hand 300.

In one embodiment, most or all of the electronics are coupled to or positioned within the interior of prosthetic forearm 200. One or more processors and/or controllers may be coupled to the various actuators that cause flexion and/or extension of individual ones or groups of prosthetic fingers (and/or a prosthetic thumb). The connection between the processor(s) and the actuators may be any suitable connection. Power may be provided to the device by any suitable method. For example, a rechargeable battery made from lithium-ion technologies may be provided within prosthetic forearm 200. Depending on the size of the user and the prosthetic upper extremity 10, at least a single cell battery may be used. The batteries may be recharged by using an external power source that is connected by a cable to a harness, such as a USB port, a magnetic connector, or other suitable modalities. The batteries can also be charged wirelessly by an inductive charging system including circuitry and transmitting and receiving coils. The receiving coil may be placed on the inside of the prosthetic forearm 200 with the main electronics, or in another position, such as within the prosthetic hand 300. The transmitting coil and circuitry may be in the form of a plate on which the prosthetic forearm 200 may rest. Magnets may be used for alignment to ensure the coils are in a desired alignment. These magnets may be imbedded into the charging plate and placed in the prosthetic forearm 200 below the outer surface so that magnets attract each other. However, in other embodiments, some or all of the electronics and/or power source(s) may be positioned within prosthetic hand 300.

Haptic feedback systems may be integrated into prosthetic extremity 10 to provide various types of information to the user, including device status, battery level, warnings, errors, selections, triggers, and/or force being encountered by prosthetic hand 300 during gripping. A small vibrating motor, similar to what is used in many cell phones, may be provided within prosthetic forearm 200 or another component of prosthetic device 10 to provide the haptic feedback to the user. In one example, the vibration motor is secured to a flat surface inside of the prosthetic forearm 200 so that the vibrations pass through the forearm 200, to the socket 100 (or 1100), and then to the skin of the user. Certain patterns and intensities of vibrations may be used to communicate different information to the user. For example, the device can calculate force that is being exerted on an object by the prosthetic hand 300, and the amount of force is communicated by a varying intensity of vibration, for example with a lower frequency corresponding to a relatively low amount of force and a high frequency corresponding to a relatively large amount of force. Other examples of haptic feedback may include a particular pattern of vibrations being provided when the prosthesis 10 is powered on to inform the user that the device 10 has adequate battery power and is ready to calibrate.

Force being exerted by prosthetic hand 300 on an object, for example during gripping, may be calculated for various uses, including to inform the user of the amount of force via haptic feedback. In one example, this force may be calculated by determining via the processor or other appropriate electronics the amount of current being drawn by the flexion and/or extension actuators and by determining the position of the actuator compared to time of the actuation. For example, when the prosthetic fingers and/or thumb meet an object during flexion, the speed of the flexion slows down to a stall, and the measured current draw of the motor can be correlated to the amount of force being exerted. Force can also be calculated by comparing the position of the actuator to the time from the start of movement. When the prosthetic fingers and/or thumb meet an object during flexion, they slow down the actuator for a small amount of time. By using a combination of both methods described above, an accurate force can be calculated to use for a force limit and to communicate the force being exerted through haptic feedback. Force limiting may be used to ensure the actuators stop before they exert too much force on the object, as well as to protect components in the prosthesis 10. An alternative or additional way to sense the force from the prosthetic fingers and/or thumb is to provide force sensors on the prosthetic fingers and/or thumb and/or the front of the palm of the prosthetic hand 300.

One additional benefit of the control systems and methods described above is the creation of a feedback loop, which can result when the user has proportional control of the movement of prosthetic hand 300, as well as feedback, such as visual or haptic feedback, regarding the force. For example, when the user starts to flex the muscle, the user can typically see a response of the prosthetic hand 300 starting to close. This creates a closed loop that allows the user to control the position of the prosthetic fingers and/or prosthetic thumb with more precision. When the prosthetic fingers and/or prosthetic thumb meet an object, the user may feel vibrations based on the amount of force from the prosthetic fingers and/or prosthetic thumb. The inclusion of both visual and haptic feedback regarding this force may provide even further precision in control of the prosthetic hand 300.

Once the components of prosthetic device 10 are finalized and printed (e.g. via 3D printing) or otherwise manufactured, they may be provided to the user. When the user receives prosthesis 10, the user may go through an initial calibration to ensure the sensors, such as the combined force/EMG sensors, are reading the user's muscle activity correctly. The muscle sensors, described above, may be mounted to the inside of the distal socket 1150 so that when the user puts the prosthesis on, the sensor is in a substantially consistent position relative to the residual limb and makes contact with the muscle. An application such as a smartphone app, a web app, and/or a desktop app may provide live data from the sensor(s) to the user, which may allow the user to place the sensor(s) on the muscle and to test the sensor(s) before mounting the prosthetic forearm 200 to the socket 100 (or 1100). Once the data meets the requirements the sensor(s) may be mounted, and the prosthesis 10 may be ready to use. Once the device is in position on the user and powered on, the user may be prompted on the mobile application to train a gesture profile. This process may display a gesture on the screen and record the raw data from the sensors that correspond to that gesture. Haptic feedback may be used to communicate to the user when the arm is powered on, when the data is recording for a grip, and/or when the recording has stopped. For example, the user may be prompted make a closed hand gesture for five seconds and the raw data may be recorded from the sensors for that time. The data resulting for all the hand grips may be loaded into a neural network that utilizes machine learning to look for patterns and to watch the raw data and trigger a particular grip in response to a recognized pattern. This process can be repeated many times to improve accuracy.

Additional electronics and/or software may be provided to enhance functionality. For example, onboard accelerometers, gyroscopes, and/or magnetometers may be used to measure the orientation and movement of the prosthesis. This monitoring may allow software to analyze this data and recognize patterns to trigger events or to conserve battery. For example, these components may be able to detect that the user is walking. In response, the prosthesis 10 may be put into a low power mode as it is unlikely that gripping motions will be used while walking. In another example, the monitoring may result in recognition that the walking is being performed during a particular event, such as carrying groceries, and the grip of the prosthetic hand 300 may be locked to help ensure the groceries remain firmly secure within the prosthetic hand 300. In another example, if the sensors detect a hand shake, the prosthetic hand 300 may close to make an intelligent selection based on movement. Recognizing these types of patterns throughout the day and week can help the prosthesis 10 become easier to use and to conserve battery. For example, if a certain grip is used more than others, the software can change the sensor input needed to trigger this grip making it easier to control.

The mobile application may also be used to configure the different grips and how those are triggered. For example, a user may be able to select a particular grip to be triggered by the muscle being held for one second and a different grip being triggered by a muscle burst, pulse, and/or contraction. This allows the user to customize the device to function in a desired way.

Typically, when including sensors with a prosthetic extremity 10, particularly muscle sensors, individual sensors are placed in the socket fitting, such as a socket similar to socket 100 (or socket 1100). However, the physiology of the residual limb is unique for every amputee. Thus, a thorough evaluation of the amputee is typically necessary to determine the location of the muscles in the residual limb that may be used with the sensors to control the prosthesis. Following that evaluation, sensors are strategically positioned on or within the socket to provide the desired contact with the user's residual limb at the desired locations.

Although the above-described sensor placement method may be both effective and sufficient for an individual user, the process may be both time consuming and expensive. Thus, it would be preferable to have a sensor system that could be used with a prosthetic device such as prosthesis 10 that does not require any (or significant) design specific to each amputee, but provides similar or better accuracy than the amputee-specific method of sensor placement. In other words, it would be preferable to have a "one-size-fits-all" or a "one-size-fits-most" sensor system that provides effective sensing of muscle activity while minimizing or eliminating the need for individual patient evaluation.

Figure 3A:
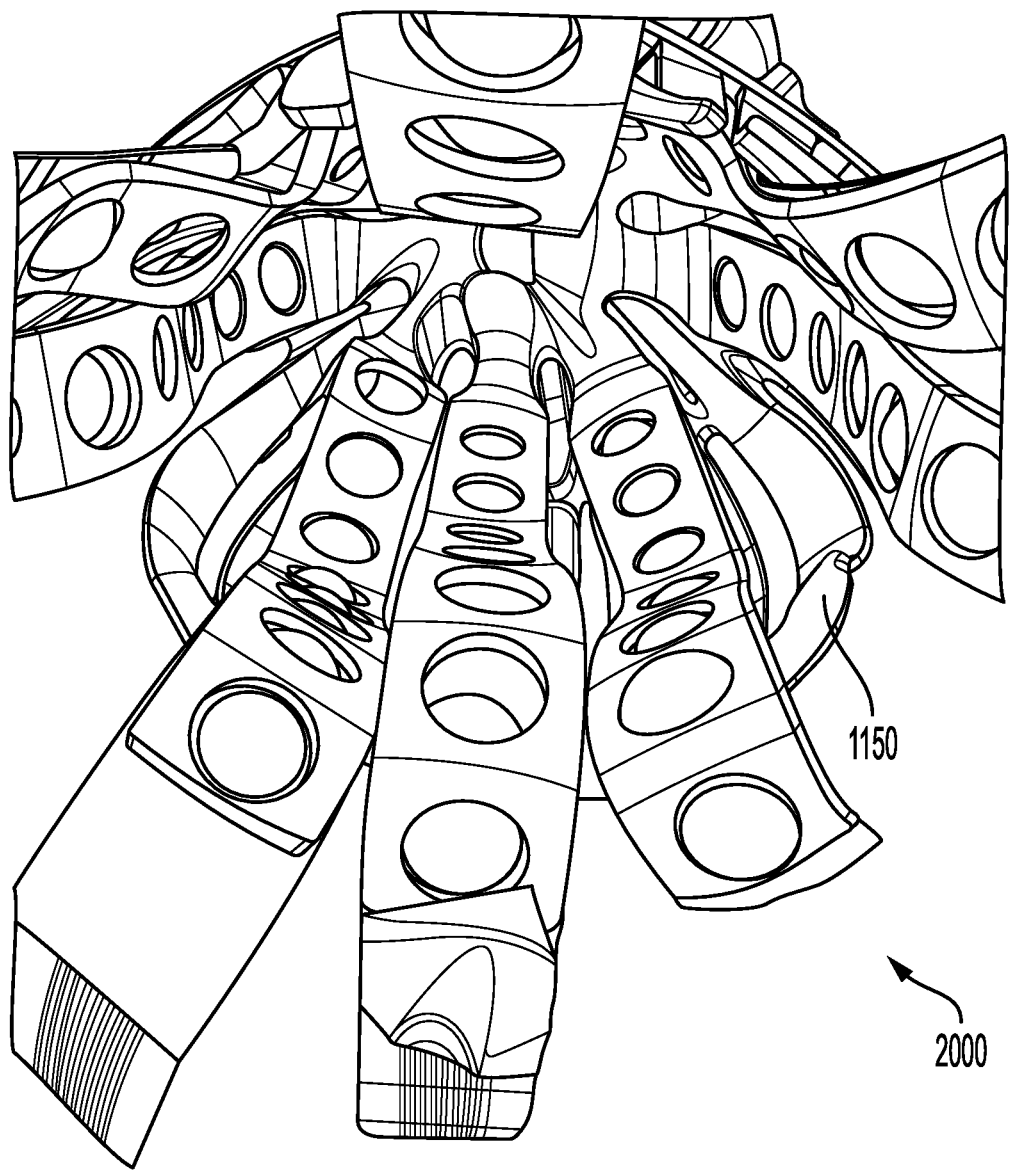
FIG. 3A is a perspective view of a biometric sensor array positioned within the socket of FIGS. 2A-C.

To this end, FIG. 3A illustrates a perspective view of a biometric sensor array 2000 assembled to distal socket 1150, although it should be understood that biometric sensor array 2000, with or without modifications, may be used with any prosthetic socket, or even in other contexts in which it is desired to provide sensors in contact with a user's limb, such as a residual limb. Although biometric sensor array 2000 is generally discussed below in the context of being used in a residual limb of a trans-radial amputee, it should be understood that the biometric sensor array 2000 could be used, with or without modification, on a residual limb of a trans-humeral amputee, a trans-tibial amputee, or a trans-femoral amputee. Still further, biometric sensor array 2000 may be used to obtain sensor input from parts of the body that are not involved with any amputation, such as a shoulder. As will be understood, biometric sensor array 2000 may be especially useful at obtaining sensor input data from a user on a portion of the body that has an amount of curvature or other irregular shape, such as a typical dome or hemispherical shape of a distal end of an amputated limb.

Figure 3B:
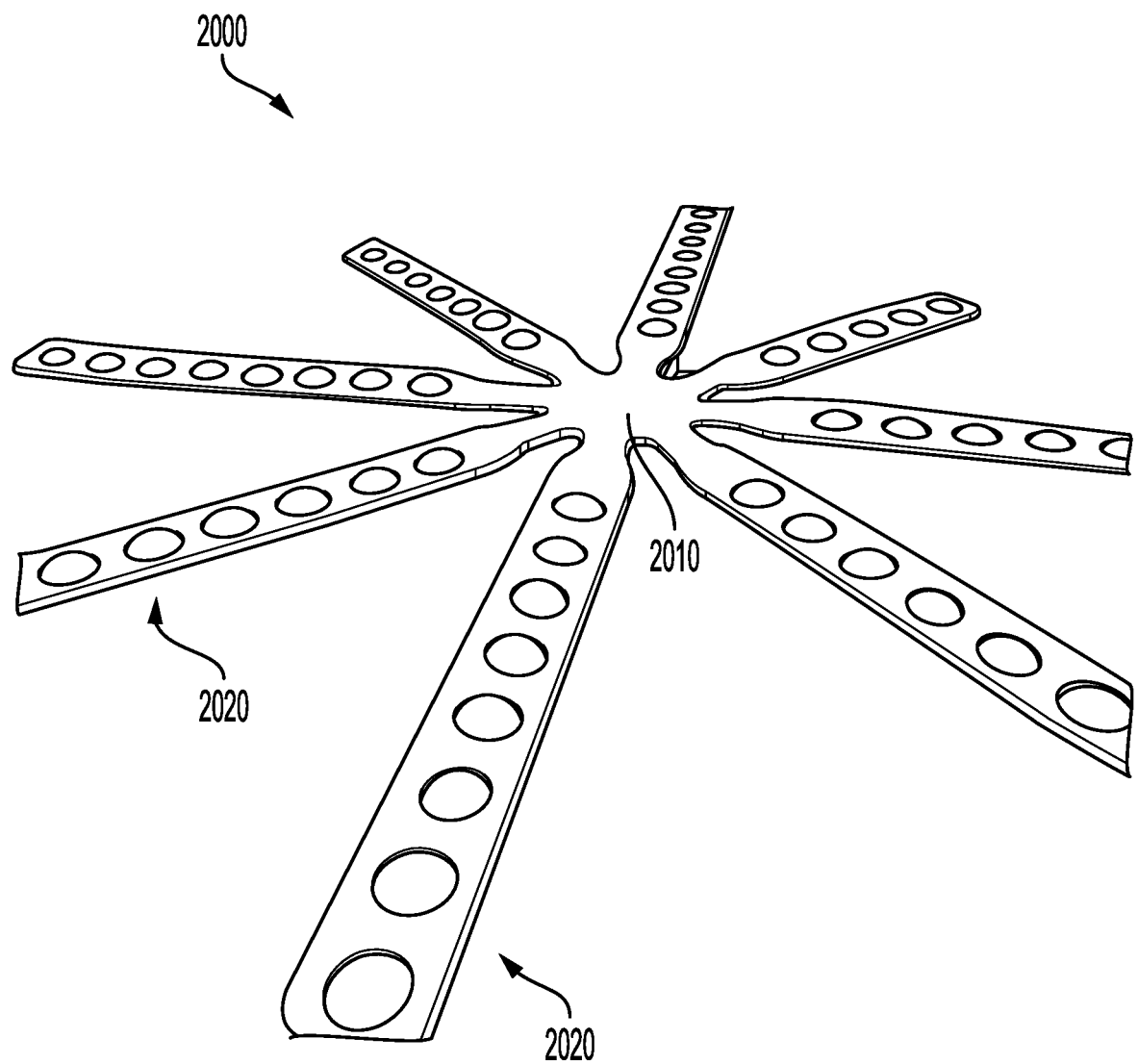
FIG. 3B is a perspective view of the biometric sensor array of FIG. 3A.

FIG. 3B is a perspective view of biometric sensor array 2000 in an assembled condition, although an optional central aperture, discussed in more detail below, is omitted from FIG. 3B. Generally, the biometric sensor array 2000 may include a central area 2010 and one or more arms 2020 radiating outwardly from the central area 2010. The specific components of biometric sensor array 2000 are described in greater detail below. In the particular illustrated embodiment, eight arms 2020 extend radially outwardly from the central area 2010, with each arm 2020 spaced evenly circumferentially from an adjacent arm 2020. In other words, in the illustrated embodiment, biometric sensor array 2000 includes four pairs of arms 2020 extending radially outwardly from the central area 2010, with each pair aligned at about 180 degrees. However, more or fewer arms 2020 may be provided, and the arms 2020 may be provided with any desired spacing. In other words, arms 2020 need not be provided in pairs, and need not be spaced at equal intervals from adjacent arms 2020. In some embodiments, a single arm 2020 may be provided, or otherwise two, three, four, five, six, seven, or more than eight arms 2020 may be provided extending outwardly from central area 2010. It should be understood that, in the view of FIG. 3B, the biometric sensor array 2000 is in a flat configuration, for example laid out on a table. However, as will become clear, the biometric sensor array 2000 may be easily contoured to fit and contact a user's anatomy.

Figure 3C:
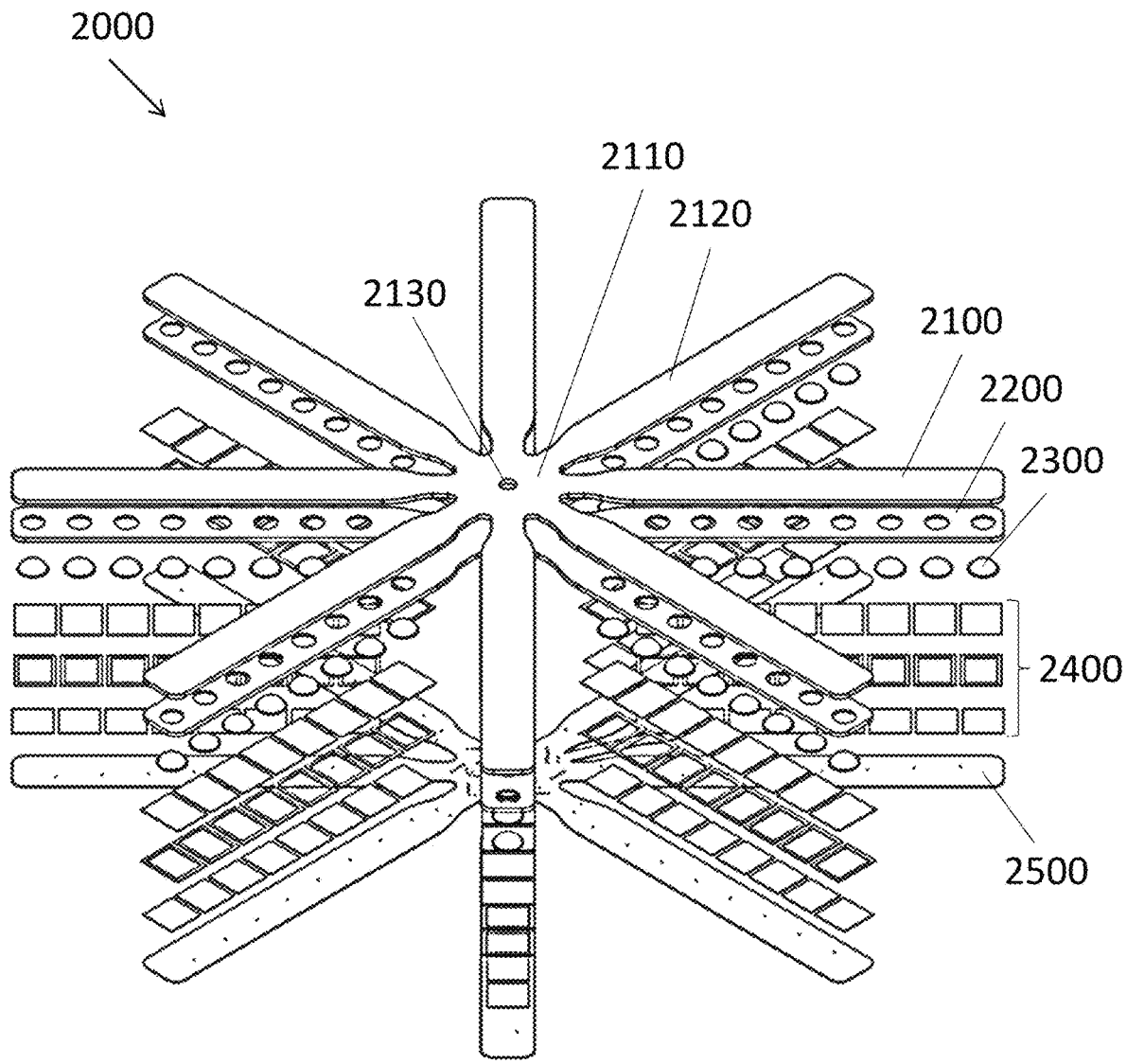
FIG. 3C is an exploded view of the biometric sensor array of FIG. 3A.
Figure 3D:
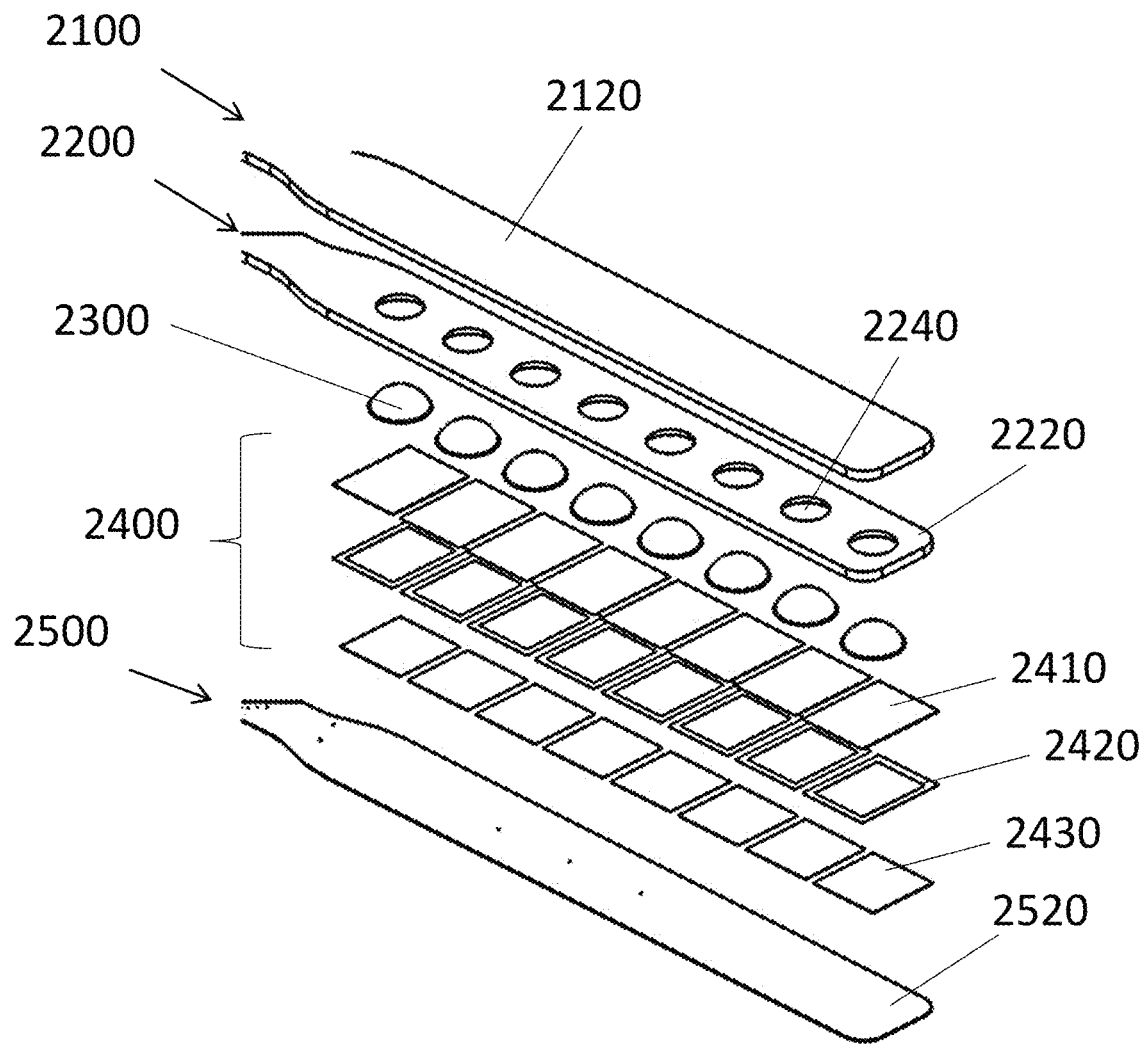
FIG. 3D is an exploded view of one of the arms of the biometric sensor array of FIG. 3A.

FIG. 3C is an exploded view of biometric sensor array 2000, and FIG. 3D is an exploded view of one of the arms 2020 of biometric sensor array 2000. Referring to FIG. 3C, biometric sensor array 2000 may include a plurality of layers and/or functional components. Moving from the top to bottom in the view of FIG. 3C, biometric sensor array 2000 may include a skin contact layer 2100, an intermediate layer 2200, a plurality of contact members 2300, a sensor layer 2400, and a printed flex circuit board ("flex PCB") layer 2500. As will become clear from the following description, some of these layers may be omitted from biometric sensor array 2000, or otherwise replaced with other components, depending on the intended use of the biometric sensor array 2000. For example, skin contact layer 2100 is omitted from the biometric sensor array 2000 illustrated in FIGS. 3A-B.

Still referring to FIG. 3C, skin contact layer 2100 may have the same general shape described above for biometric sensor array 2000, for example including a central base area 2110 and one or more arms 2120 radiating outwardly therefrom, in a similar or identical manner described in connection with the overall shape of biometric sensor array 2000 described above. In the illustrated embodiment, skin contact layer 2100 includes a central aperture 2130 at about the radial center of the central base area 2110. Central aperture 2130 may allow for a fastener, such as bolt 1172, to help secure the biometric sensor array 2000 to the socket 1100. It should be understood that other layers may include a similar central aperture. Preferably, central base area 2110 and arms 2120 are formed as a single integral piece, although in some embodiments the central base area 2110 and/or one or more of the arms 2120 may be formed separately and coupled together by any suitable means. Central base area 2110, and particularly arms 2120, are preferably flexible so that the skin contact layer 2100 is conformable to the surfaces of a user's anatomy and/or to an accessory structure, such as distal socket 1150. In one example, central base area 2110 and arms 2120 are formed of a foam, including a biocompatible foam, such that the arms 2120 are relatively easily flexed and conformed while also providing an amount of comfort to the user. For example, if skin contact layer 2100 is formed of a foam, it may be formed of a biocompatible foam, which may be a closed cell foam. Any suitable thickness of material may be used that provides desired comfort and functionality to the user, including between about 0.0625 inches (about 1.6 mm) and about 0.25 inches (about 6.35 mm). However, thicknesses outside this range may be suitable in some situations, and the particular thickness may be chosen based, at least in part, on comfort requirements of a particular user. If skin contact layer 2100 is included in biometric sensor array 2000, it may generally function to present a smooth, comfortable, and biocompatible layer of contact with the user's skin. This may help provide increased comfort, particularly if any of the underlying layers (discussed in greater detail below) might otherwise irritate the user's skin upon direct contact with the skin. However, it should also be understood that skin contact layer 2100 may be omitted in certain embodiments. For example, if direct contact between any of the underlying layers of biometric sensor array 2000 (described in greater detail below) is desired or required, the skin contact layer 2100 should be completely or partially omitted to allow for such direct contact.

Intermediate layer 2200 may have the same or similar general structure as the skin contact layer 2100 described above. For example, intermediate layer 2200 may include a central base area (not visible in FIG. 3C) and one or more arms 2220 radiating outwardly therefrom. The central base area may include a central aperture (not visible in FIG. 3C) that aligns with central aperture 2130 and may allow for a fastener to pass therethrough. If skin contact layer 2100 is included, whatever general shape is taken by the skin contact layer 2100, it may be preferable that the intermediate layer 2200 take substantially the same shape. If skin contact layer 2100 is omitted, intermediate layer 2200 may be the topmost layer of biometric sensor array 2000, although some underlying components may still pass through and protrude above intermediate layer 2200. Intermediate layer 2200 may be made from any suitable flexible material, although the material is preferably biocompatible, particularly if skin contact layer 2100 is omitted. In one example, intermediate layer 2200 may be formed of the same or similar material as skin contact layer 2100, and may have a similar thickness to skin contact layer 2100.

As is described in greater detail below, one or more electronic sensing components may be positioned adjacent, layered, or otherwise in contact with portions of intermediate layer 2200. Thus, it is preferable that the material forming the intermediate layer 2200 is able to transmit forces therethrough in order to transmit, for example, force from a user's muscle through the intermediate layer 2200 and to the adjacent sensor(s). However, in other embodiments, including the illustrated embodiment, the intermediate layer 2220 may include a plurality of cut-outs or recesses 2240 to receive therein and/or therethrough additional components, described in greater detail below. In one example, the central base area of intermediate layer 2200 is devoid of any cut-outs or recesses (other than the central aperture), while each arm 2220 includes one or more of the recesses 2240. In the illustrated example, each arm 2220 of intermediate layer 2200 includes eight recesses 2240 that are substantially evenly spaced along each arm 2220. Although each recess 2240 is generally circular, the recesses 2240 may be shaped to complement the shape of the object to be positioned therein and/or therethrough. Although eight recesses 2240 are shown on each arm 2220, it should be understood that more or fewer recesses 2240 may be provided in each arm 2220, with any desired relative spacing, and it should be understood that each arm 2220 may include a different configuration and/or number of recesses 2240. However, in some embodiments it may be preferable for each arm 2220 to include a similar or identical configuration and number of recesses 2240.

If recesses 2240 are included in the intermediate layer 2200, the intermediate layer 2200 may include a plurality of contact members 2300 to be received therein. When the biometric sensor array 2000 is assembled, the contact members 2300 may protrude beyond the surface of the corresponding arms 2220 of intermediate layer 2200, and into contact with an underside of skin contact layer 2100, if present. For example, in the illustrated embodiment, the recesses 2240 are substantially circular, and the contact members 2300 are substantially dome-shaped, spherical, or hemispherical. In one embodiment, the contact members 2300 are generally hemispherical with the dome-shape of the hemisphere protruding above the surface of the intermediate layer 2200 and intended to contact (either directly if skin contact layer 2100 is omitted, or indirectly if skin contact layer 2100 is present) the user's skin, with the opposite flat side of the contact members 2300 adapted to contact electronic components positioned below the contact members 2300, described in greater detail below. In use, the dome-shaped surfaces of the contact members 2300 are adapted to abut the user's skin (either directly or indirectly through skin contact layer 2100) in order to help transmit forces from the user's skin to the underlying electronic components described in greater detail below. In other words, the contact members 2300 help effectively transmit forces. If the contact members 2300 were omitted, the relatively large surface area of contact between the user's skin and the intermediate layer 2200 (and/or the skin contact layer 2100) might lead to forces being dissipated. To that end, it may be desirable to form the contact members 2300 of a material that is relatively hard or rigid to assist in transmitting forces, but preferably not so hard as to be uncomfortable for the user. One example of a suitable material may be silicone. However, other materials may be suitable, including relatively stiff biocompatible foam, various rubbers, and hard plastics. In some embodiments, it may be preferable for the contact members 2300 to be transparent or translucent to allow for optical transmission therethrough, particularly if any optical sensors are provided with biometric sensor array 2000, as described in greater detail below.

The biometric sensor array 2000 may include a sensor layer 2400 beneath the contact members 2300, however it should be understood that the sensor layer 2400 need not be a single continuous layer, but rather may include a plurality of individual sensors or groups of sensors. In the illustrated embodiment of biometric sensor array 2000, each sensor in the sensor layer 2400 is a force sensing resistor ("FSR"). In one embodiment, each FSR may include three components. A top portion of each FSR may be a carbon film 2410 in direct contact with a corresponding contact member 2300. As illustrated, the carbon film 2410 may be provided in a substantially square or rectangular shape. An adhesive film 2420 may be provided beneath the carbon film 2410. In the illustrated embodiment, the adhesive film 2420 may also be generally square or rectangular, and include a central cutout or recess so that direct contact may be made between the carbon film 2410 and the underlying copper layer 2430. The underlying copper layer 2430 may have a similar shape or the same shape as the carbon film 2410, and may be built into the flex PCB layer 2500. It should be understood that, although the FSRs in the illustrated embodiment have a specific structural framework, FSRs having other structural frameworks but similar functionality may be suitable for use in biometric sensor array 2000. The function of the FSRs of the sensor layer 2400 is described in greater detail below, following a brief description of the flex PCB layer 2500.

Figure 3E:
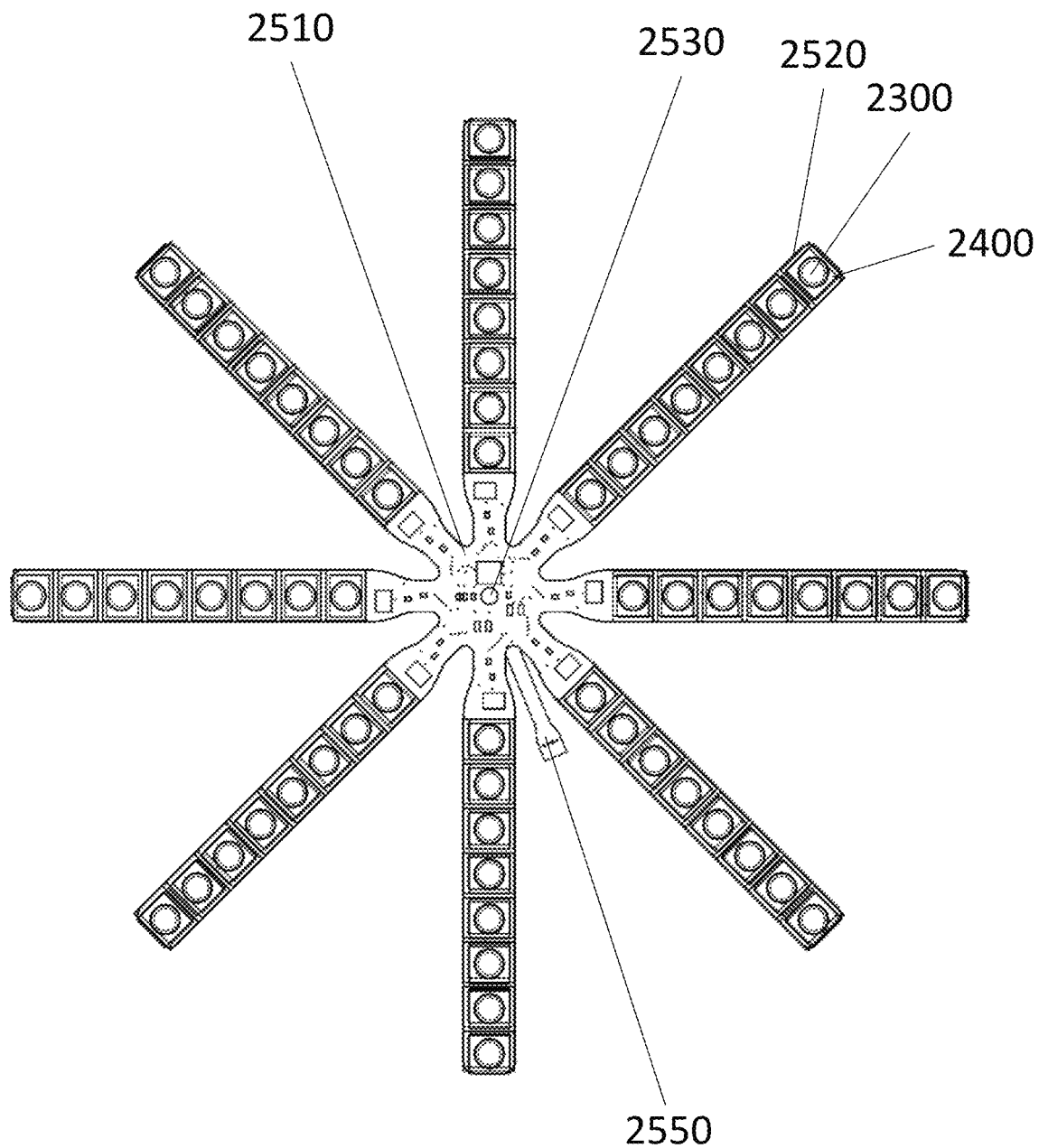
FIG. 3E is a top plan view of portions of the biometric sensor array of FIG. 3A, with certain components omitted for clarity of illustration.

The flex PCB layer 2500 may have a shape that substantially matches or otherwise complements the shapes of intermediate layer 2200, and skin contact 2100 (if present). For example, in the illustrated embodiment, flex PCB layer 2500 may include a central base area 2510 (shown in FIG. 3D), a plurality of arms 2520 radiating outwardly therefrom, and a central aperture 2530 (shown in FIG. 3D) that aligns with the other central apertures for receiving a fastener therethrough As noted above, the copper layer 2430 of sensor layer 2400 may be built into the flex PCB layer 2500, and the flex PCB layer 2500 may include additional electronics, for example for processing sensor input from the sensors on sensor layer 2400. As with the intermediate layer 2200 and the skin contact layer 2100, the flex PCB layer 2500 may be flexible and able to conform to a user's anatomy and/or a supporting structure, such as socket 1100. FIG. 3E provide a top plan view of PCB layer 2500, illustrating the sensor layer 2400 and the contact members 2300, but omitting the intermediate layer 2200 and the skin contact layer 2100 for clarity of illustration.

When the biometric sensor array 2000 is assembled, the PCB layer 2500 may be aligned with the intermediate layer 2200 and the skin contact layer 2100 so that the central base areas and the arms of these layers all align with each other. As can be seen best in FIG. 3E, although the individual sensors of sensor layer 2400 may be provided in any desirable number per arm 2520, the number and configuration of individual sensors on each arm 2520 preferably corresponds to the number and configuration of recesses 2240 and/or contact members 2300 on each corresponding arm 2220 of intermediate layer 2200. In the illustrated embodiment, each individual sensor of sensor layer 2400 is an FSR. In the assembled state of biometric sensor array 2000, each individual FSR may create a signal that corresponds to the amount of force applied on the FSR at any given time. In the illustrated example, because each FSR is in contact with a corresponding one of the contact members 2300, force placed on any particular contact member 2300 is transmitted to the corresponding FSR to create a signal that corresponds to the amount of force applied.

Referring still to FIG. 3E, the central base area 2510 of flex PCB layer 2500 may be adapted to receive a processor or a microcontroller, such as a microcontroller unit ("MCU"). Data from any sensors in sensor layer 2400, such as the FSRs, may be collected and organized into a digital signal value by the MCU, which data can be collected, organized, and/or distributed to any outside system (including components within or connected to the prosthetic arm 200 and/or prosthetic hand 300 to control movement thereof) via any suitable method, including common communication protocols. For example, relevant data and/or signals may be communicated from the flex PCB 2500 via I2C, serial, SPI, or other communication methods. The communication may be either wired or wireless, as desired. In the illustrated embodiment, flex PCB 2500 may include a connector member 2550, which may extend from the central base area 2510. The connector member 2550 may provide for a connection to wires or other transmission cables that ultimately connect to components being controlled by the biometric sensor array 2000. For example, the connector member 2250 (or wires connected thereto) may pass from the biometric sensor array 2000 through one or more components of the prosthetic upper extremity 10 to couple to components that control flexion and/or extension of the prosthetic fingers of prosthetic hand 300.

Although FIG. 3E illustrates the central base area 2510 of flex PCB layer 2500 as including electronics but not including any individual sensors, it should be understood that sensor layer 2400 may include sensors that are positioned within the central base area 2010 of biometric sensor array 2000. If sensors are positioned within central base area 2010, they may—but need not—be FSRs. In fact, if the biometric sensor array 2000 is intended for use with an amputee, it may be preferable that any sensors provided in the central base area 2010, which may be in contact with the terminal end of the residual limb, be non-FSR sensors.

As described above, biometric sensor array 2000 preferably has the ability to conform to shapes, such as a user's anatomy and/or a component of a prosthetic extremity such as a socket. Thus, flex PCB layer 2500 is also preferably flexible. In order to obtain the desired flexibility, the flex PCB layer 2500 may be formed with a low thickness, for example on the order of about 0.1 mm to about 0.3 mm of thickness. However, it may be preferable to include stiffening elements at strategic locations on the flex PCB layer 2500 to increase the durability of the flex PCB layer 2500 at those locations. Examples of such stiffening elements are described in greater detail below in connection with FIGS. 4A-B.

Although various modifications in numbers of arms 2020, numbers and types of sensors, etc. may be made, the illustrated embodiment of biometric sensor array 2000 includes a total of 64 FSR's and a corresponding 64 contact members 2300. In use, biometric sensor array 2000 may be placed inside a socket such as distal socket 1150, as best shown in FIG. 3A, with the central base area 2010 positioned substantially at the central dome-shaped receiving portion of the distal socket 1150. Because the entire biometric sensor array 2000 is flexible, each arm 2020 may extend proximally generally along the inner walls of the distal socket 1150, as also best shown in FIG. 3A.

Figure 3F:
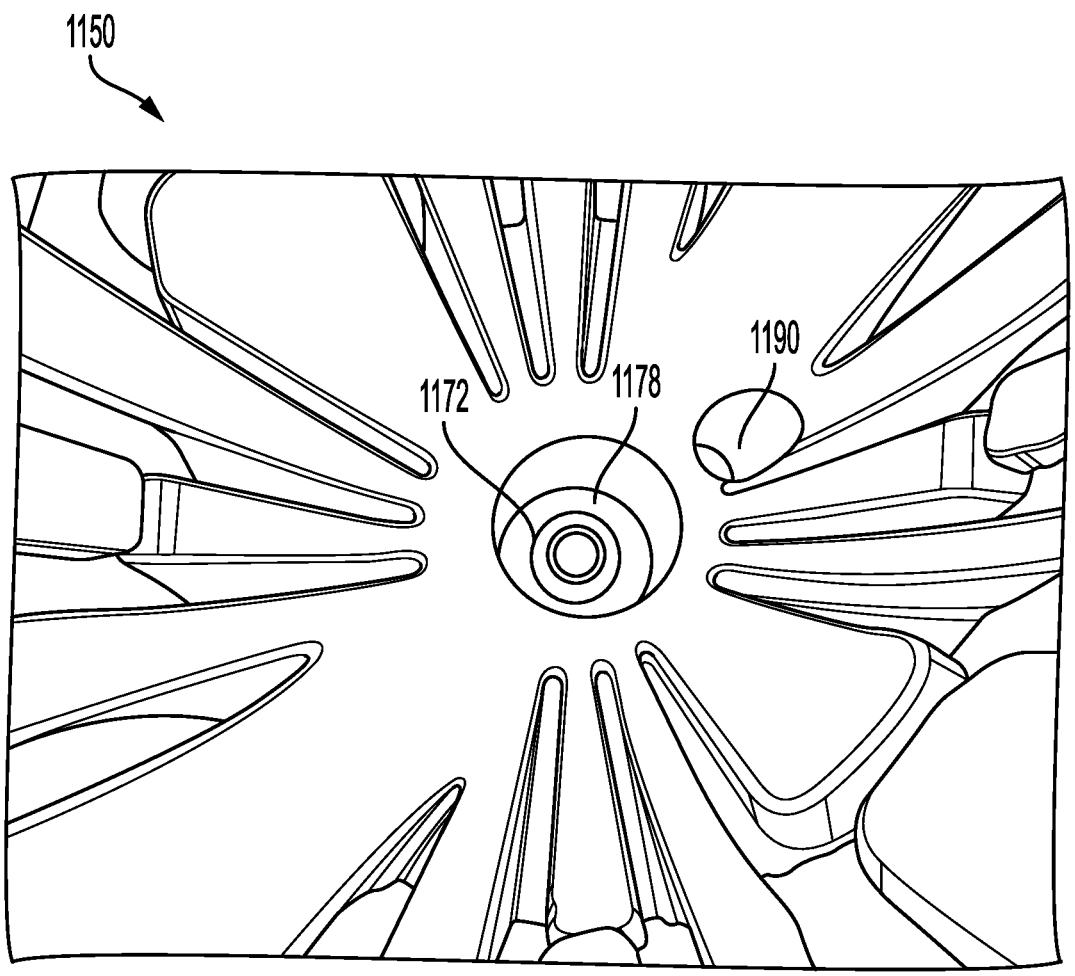
FIG. 3F is a perspective view of an interior portion of a distal end of the socket of FIG. 2A.
Figure 3G:
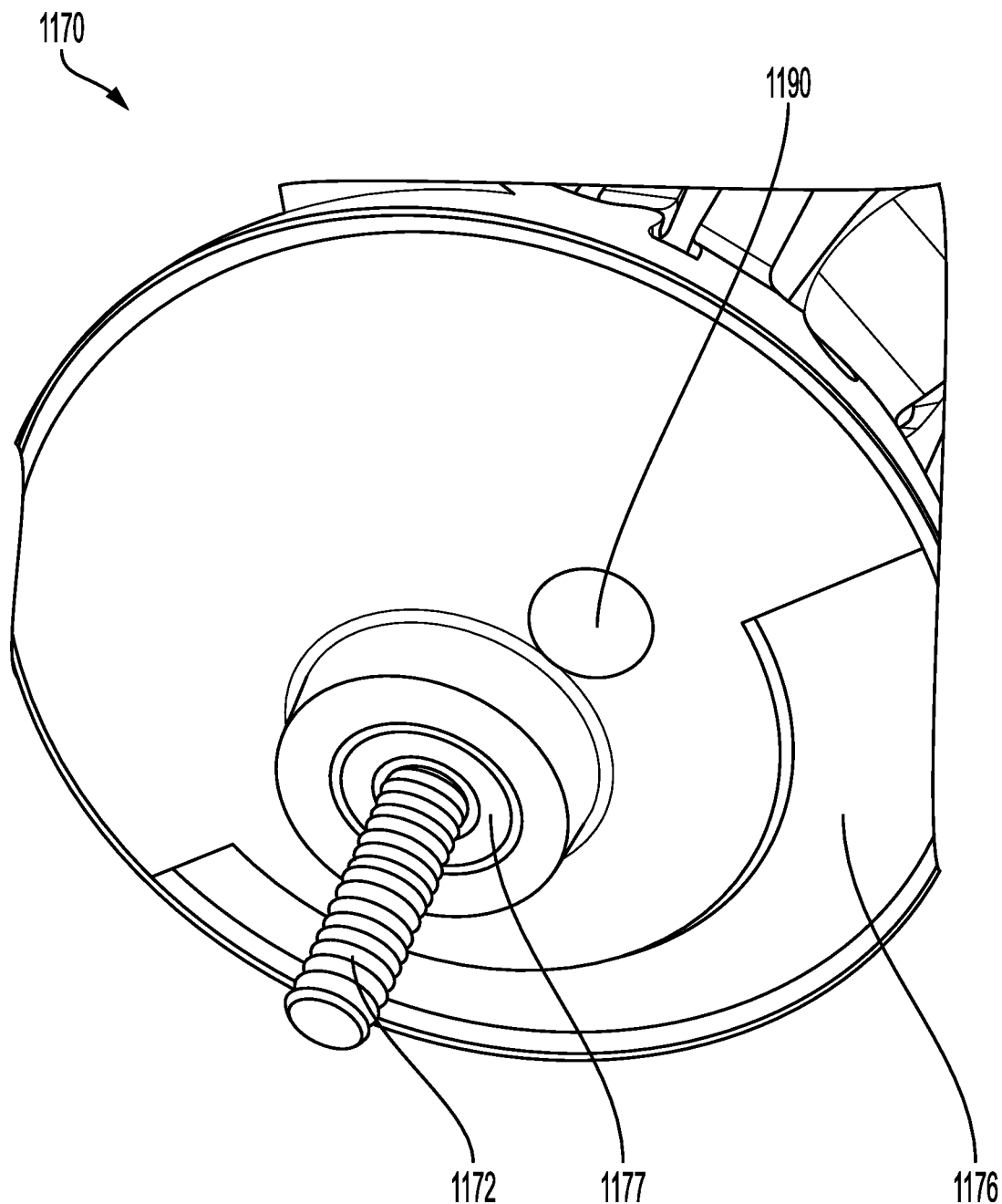
FIG. 3G is a perspective view of an exterior portion of the distal end of the socket of FIG. 2A.

Referring briefly to FIGS. 3F-G, interior and exterior views of the distal end of distal socket 1150 are illustrated, respectively. FIG. 3F illustrates the interior distal portion of distal socket 1150 which is intended to receive the central base areas of the various layers of the biometric sensor array 2000, as well as the residual limb of the user. As can be seen, the distal interior of distal socket 1150 is generally concave or dome-shaped or hemispherical-shaped. In addition to the thrust bearing 1178 and bolt 1172, FIG. 3F also illustrates an aperture 1190. The connector member 2250 (or wires coupled thereto) may pass through the aperture 1190, to allow for functional connection between the biometric sensor array 2000 and other components of the prosthetic extremity 10, such as a prosthetic forearm 200 and/or prosthetic hand 300. FIG. 3G illustrates the opposite surface of distal socket 1150, including the linking portion 1170, and the above-described track 1176, radial bearing 1177 and bolt 1172, in addition to the aperture 1190 that may receive wires (or the connector member 2250) that pass into the prosthetic forearm 200 (or into any prosthesis coupled to the socket).

As described above, one of the shortcomings of the typical use of FSRs in connection with muscle-controlled prosthetic devices is the time and effort to find the best location (or locations) of a FSR (or multiple FSRs) for the given user to ensure that the FSR(s) is in contact with a usable muscle that can be flexed or otherwise activated to cause to the FSR to create a signal for use in controlling the prosthesis. On the other hand, the biometric sensor array 2000 described herein may be placed within a socket of a prosthesis, such as distal socket 1150, and when the user places his or her residual limb into the distal socket 1150, the distalmost portion of the residual limb may contact (or be positioned adjacent) the central base 2010, with the arms 2020 extending like tentacles of an octopus (in the eight-arm embodiment) into contact with the user's residual limb. In other words, the biometric sensor array 2000 generally "cups" the distal end of the user's residual limb. Because of the number and positioning of the FSRs of sensor layer 2400, it is nearly guaranteed that at least one FSR will be in contact with a usable muscle for any given amputee, regardless of the level of amputation or the specific size and shape of the particular user's anatomy. Contact between a usable muscle and a single FSR may allow for the user to activate (e.g. flex or extend) the muscle in order to cause the FSR to generate a signal that allows for at least some level of control of the prosthesis, for example flexing or extending one or more prosthetic fingers and/or thumb of prosthetic hand 300. However, contact between usable muscles of the amputee and additional ones of the FSRs may provide even more robust control of any user-controllable elements of the prosthesis. Thus, as should be clear, the biometric sensor array 2000 described herein may be used for essentially any amputee with a very high likelihood of being able to sense the user's muscle actuation to control elements of a prosthesis operable coupled to the biometric sensor array 2000, completely eliminating the need to spend excessive time and cost on diagnosing a particular user to determine where the FSRs must be placed.

Although biometric sensor array 2000 is designed to fit nearly any residual limb of an amputee, in some embodiments, the design of the biometric sensor array 2000 may allow modifications to the dimensions without loss (or without significant loss) of function. For example, although biometric sensor array 2000 allows for adaptation to variations in size and form of the target object by its flexible nature, one or more of the individual arms 2020 can also be cut to a shorter size if desired, which may only affect the total number of sensors within sensor layer 2400 available, while allowing the assembly 2000 to continue functioning otherwise. For example, referring to FIG. 3E, a fully assembled biometric sensor array 2000 may be cut on any one or more arms 2020 between any pair of adjacent contact members 2300 (and thus between any pair of corresponding FSRs) to eliminate one or more FSRs, along with the corresponding lengths of the flex PCB layer 2500, the intermediate layer 2200, and the skin contact layer 2100, to reduce the size of the particular arm 2020, while one or more of the remaining FSRs will be able to provide the desired sensing functionality. In this regard, while biometric sensor array 2000 may be a "one-size-fits-all" or "one-size-fits-most" system, it may still be customizable in a sense, without needing to be designed ab initio specifically for individual users. And if any portions of the arms 2020 are removed, it should be understood that different arms 2020 may be shortened by different amounts (or not at all) based on the user's desire, without rendering the biometric sensor array 2000 non-functional.

Although one particular embodiment of biometric sensor array 2000 is shown in the figures with the sensor layer 2400 being formed completely of FSRs, it should be understood that other types of sensors (even non-biometric sensors) may be used in addition to, or instead of, FSRs. For example, while the illustrated embodiment of biometric sensor array 2000 includes 64 FSRs, far fewer than 64 FSRs may be included while maintaining an expectation that fewer FSRs may still allow for muscle-based control of a prosthetic device, such as prosthetic forearm 200 and/or hand 300. Thus, some of the FSRs of the illustrated embodiment may be replaced with various other types sensors, including temperature sensors, light or optical sensors, acoustic sensors, EMGs, accelerometers, pressure sensors, microphones, or any other suitable sensor, including any sensors described herein. For example, light or other optical sensors, including laser based optical sensors, could be positioned within sensor layer 2400 and function at least partially by allowing light to pass between the optical sensor and the user's skin. With this type of sensor, the skin contacting layer 2100 may be omitted (or omitted at the location of such sensors) to allow for a direct "line of sight" between the sensor and the user's skin. The contact members 2300 could thus also be omitted for those optical sensors. However, if the contact members 2300 are translucent or transparent, the contact members 2300 may remain in place as light may pass through the contact member 2300. In fact, if contact members 2300 are dome shaped, the contact members 2300 may even serve as a type of lens to enhance the sensor functionality. For other sensors that might require direct skin contact, such as EMGs or temperature sensors, both the skin contacting layer 2100 and contact member 2300 associated with that sensor may be omitted so that direct contact between the sensor and the user's skin may occur. It should be understood that any combination of suitable sensors may be used in sensor layer 2400 without changing the overall structure and shape of the biometric sensor array 2000, rather changing only the functionality of the biometric sensor array 2000, which may include altering the layout of the flex PCB layer 2500 to provide for appropriate sensor functionality, data processing, etc. It should also be understood that if a particular sensor on sensor layer 2400 requires direct skin contact, additional apertures or recesses may be provided wherever necessary to achieve such contact. Thus, it should be understood that the overall general structure and shape of biometric sensor array 2000 may still provide significant benefits, even if some of the sensors within the array are sensors other than FSRs.

Although only certain components of biometric sensor array 2000 are described in detail herein, it should be understood that other known accessory components may be provided with biometric sensor array 2000. For example, additional layers of foams, sensing membranes, adhesives and/or conductive materials may be included wherever desired to provide additional desired function, comfort, and/or biocompatibility. Further, biometric sensor array 2000 may be provided with other types of sensors or even haptic technologies, such a rotational vibration motors, linear vibration motors, piezoelectric elements, pneumatic elements, hydraulic elements, or any other type of haptic element that may be used to communicate information back to the user. For example, as described in greater detail above, the amount of force with which an object is being gripped by the prosthetic hand 300 may be communicated back to the user via a particular pattern (or particular amplitude, frequency, etc.) of vibrations, helping the user better understand the interaction between the prosthesis and the environment with which the prosthesis is interacting. Such additional devices may be attached directly to the flex PCB layer 2500, to the intermediate layer 2200, or indirectly to any of the structure described above in any suitable fashion.

The particular embodiment of biometric sensor array 2000 illustrated in the figures is designed for a trans-radial amputee (i.e. an arm that has been amputated at the forearm, across the radial bone). However, any amputation of any limb, at any level, will typically result in a residual limb that has a distal-most end that has a general dome or convex shape. Thus, the overall layout of biometric sensor array is suitable for use on any (or nearly any) residual limb. In embodiments, the particular dimensions of the biometric sensor array 2000 may be altered for a different limb, but the system may otherwise function similarly or identically. For example, the illustrated biometric sensor array 2000 may be somewhat undersized for a trans-femoral amputee, but the same exact layout, with dimensions of the biometric sensor array increased or otherwise scaled up, would function similarly or identically for a trans-femoral amputee compared to the illustrated embodiment of the biometric sensor array 2000 that is sized for a trans-radial amputee.

And while biometric sensor array 2000 may be particularly useful for interfacing between an amputated limb of a user and a prosthetic limb, the uses are not so limited. In fact, biometric sensor array 2000 may be adapted as a human-machine interface in various contexts, whether or not involving an amputee. For example, biometric sensor array 2000 may be easily contoured to a user's wrist, forearm, upper arm, ankle, etc. to provide an interface between the user's relevant body part and any device suitable for control by the biometric sensor array 2000. In an example in which the biometric sensor array 2000 is used on the wrist, similar to a bracelet or wrist-band, the biometric sensor assembly 2000 may include, for example, only one or two pairs of arms 2020 to easily wrap around the user's wrist, with the biometric sensor array 2000 coupled to an electronic device that may provide information to the user such as pulse, temperature, or any other information output by the particular sensors in the sensor layer 2400. Thus, while the particular illustrated embodiment of biometric sensor array 2000 may have special suitability as a human-machine interface between and amputated limb and a corresponding prosthesis, the illustrated biometric sensor array 2000 may be modified to serve as a human-machine interface between any electronic device and any part of the human body.

Figure 4A:
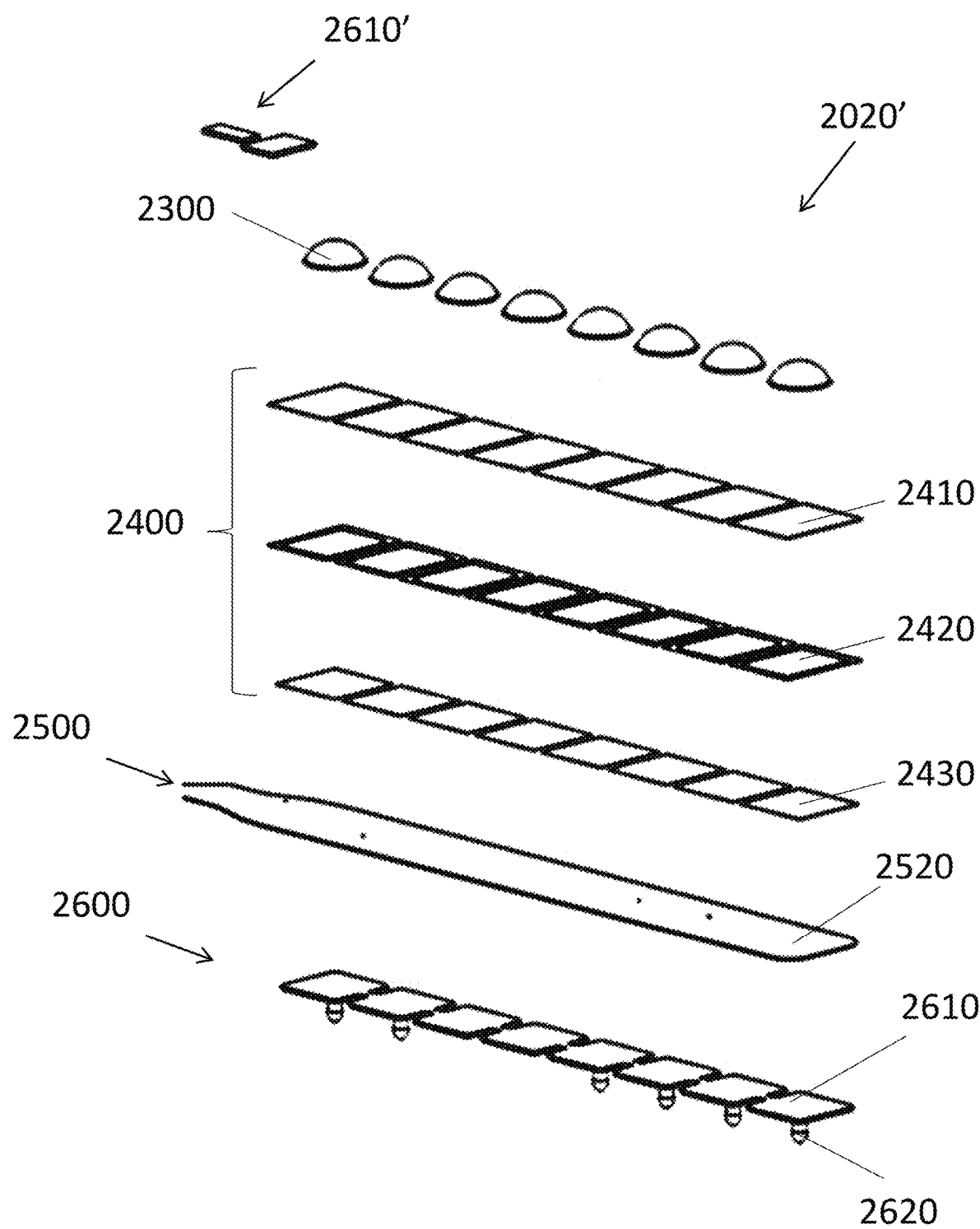
FIG. 4A is an exploded view of an alternate embodiment of an arm of a biometric sensor array.

FIG. 4A is an exploded view of an alternate embodiment of an arm 2020' of the biometric sensor array 2000 described above. It should be understood that similar or identical components are provided with the same part numbers as provided above with respect to arms 2020, and that the construction of the arm 2020' shown in FIG. 4A may be provided for some or all of the arms in a biometric sensor array. It should also be understood that the variations described above with respect to components of arm 2020 may apply with similar or equal force to the arm 2020' shown in FIG. 4A.

Generally, arm 2020' may include a plurality of contact members 2300 positioned adjacent to or in contact with corresponding components of the sensor layer 2400. The sensor layer 2400, in turn, may be positioned on the PCB layer 2500. These components may be similar or identical to the corresponding components described above. However, the arm 2020' of FIG. 4A illustrates at least two variations compared to the previously described arm(s) 2020.

Figure 4B:
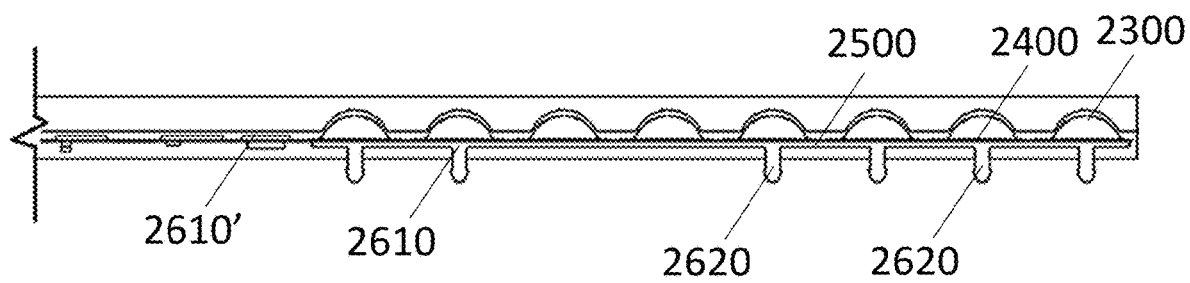
FIG. 4B is a side view of the arm of FIG. 4A.

First, arm 2020' is illustrated without a skin contact layer 2100 and without intermediate layer 2200. However, arm 2020' may include a functionally similar layer by overmolding a layer (or layers) over the components shown in FIG. 4A. For example, silicone, such as a clear silicone, may be overmolded onto the components shown in FIG. 4A to achieve a similar result of having a skin contact layer and/or intermediate layer. In other words, the overmolded material may result in a layer that may be comfortable and/or biocompatible, with the overmolded material also functioning to hold other components, such as contact members 2300, in their desired positions. This overmolding is schematically illustrated in FIG. 4B, with the overmolded silicone being positioned on top of and below the other components of the arm 2020', although rivets 2620, described in greater detail below, may protrude beyond the overmolded layer. Although silicone is one example of a suitable material for overmolding, other materials may be suitable. And it should be further noted that, even if the overmolding process is used, it may be desirable, in some situations, to still include one or more additional layers, such as foam layers, on top of the overmolded material to provide additional comfort for the end user.

Second, arm 2020' is illustrated with a plurality of stiffening elements 2610 in a stiffening layer 2600. As noted above, in some embodiments, it may be preferable to include stiffening elements at strategic locations on the flex PCB layer 2500 to increase the durability of the flex PCB layer 2500 at those locations. As shown in FIGS. 4A-4B, a plurality of stiffening elements 2610 are provided underneath the flex PCB layer 2500. In the illustrated embodiment, the stiffening elements 2610 have a shape that generally corresponds to the shape of the sensors of sensor layer 2400, with one stiffening element 2610 positioned on the flex PCB layer 2500 opposite a corresponding sensor. The stiffening elements 2610 may help ensure that, although the flex PCB layer 2500 maintains the ability to bend and conform, the bending occurs at locations that are least likely to cause stress on the sensors. The stiffening elements 2610 (and and/or 2610') may be formed of any suitable material, including nylon, including 3D printed nylon. Although the stiffening elements 2610 may be provided as individual elements, the stiffening elements 2610 may instead be provided as a continuous structure, with relatively thin strips of material connecting each stiffening element 2610. Rivets 2620 may also extend from selected ones of the stiffening elements 2610. For example, if the biometric sensor array is intended for use with a socket of a prosthesis, the socket may be provided with apertures or other engaging mechanism with which the rivets 2620 may engage to better connect the biometric sensor array to the socket. Although the stiffening layer 2600 is described and shown in connection with arm 2020', it should be understood that a similar or identical feature may be provided with arm 2020.

Stiffening elements of other types and forms than that shown and described in connection with stiffening elements 2610 may be suitable for use. For example, FIGS. 4A-B illustrate an alternative or additional stiffening element 2610' that may be positioned on the flex PCB layer 2500 near where an arm 2020 meets central area 2010. In this embodiment, stiffening element 2610' is provided on the top of the flex PCB layer 2500, although in other embodiments it may be provided on the bottom of the flex PCB layer. In addition, stiffening element 2610' does not correspond to an FSR of sensor layer 2400, but rather may be helpful in preventing bending of the PCB layer 2500 where other electrical components are coupled near the transition from the arm 2020 to central area 2010.

Figure 5A:
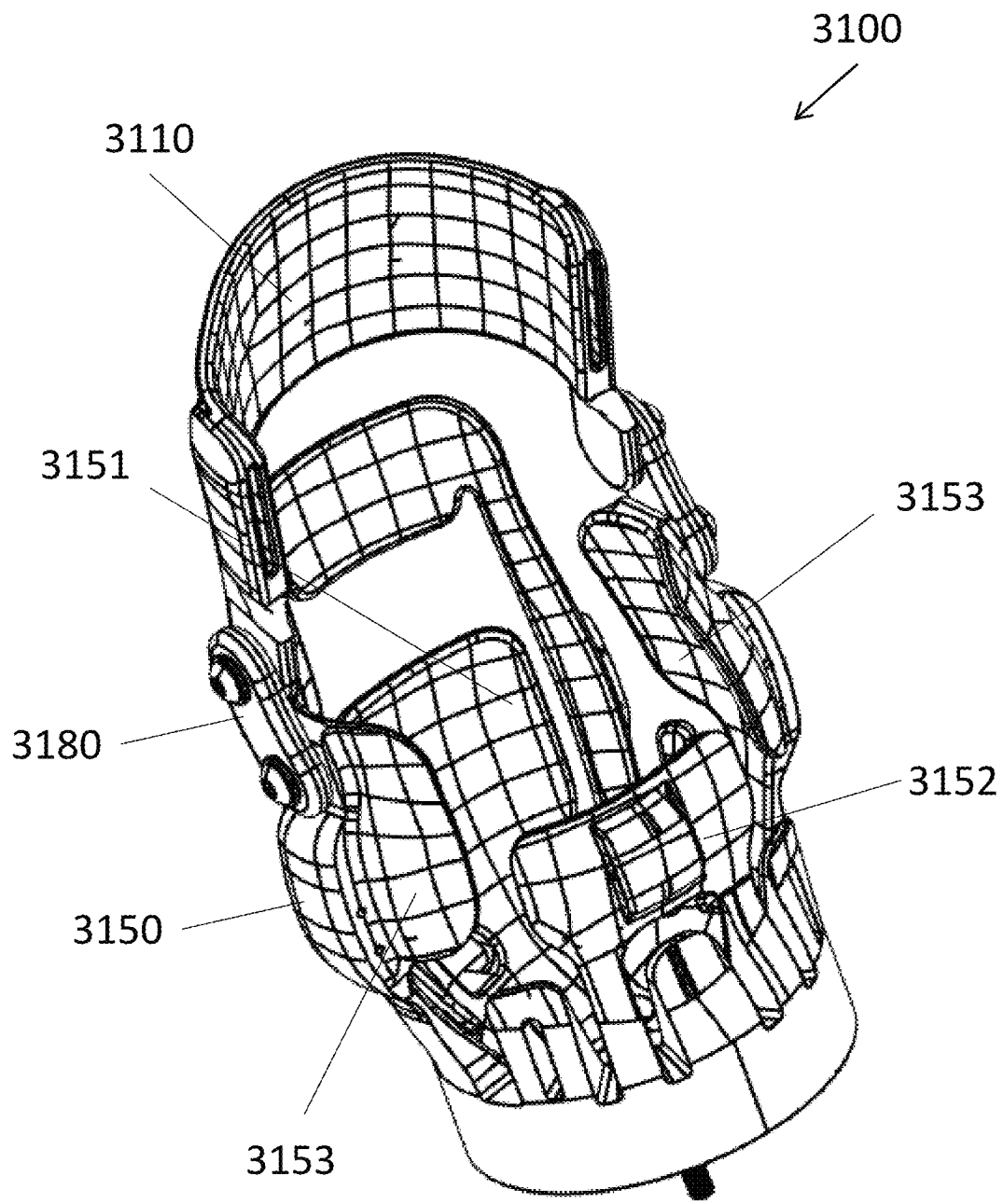
FIG. 5A is a perspective view of another embodiment of a socket according to the disclosure.
Figure 5B:
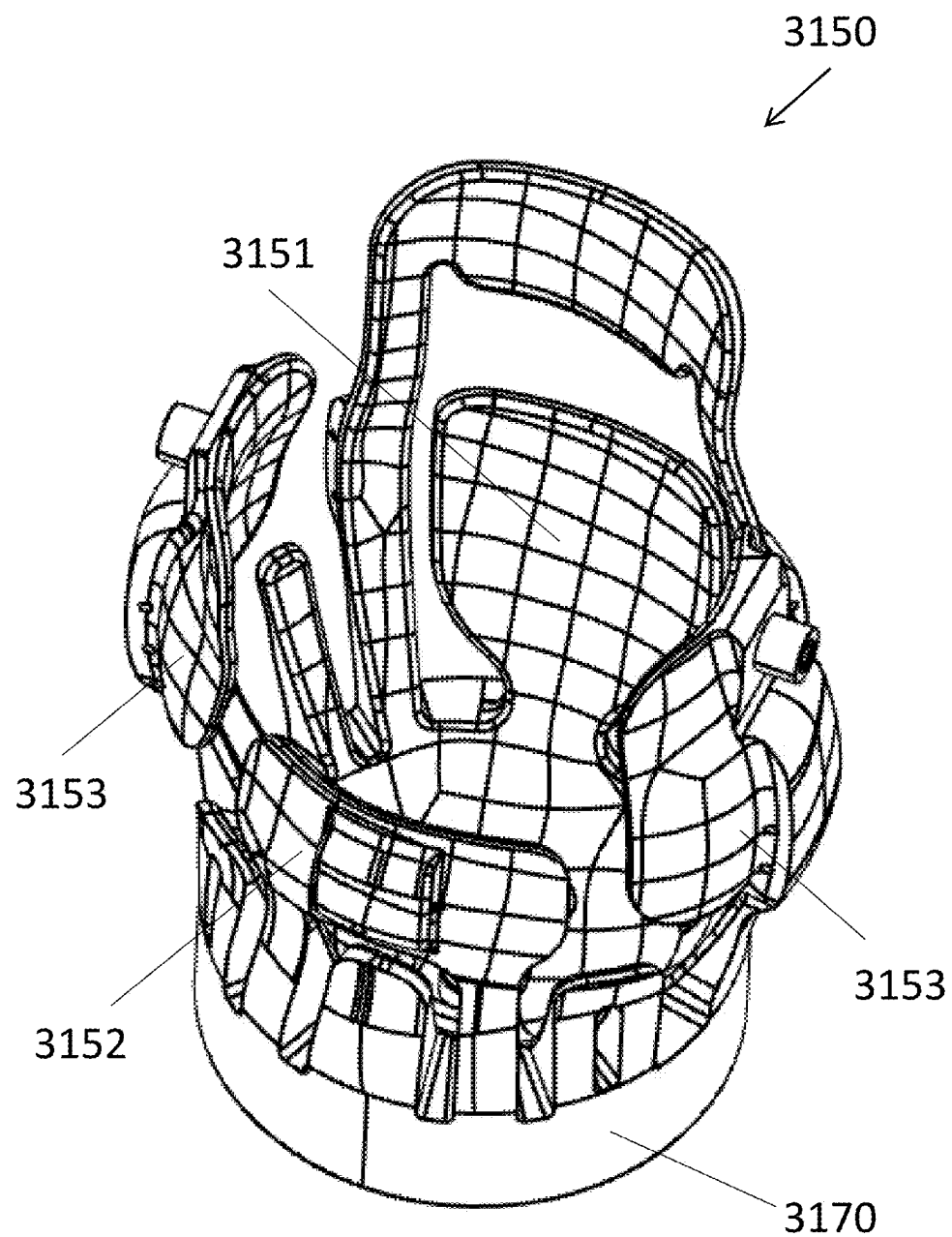
FIGS. 5B-C are perspective views of a distal socket of the socket of FIG. 5A.
Figure 5C:
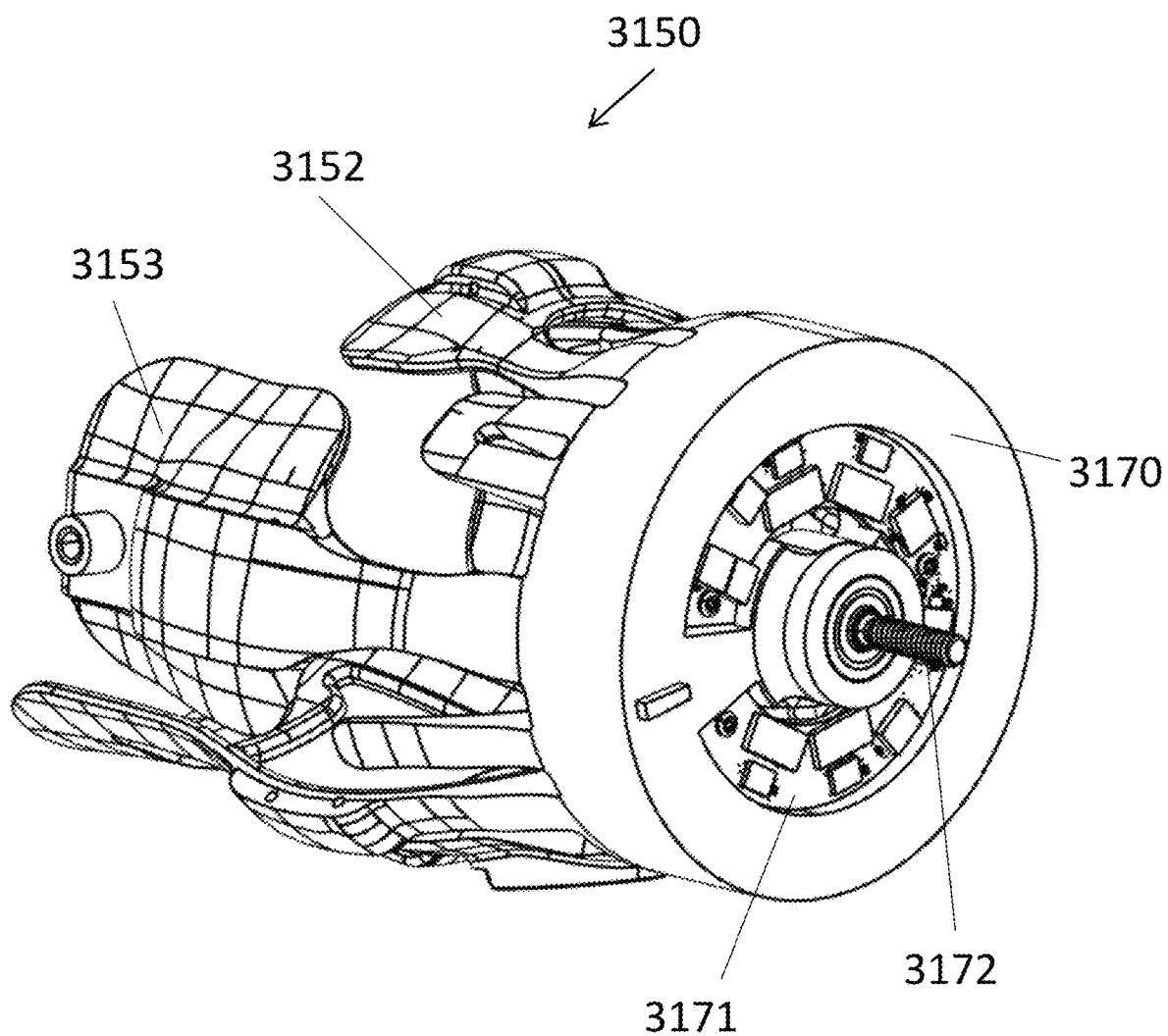

FIGS. 5A-C illustrate another embodiment of a socket 3100 that may be used with a prosthetic extremity, such as prosthetic forearm 200 and/or prosthetic hand 300. Socket 3100 may be generally similar in structure and function to socket 100 and/or socket 1100. Socket 3100 and variations thereof are described in greater detail in U.S. patent application Ser. No. 16/992,253, filed Aug. 13, 2020, the disclosure of which is hereby incorporated by reference herein. Briefly, socket 3100 may be user-generic or user-specific (e.g. contoured to fit a specific user). Socket 3100 may include a proximal socket 3110 and a distal socket 3150 coupled by one or more joints 3180, which may be polycentric joints. Proximal socket 3110 may couple to a user's upper arm, generally similar to proximal socket 1110. FIGS. 5B-C illustrate distal socket 3150, which may be configured to receive a user's residual limb, much like distal socket 1150, and to couple to a prosthetic device, such as prosthetic forearm 200, via a linking portion 3170. Referring to FIG. 5C, the linking portion 3170 may include a recess, such as a C-shaped recess, that can receive an electronics board 3171 therein. As shown, the electronics board 3171 may also be C-Shaped. A bolt 3172 or other similar fastener may pass through the center portion of linking portion 3170 (including through the center of the electronics board 3171), to assist in coupling the distal socket 3150 to a prosthetic extremity, such as prosthetic forearm 200.

One of the main differences between distal socket 1150 and distal socket 3150 lies in the particular form factor of the portions of the distal socket in which the residual limb of the user is received. For example, referring generally to FIGS. 5A-C, the distal socket 3150 may include individual panels or groups of panels that are intended to contact the user's limb and secure the distal socket to the user's limb. In the particular illustrated example, distal socket 3150 may include a posterior panel 3151, an anterior panel 3152, and two side panels 3153. These panels 3151-3153 may provide a large portion of the surface area of contact between the user's residual limb and the distal socket 3150. Other than the specific differences described above, socket 3100 may be otherwise similar or identical to socket 1100.

The sensor array 2000 described above may be suitable for use with socket 3100 similar to the description above of its use with socket 1100. However, some modifications may be desirable. For example, the central base area 2510 of the flex PCB 2500 of FIG. 3E is shown and described as including additional electronic components, such as MCU, positioned thereon. These additional electronics beyond the sensors may add bulk to the sensor array 2000, particularly near the central base area 2510. As noted above, the distal socket 3150 of socket 3100 may include an electronics board 3171 positioned in a recess in the linking portion 3170, and that electronics board 3171 may include some or all of the electronics necessary to store, process, and/or otherwise use information obtained from sensor array 2000. Thus, electronics other than the sensors, such as an MCU, IC, or similar components in the central base area 2510, may be omitted or moved to the electronics board 3171, resulting in a reduced profile of the sensor array 2000. Although not separately identified in FIG. 5C, one or more openings may be present at or near where the electronics board 3171 is received within the recess in linking portion 3170 so that connectors may extend from a sensor array 2000 (positioned within the interior of distal socket 3150) to the electronics board 3171 to connect the sensor array 2000 and the electronics board 3171. It should be understood that this modification may be made to other sockets described herein—in other words including an electronics board in another position outside the interior of the distal socket so that the electronics on sensor array 2000 may be minimized or omitted (other than the sensor components themselves) to reduce the profile of the sensor array 2000.

Although sensor array 2000 may be fully suited for use with socket 3100, there may be certain additional modifications that may be desirable. For example, the particular form factor of socket 3100, and particularly distal socket 3150, may not be as complementary to the form factor of sensor array 2000 as is distal socket 1150. This may be because, for example, distal socket 1150 has more of a continuous interior cup shape while distal socket 3150 has individual panels which extend different lengths, and sometimes significantly different lengths, for example comparing anterior panel 3152 to side panels 3153. In view of this, other embodiments of sensor arrays may be used with distal socket 3150, with these other embodiments having much in common with sensor array 2000, but with generally different form factor and other differences as well. As with sensor array 2000, it should be understood that the sensor arrays described below may be particularly suited for the use in prosthetic devices, but may find use in various other applications described in more detail below.

Figure 6A:
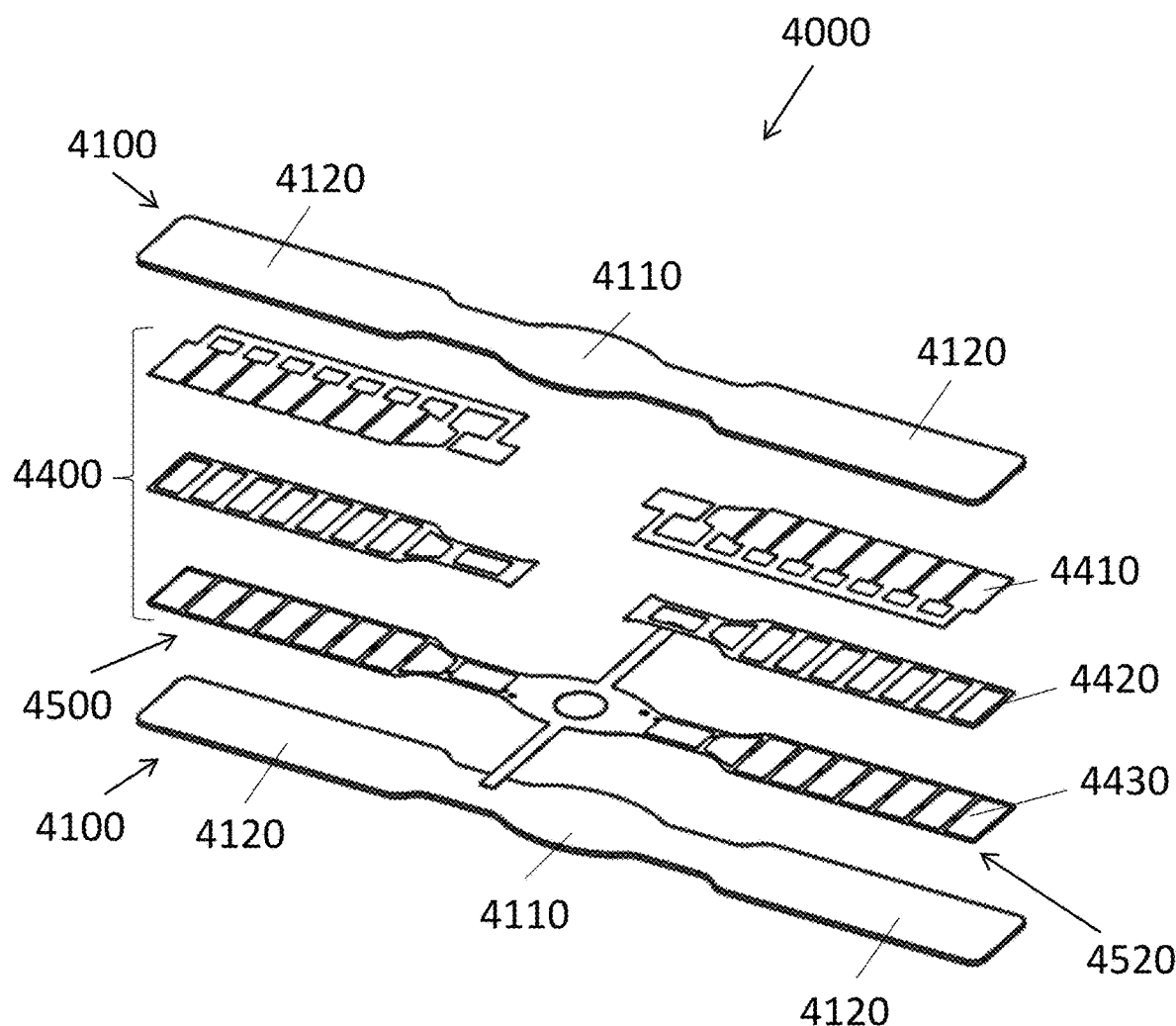
FIG. 6A is an exploded view of a sensor array according to another embodiment of the disclosure.
Figure 6B:
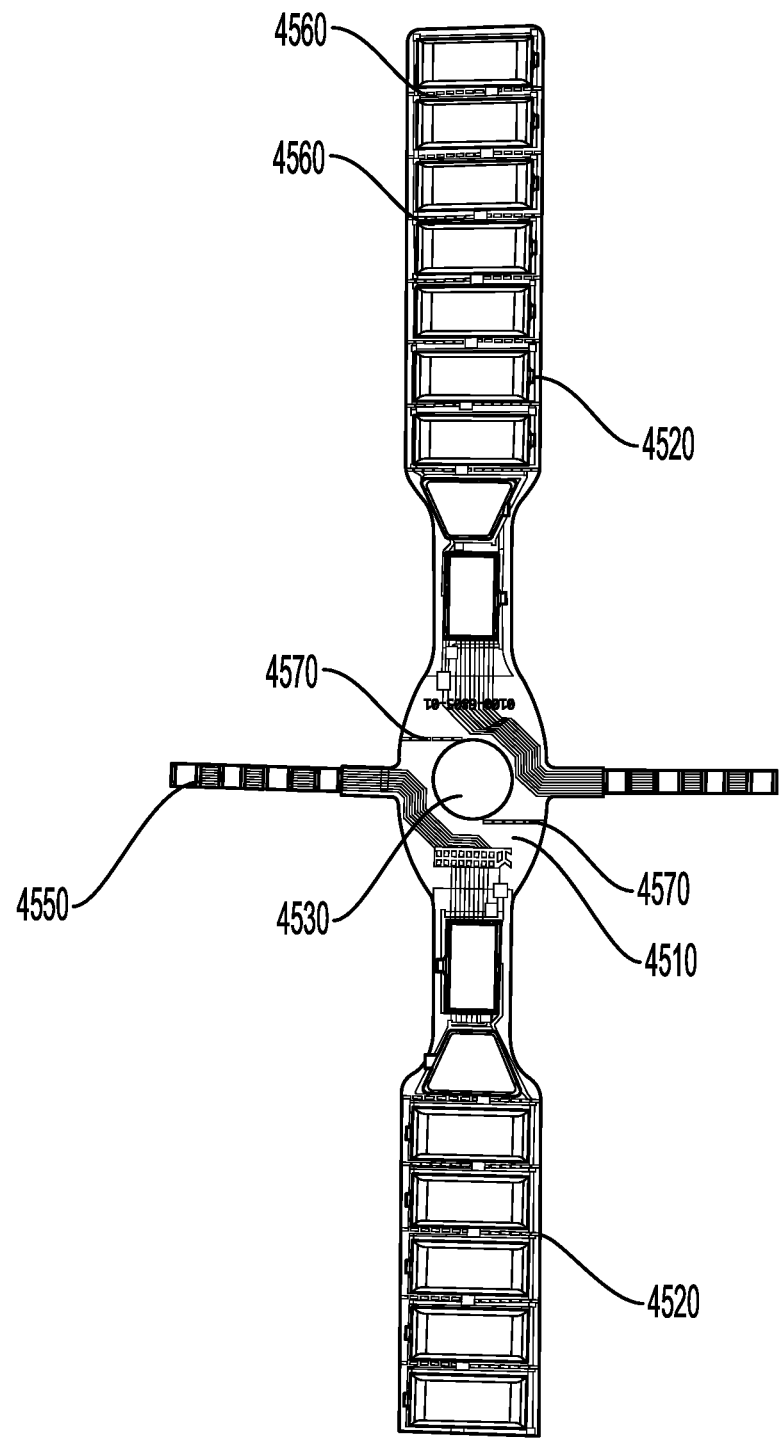
FIGS. 6B-C are top and bottom views, respectively, of the sensor array of FIG. 6A, with certain layers omitted from the views.
Figure 6C:
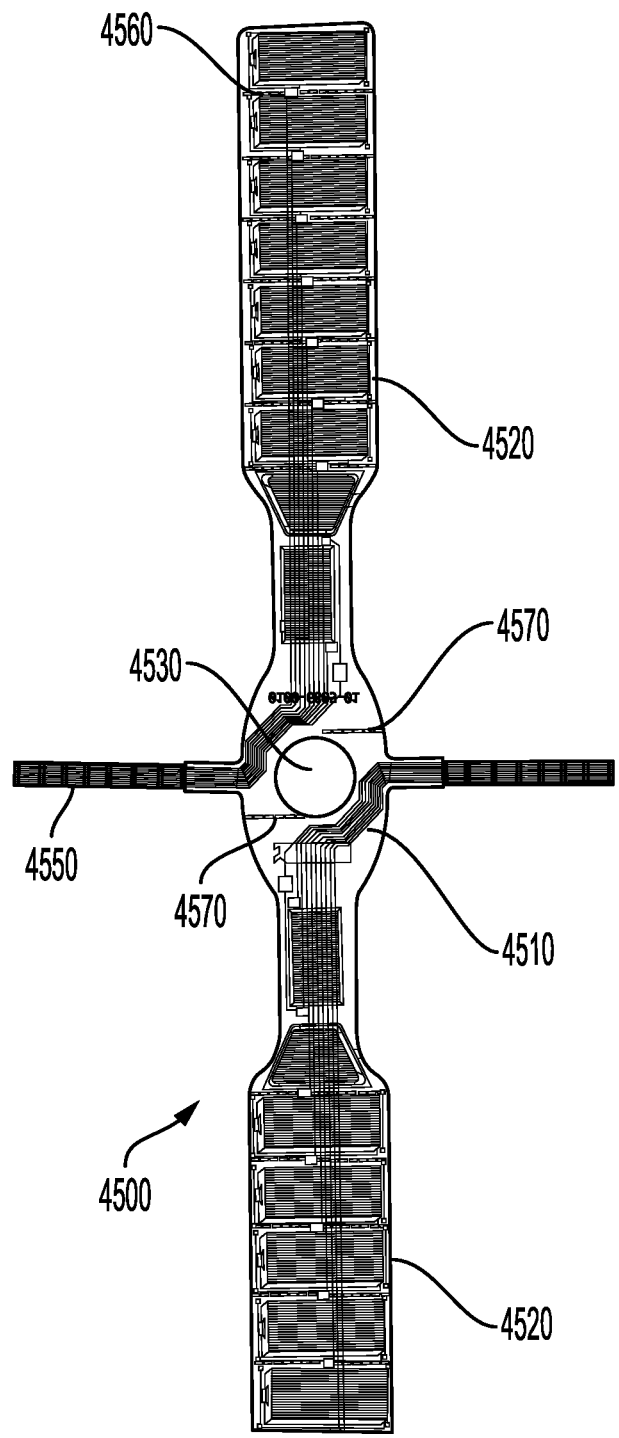

FIGS. 6A-C illustrate an embodiment of a biometric sensor array 4000 that may have many similarities to sensor array 2000. In the exploded view of FIG. 6A, sensor array 400 is shown as including a plurality of layers, generally similar to those shown and described in connection with sensor array 2000. For example, sensor array 4000 may include a skin contact layer 4100, which may be substantially similar or identical to skin contact layer 2100. For example, skin contact layer 4100 may be formed of any of the materials described above in connection with skin contact layer 2100, including biocompatible foams. And it should be understood that, as with skin contact layer 2100, skin contact layer 4100 may be provided on one or both sides of the sensor array 4000. In the illustrated embodiment, two skin contact layers 4100 are positioned on the opposite faces of the sensor array 4000, effectively sandwiching the most or all of the other components of the sensor array 4000 between the skin contact layer(s) 4100. However, also as described above in connection with skin contact layer 2100, skin contact layer 4100 may be formed in other ways and/or of other materials, for example by using materials in addition to (or other than) foam, such as silicone materials. Still further, as described above in contact with skin contact layer 2100, skin contact layer 4100 may be formed by overmolding using any suitable material. It should be understood that these material and/or manufacturing options for skin contact layer 4100 apply to all other skin contact layers described herein, unless stated explicitly otherwise or unless context demands otherwise.

One of the main differences between skin contact layers 4100 and 2100, and indeed between sensor arrays 4100 and 2100 (as well as most or all of the remainder of the sensor arrays described herein) lies in the particular form factor. In other words, while sensor array 2000 (and its corresponding skin contact layer) is shown and described above as having eight arms, sensor array 4000 is substantially linear, or may be thought of as having a single pair of arms aligned at 180 degrees. For example, skin contact layer 4100 may be thought of as including a central base area 4110 and two arms 4120.

Another main difference between sensor array 2000 and sensor array 4000 is that sensor array 4000 is illustrated without additional contact members (such as contact members 2300) or any corresponding intermediate layer (such as intermediate layer 2200) designed to receive those contact members. The contact members 2300 described above are generally useful for helping to ensure good contact between a user's body and the sensor layer (e.g. sensor layer 2400). However, depending on the number, shape, and size of the contact members 2300, it may be desirable to omit the contact members 2300 in some embodiments (including in alternate embodiments of sensor layer 2000) in order to reduce the overall bulk of the sensor array. This may be particularly helpful if there is limited space wherever the sensor array is received. And while omitting contact members 2300 may in some scenarios reduce the effectiveness of contact between the user's body and the sensor layer 2400, contact between the user's body and the sensor layer 2400 may be sufficient in the absence of the contact members 2300, particularly if the sensor array is able to make good contract with the user's body (e.g. a high proportion of the surface area of the sensor array is in close contact with the user's body).

Still referring to FIG. 6A, the sensor array 4000 may also include a sensor layer 4400 and a flex PCB layer 4500. Sensor layer 4400 may be similar or identical to sensor layer 2400. For example, a top portion of the sensor layer 4400 may be a semiconductor layer 4410, for example a carbon film or carbon ink that is printed, coated, or otherwise provided with respect to other portions of the sensor layer 4400. A spacer or adhesive film 4420 may be positioned between the semiconductor layer 4410 and an underlying copper layer 4430. It should be understood that, although the term "copper layer" may be used herein for this and other embodiments, the layer may also be considered a conductive layer formed using copper and/or other conductive materials, such as silver, etc. The adhesive layer 4420 may include a plurality of cutouts or recesses (rectangular in the illustrated embodiment) so that the copper layer 4430 and the semiconductor layer 4410 are spaced apart in the absence of applied force, and contact one another through the cutouts or recesses upon application of force, substantially similar to sensor layer 2400. It should be understood that copper layer 4430 is described as being copper, it may in some embodiments be other conductive materials, as is true for other embodiments described herein. Also, as in other embodiments described herein, the copper layer 4430 may be, but do not necessarily need to be, printed or otherwise applied directly to the flex PCB 4500. In the illustrated embodiment, sensor layer 4400 includes nine FSR sensors on each arm 4520 of the flex PCB 4500. However, as described herein, the sensors may be other types of sensors than FSRs.

FIGS. 6B-C illustrate top and bottom views of sensor array 4000 with the skin contact layers 4100 omitted. Flex PCB layer 4500 may include a central base area 4510 between the adjacent arms 4520, and the central base area 4510 may include an aperture 4530. Aperture 4530 may provide an opening for items like bolt 3172 to pass through if the sensor array 4000 is received within socket 3100. Flex PCB layer 4500 may include two tail connectors 4550, with each tail connector 4550 electrically coupled to a corresponding one of the arms 4220 (and sensors positioned thereon). Tail connectors 4550 may be used to electrically connect the sensor array 4000 to another device, such as electronics board 3171. In some embodiments, the flex PCB layer 4500 contains no other electronics other than those that provide the functionality for the sensors, which may allow those electronic components (e.g. microcontrollers) to be moved to another device, such as electronics board 3171, to help minimize the entire profile of sensor array 4000.

Figure 6D:
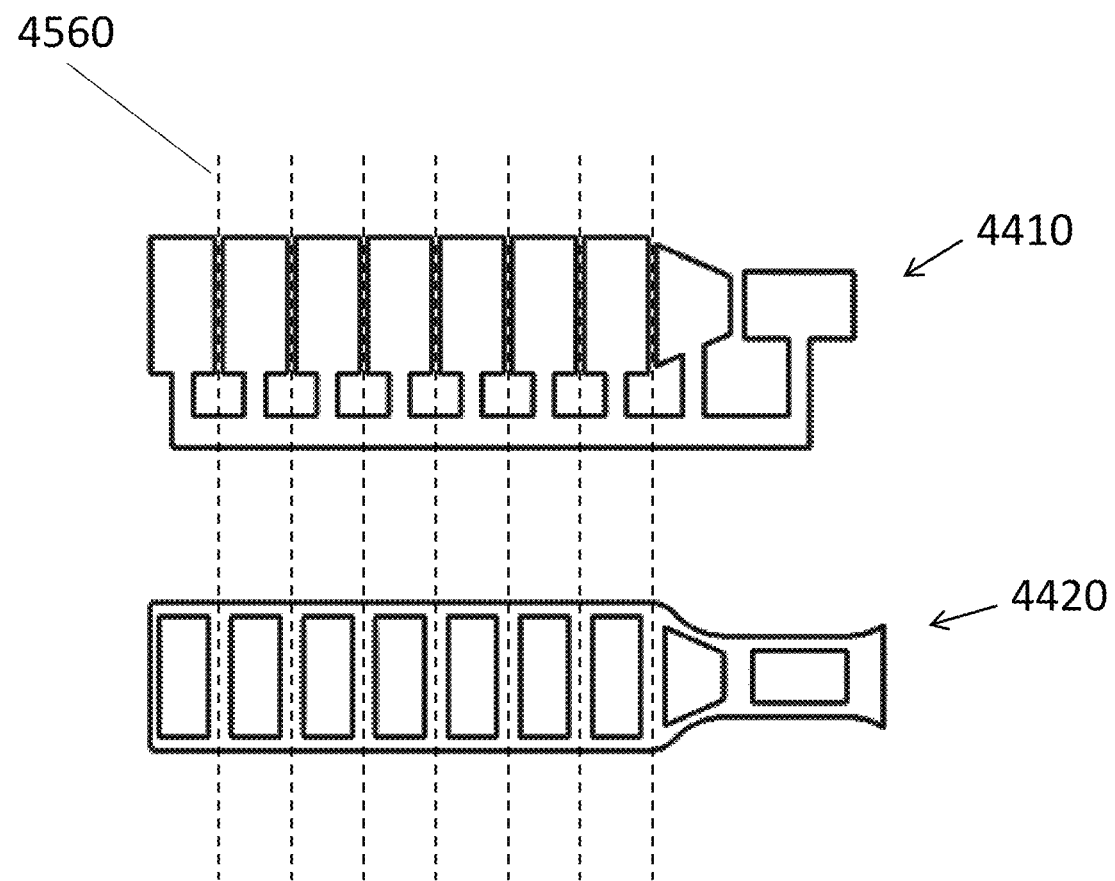
FIG. 6D is a schematic illustration of two layers of the sensor array of FIG. 6A, showing trim limes along which the sensor array may be trimmed.

As with sensor array 2000, sensor array 4000 may be substantially flexible, with arms 4520 and 4120 capable of wrapping around a contoured surface. For example, if sensor array 4000 is positioned within socket 3100, the central base portions 4110, 4510 may be aligned with a central distal portion of the distal socket 3150, with the arms extending generally upward or proximally. With that positioning, one or both tail connectors 4550 max extend through one or more holes in the linking portion 3170 and couple to electronics board 3171. As best seen in FIG. 6C, the conductive (e.g. copper) traces extending from each individual FSR to tail connector 4550, may extend adjacent one another. In the illustrated configuration, the arms of sensor array 4000 may be trimmed to provide a desired size without losing overall functionality of the sensors. For example, trim lines 4560 may be provided on the sensor array 4000 between each pair of adjacent sensors. The trim lines 4560 are illustrated in FIGS. 6B-C, with FIG. 6D providing a schematic illustration of where the trim lines 4560 are positioned relative to the semiconductor layer 4410 and the adhesive layer 4420. Although seven trim lines 4560 are illustrated in FIG. 6D, it should be understood that an eighth trim line may be positioned between the two FSRs on end of the sensor array 4000 closest to the central base portion. It should be understood that, in FIG. 6D, connecting bridges are shown in the carbon film layer 4410, and those bridges would be cut away as close as practical to the corresponding FSR pad region (generally rectangular regions in carbon film layer 4410). These connecting bridges may only be useful for manufacturing purposes, and would be removed whether or not the individual sensors are trimmed along trim lines 4560.

If sensor array 4000 is too large for a particular application (e.g. a socket 3100 that is sized for a child), the sensor array 4000 may be cut along the desired trim line 4560 to reduce the total number of sensors and the length of the particular sensor arm. For example, sensor array 4000 may be trimmed to remove three sensors from each arm to reduce the size of the sensor array 4000. The overall functionality will remain, even after trimming, because at least some sensors will remain on the sensor array 4000. In some applications, more sensors may provide better overall functionality if those sensors provide more total usable data. However, in situations where it is desired to trim one or more sensors away from the sensor array 4000, the sensors being removed are typically less likely to have provided useful data if they were not removed from the sensor array 4000. Thus, by allowing the sensor array 4000 to be trimmable while maintaining use of the remaining sensors, a single sensor array 4000 may be customized by a user without losing any meaningful functionality. Referring to FIG. 6B, the sensor array 4000 may be even further trimmable to remove an entire arm 4120/4520. In FIG. 6B, two additional trim lines 4570 are illustrated on the central base area 4510 of flex PCB layer 4500 extending generally perpendicular to the arms on each side of the central aperture 4530. If it is desired to remove an entire arm of the sensor array 4000, the sensor array 4000 may be cut along one of the two trim lines 4570 to remove an entire arm, with the remaining arm (and specifically and remaining untrimmed sensors on the remaining arm) providing the desired functionality. This may allow for even further customization of the size and sensor array 4000. In fact, sensor array 4000 could be turned into two individual sensor arrays by cutting the sensor array to separate one arm 4520 (and its corresponding connector tail 4550) from the other arm (and its corresponding connector tail). Finally, each tail connector 4550 may be similarly trimmed to a smaller size prior to connecting to another device, such as electronics board 3171, to provide for still further size customization of the sensor array 4000.

Although sensor arrays 2000 and 4000 are provided as one or more pairs of arms extending from a central base area, in other embodiments, the sensor arrays may be provided in other shapes, including "patch" type configurations. These patch sensor arrays may share various features and concepts as described above for sensor arrays 2000 and 4000, with the main difference being the particular form-factor of each sensor array. Various embodiments of these patch-type sensor arrays are described in detail below.

Figure 7A:
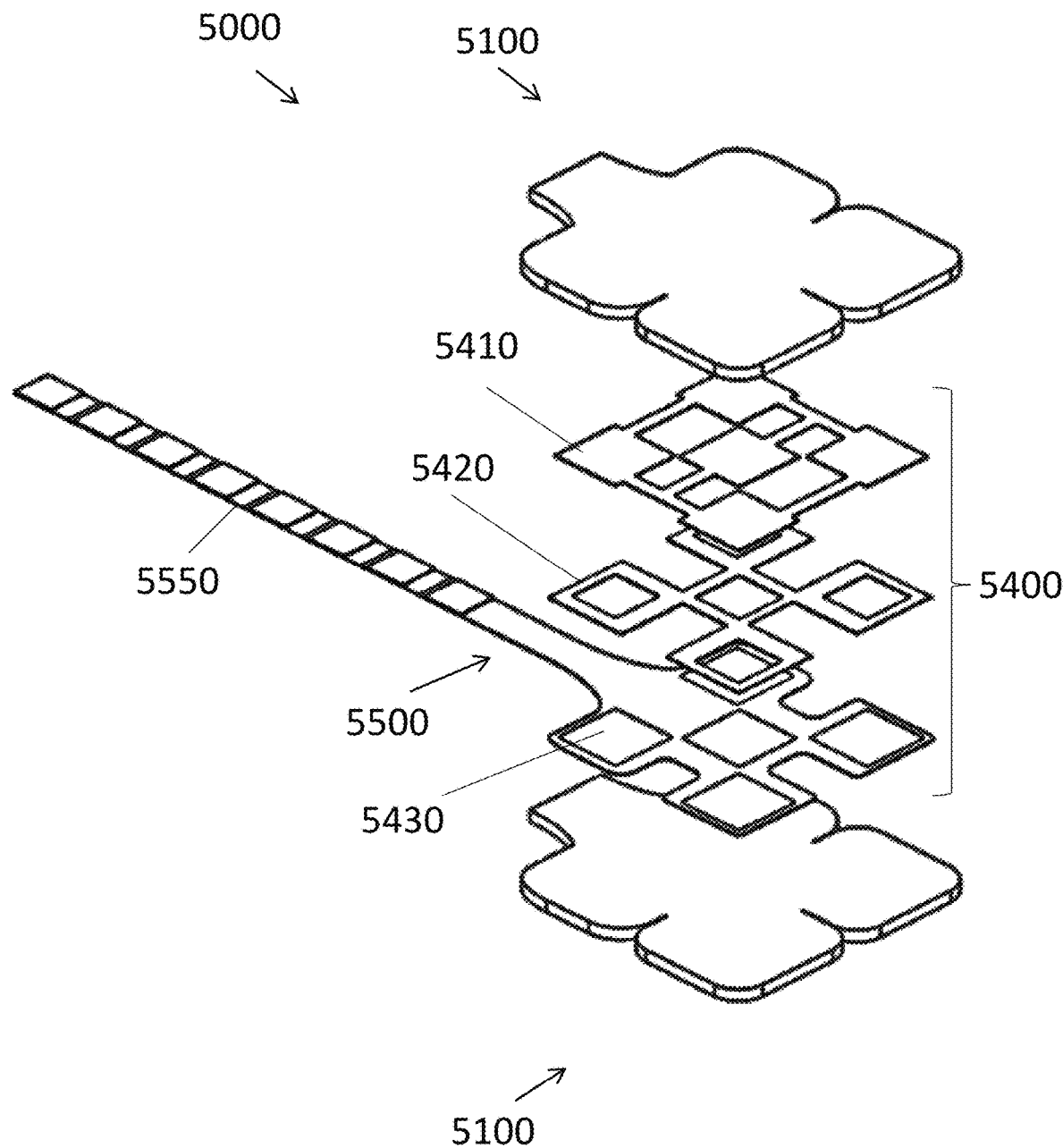
FIG. 7A is an exploded view of a sensor array according to a further embodiment of the disclosure.

FIG. 7A is an exploded view of a sensor array 5000, which may have significant features in common with sensor arrays 2000 and 4000, with the main difference being the form factor. For example, sensor array 5000 may include skin contact layers 5100 which may be formed of any of the materials and/or configurations (e.g. via overmolding) as described in connection with skin contact layers 4100. The sensor layer 5400 may include a semiconductor layer (such as a carbon film or ink layer) 5410, a spacer or adhesive layer 5420, and a copper layer 5430, and the copy layer 5430 may be deposited, printed, or otherwise disposed directly on the flex PCB layer 5000. A connector tail 5550 may extend from the flex PCB layer 5550.

Figure 7B:
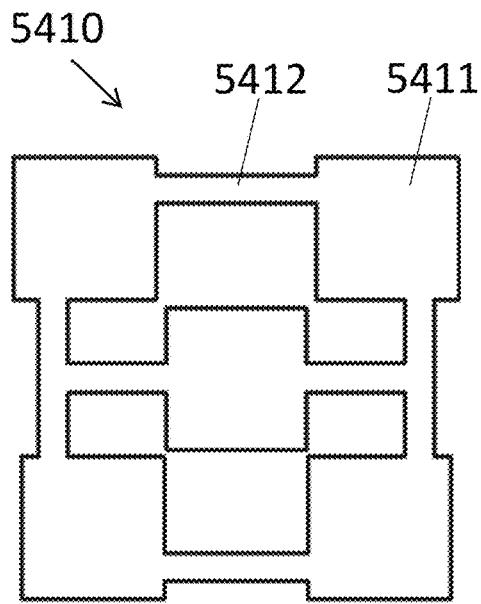
FIGS. 7B-D are plan views of components of the sensor array of FIG. 7A.
Figure 7C:
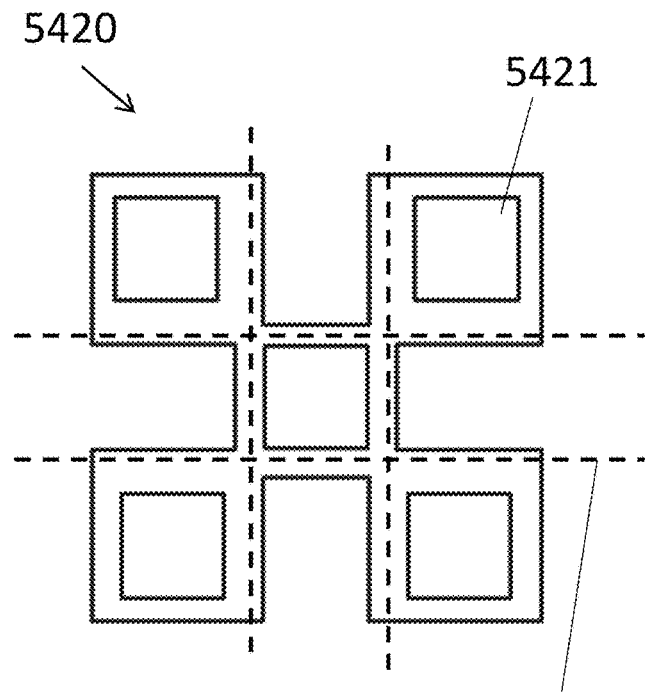

FIG. 7B illustrates a plan view of semiconductor layer 5410 prior to assembly. Semiconductor layer 5410 may include a plurality of generally rectangular or square shaped FSR pads 5411 coupled via connecting bridges 5412, similar to semiconductor layer 4410. After assembling the adhesive layer 5420 to the semiconductor layer 5410, the connecting bridges 5412 may be cut adjacent the FSR pads 5411. FIG. 7C illustrates a plan view of adhesive layer 5420, which similar to other embodiments described herein, includes recesses or cutouts 5421, so that upon application of pressure, the FSR pads 5411 may make contact with the copper layer 5430 through the cutouts 5421. It should be understood that the cutouts 5421 in adhesive layer 5420 correspond to the positions of the individual FSR sensors in sensor array 5000. Thus, in the illustrated embodiment, sensor array 5000 includes five FSRs. Still referring to FIG. 7C, trim lines 5560 are illustrated. As with sensor array 4000, after sensor array 5000 is assembled, if the size of the sensor array 5000 needs to be reduced for a particular application, the sensor array 5000 may be cut along one or more of the trim lines 5560 (including either partial or complete cuts along the trim lines 5560), in order to remove one or more of the sensors from the sensor array 5000, while retaining complete functionality of any remaining sensors. In other words, the conductive (e.g. copper) tracing on flex PCB that connects the FSR sensors to an electronics board (e.g. electronics board 3171) via connector tail 5550 may be configured so that individual ones of the sensors may be cut away without disturbing the electric pathways of the remaining sensors. Also, similar to embodiments described above, the connector tail 5550 may be trimmed itself to reduce the size of the connector tail, prior to connection to an electronics board, in order to better size the sensor array 5000 for the particular application.

Figure 7D:
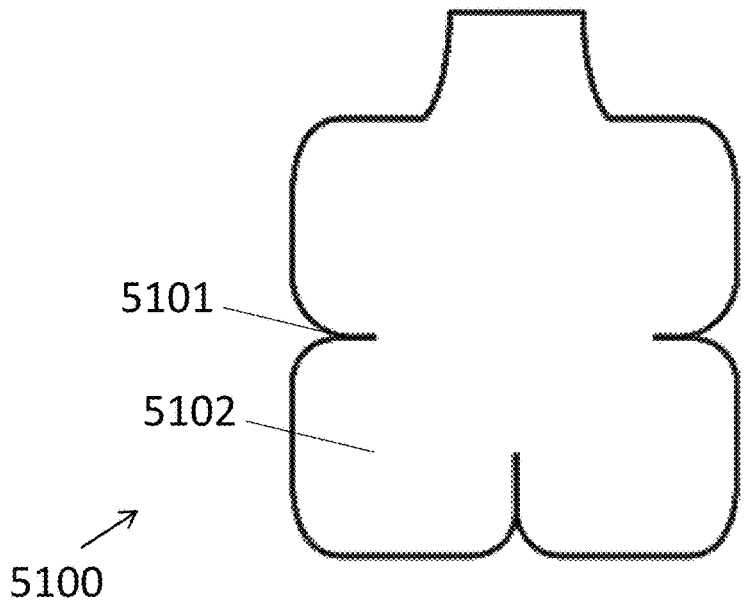

FIG. 7D is a plan view of one of the skin contact layers 5100. As illustrated in FIG. 7D, the skin contact layer 5100 may include a plurality of strategically placed slits 5101 that extend a distance inward from an outer edge of the skin contact layer 5100. In FIG. 7D, skin contact layer 5100 includes three slits 5101 generally corresponding to spaces between adjacent ones of the sensors (e.g. between FSR pads 5411), except no slit is provided on the portion of the skin contact layer 5100 that corresponds to the location of connector tail 5550. The slits 5101 may also be aligned with recesses or cutouts in the flex PCB layer 5500 (e.g. where the flex PCB layer 5500 is absent) to assist with bending about the slits 5101. Individual areas 5102 that generally correspond to the locations of the FSR sensors are substantially unbroken between slits 5101. With this configuration, the sensor array 5000 may be configured to allow for bending or flexing of the areas 5102 about slits 5101, allowing for the sensor array 5000 to more easily conform to a user's skin while helping ensure bending does not occur at one of the sensors. It should be understood that individual areas 5102 may be continuous with one another, and need not be individual in the sense of being discontinuous with another individual area. Although sensor array 5000 may be suitable for use in any application and be suitable for contact with any portion of a user, the sensor array 5000 may be particularly suitable for connecting to the interior of one of the panels 3151, 3152, 3153 of distal socket 3150. By having generally corresponding overall shapes, the sensor array 5000 may be able to provide sensor-to-skin contact along substantially the entire interior surface of the panel to which the sensor is attached. And it should be understood that each of the panels may include sensor array 5000 (or any of the other sensor arrays described herein, whether trimmed or not) to provide a very high ratio of sensor-to-skin contact in relation to the total available interior surface area present in distal socket 3150.

The general configuration of "patch" sensor array 5000 may be provided in any desirable form factor, for example to more closely correspond to the shape of the surface onto which the sensor array will be applied. In the example of distal socket 3150, different form factors may be applied to the sensor arrays to correspond as closely as possible to the shape and size of the panels 3151, 3152, 3153, while maintaining the ability to trim the sensor arrays further down to size based on the exact application. However, as is described in greater detail below, these sensors may be used in a significant number of applications—particularly human-machine interface applications—with the sensors providing the same benefit (e.g. the ability to maximize and customize the amount of sensor-to-user contact area given the available surface area of the item to which the sensors are applied). The additional embodiments of the patch sensors are described below more briefly than sensor array 5000, but it should be understood that the concepts and specifics of sensor array 5000 may apply with similar or equal force to the various patch-type sensor arrays described below, unless explicitly described otherwise.

Figure 8A:
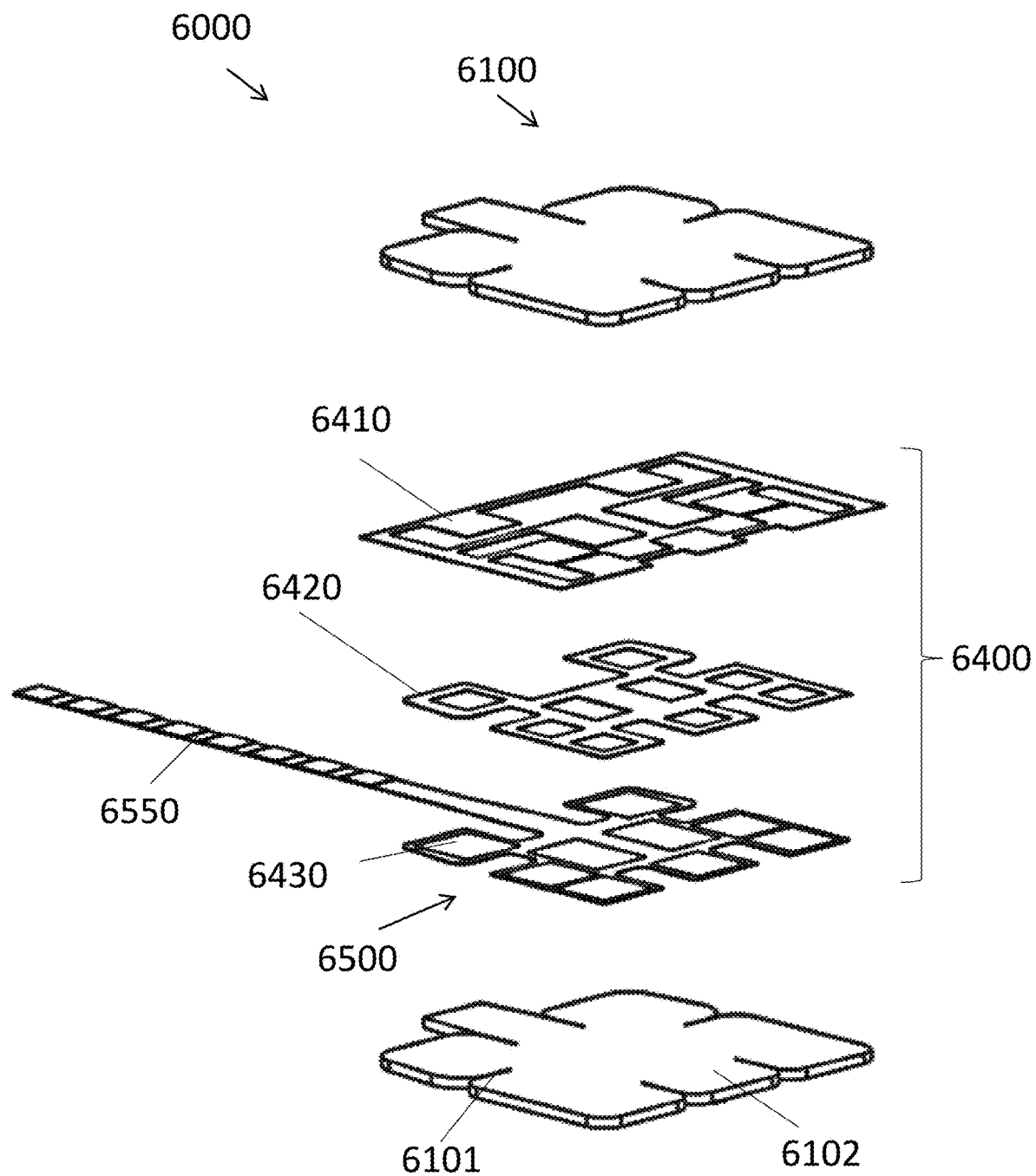
FIG. 8A is an exploded view of a sensor array according to yet another embodiment of the disclosure.

FIG. 8A is an exploded view of another sensor array 6000 that is substantially identical to sensor array 5000, with the main exception being the number of sensors and the shape of the sensor array. For example, sensor array 6000 may include a skin contact layer 6100, which may include individual areas 6102 between slits 6101. Skin contact layer 6100 may be formed of foam, silicone, via overmolding, or using any material or process described for skin contact layers described above. The sensor layer 6400 may include a semiconductor layer (e.g. carbon film layer) 6410, a spacer or adhesive layer 6420, and a copper layer 6430, which may be applied directly to a flex PCB layer 6500. A connector tail 6550 may extend from the flex PCB layer 6500.

Figure 8B:
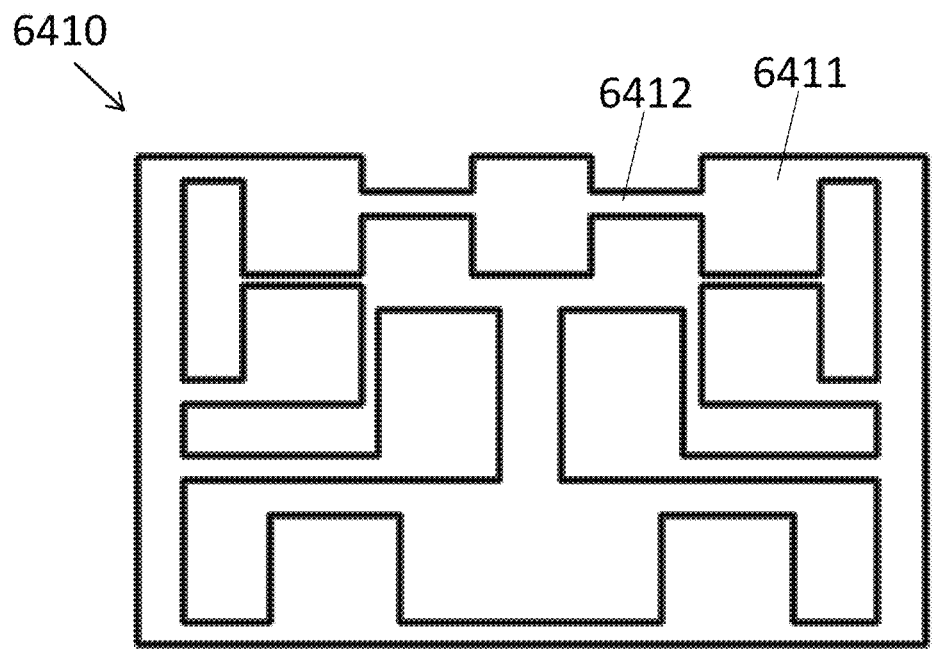
FIGS. 8B-C are plan views of components of the sensor array of FIG. 8A.
Figure 8C:
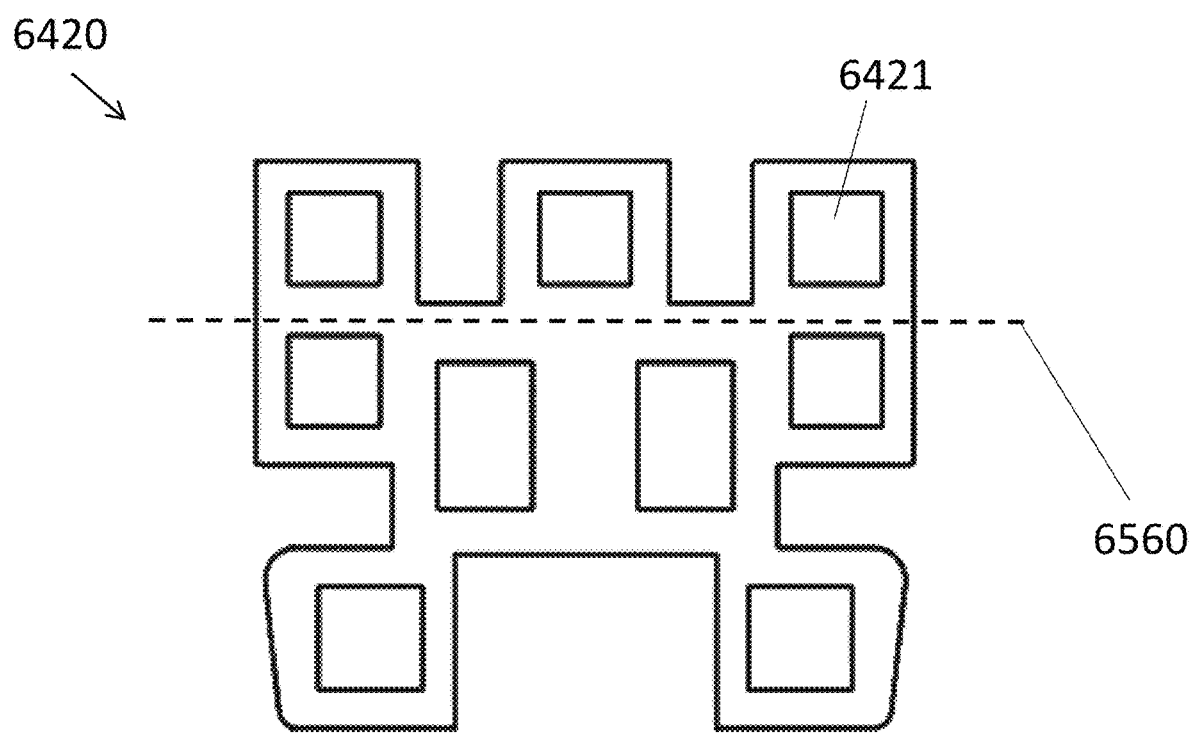

Semiconductor layer 6410 is shown in a plan view in FIG. 8B, and may include a plurality of FSR pads 6411 coupled by bridge connectors 6412, and the bridge connectors 6412 may be cut adjacent the FSR pads 6411 after assembly with the adhesive layer 6420. FIG. 8C illustrates a plan view of adhesive layer 6420, which may include a plurality of cutouts 6421 that may generally correspond to the locations of the individual FSR sensors. Sensor array 6000 may include nine sensors. FIG. 8C illustrates one exemplary trim line 6560 that may be used to trim one or more sensors from the sensor array 6000 without losing functionality of the remaining sensors. However, it should be understood that this is only one example, and nearly any combination of trim lines may be followed to cut away unwanted sensors, although the at least one sensor must of course remain for the sensor array 6000 to provide sensing functionality.

Figure 9:
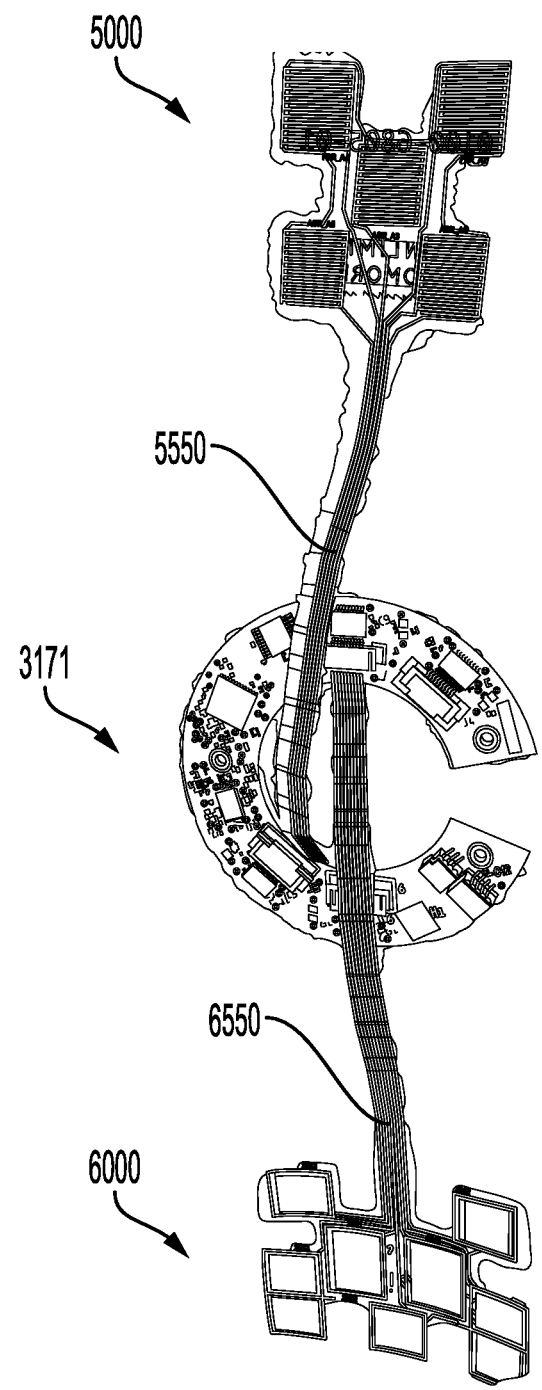
FIG. 9 illustrates the sensor arrays of FIGS. 7A and 8A connected to the electronics board of FIG. 5C.

As should be clear, any combination of the sensor arrays described herein (whether trimmed or not) may be used together with one another. For example, FIG. 9 illustrates sensor array 5000 (without any sensor trimming and with skin contact layers omitted for the illustration) and sensor array 6000 (without any sensor trimming and with skin contact layers omitted for the illustration) each connected to electronics boards 3171 via their respective connector tails 5550, 6550. In an exemplary use, the skin contact layers would be provided for the sensor arrays, the sensor arrays would be positioned on the interior of two of the panels 3151, 3152, 3153, the electronics board 3171 would be received within the corresponding recess in the linking portion 3170, and the connector tails 5550, 6550 would extend from the interior of the distal socket 3150 to the electronics board 3171 via openings in the linking portion 3170. It should be understood that additional components, such as connections between the electronics board 3171 and actuators within a prosthetic forearm 200 or prosthetic hand 3000, and connections between electronics board 3171 and a power source, are omitted from the view. However, in use, the sensor arrays 5000, 6000 may provide all the necessary input to electronics board 3171 for controlling movement of the prosthetic device, with electronics such as one or more MCUs on the electronics board 3171 processing the data received from the sensor arrays 5000, 6000.

Figure 10A:
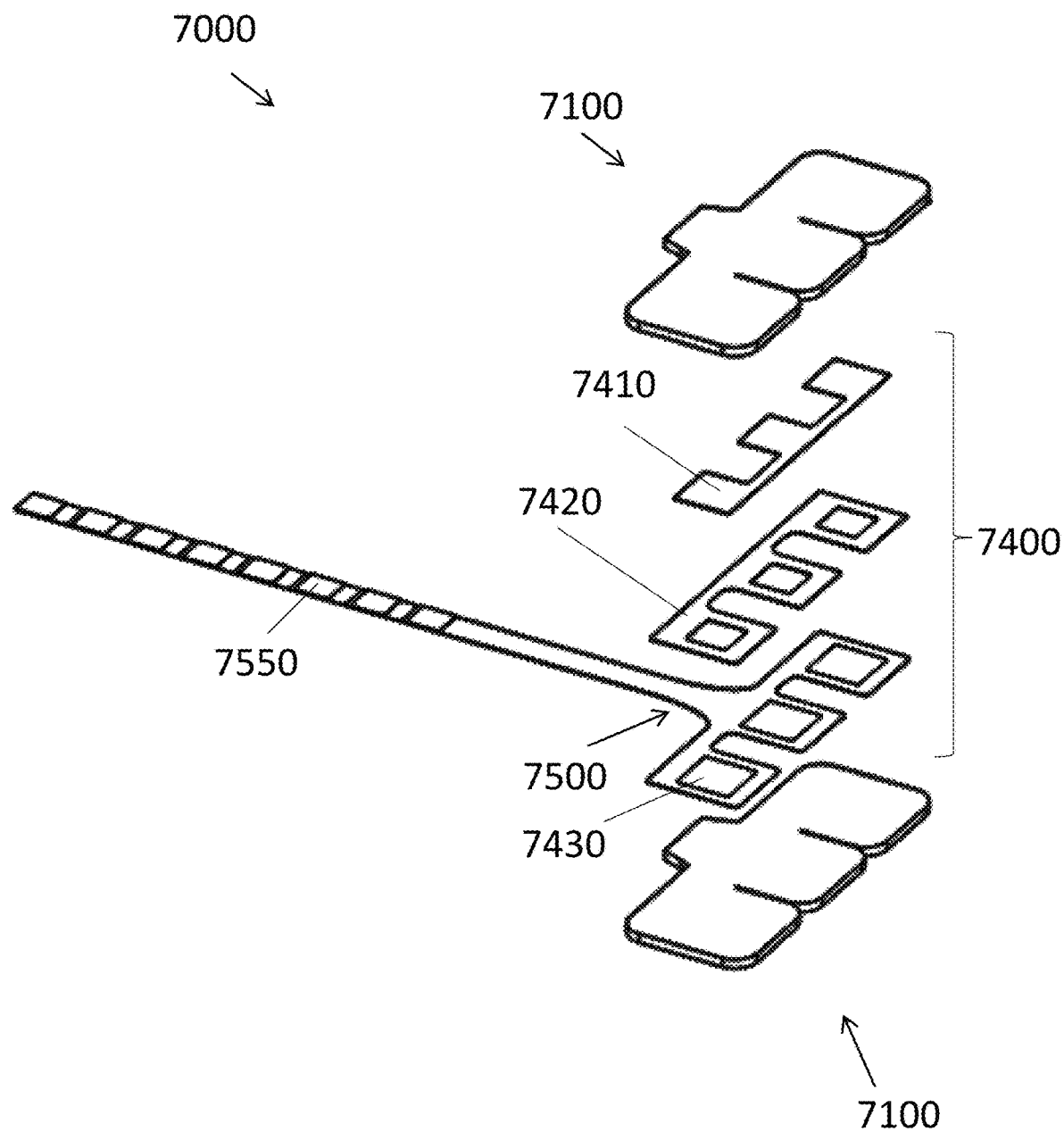
FIG. 10A is an exploded view of a sensor array according to yet another embodiment of the disclosure.

FIG. 10A is an exploded view of another sensor array 7000 that is substantially identical to sensor arrays 5000-6000, with the main exception being the number of sensors and the shape of the sensor array. For example, sensor array 7000 may include a skin contact layer 7100, which may include individual areas 7102 between slits 7101, as shown in FIG. 10D. Skin contact layer 7100 may be formed of foam, silicone, via overmolding, or using any material or process described for skin contact layers described above. The sensor layer 7400 may include a semiconductor layer (e.g. carbon film layer) 7410, a spacer or adhesive layer 7420, and a copper layer 7430, which may be applied directly to a flex PCB layer 7500. A connector tail 7550 may extend from the flex PCB layer 7500.

Figure 10B:
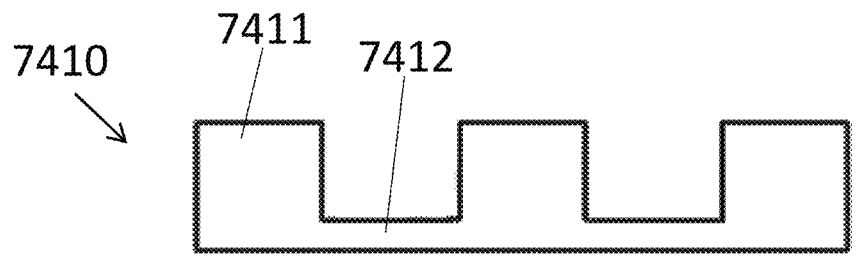
FIGS. 10B-D are plan view of the components of the sensor array of FIG. 10A.
Figure 10C:
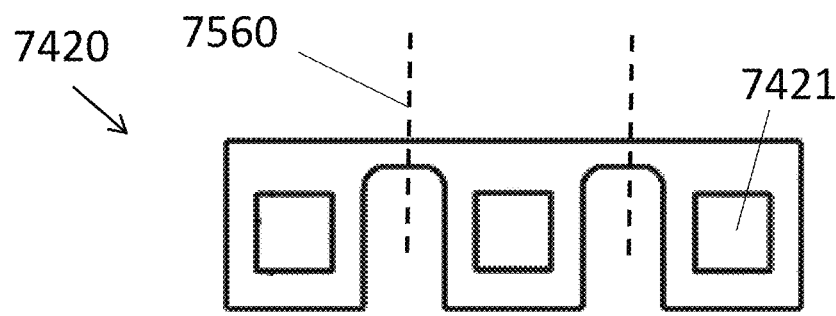
Figure 10D:
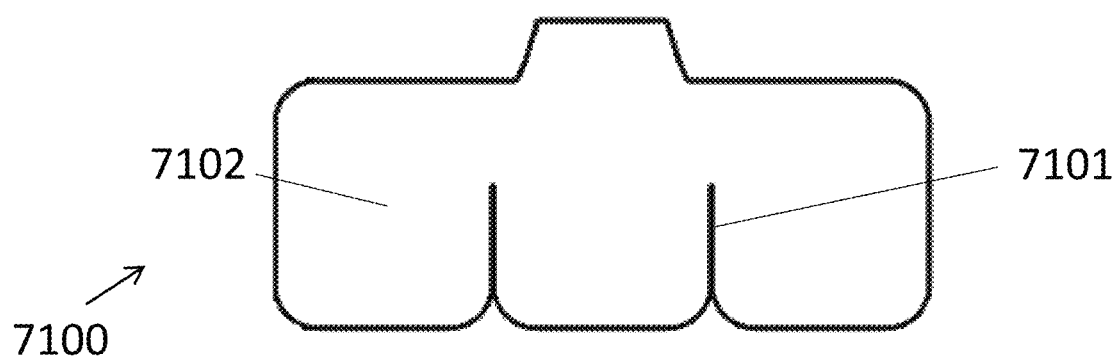

Semiconductor layer 7410 is shown in a plan view in FIG. 10B, and may include a plurality of FSR pads 7411 coupled by bridge connectors 7412, and the bridge connectors 7412 may be cut adjacent the FSR pads 7411 after assembly with the adhesive layer 7420. FIG. 10C illustrates a plan view of adhesive layer 7420, which may include a plurality of cutouts 7421 that may generally correspond to the locations of the individual FSR sensors. Sensor array 7000 may include three sensors. FIG. 10C illustrates two trim lines 7560 that may be used to trim one or more sensors from the sensor array 7000 without losing functionality of the remaining sensors. In this specific embodiment, one or both of the side sensors may be trimmed away from the sensor array 7000.

Figure 11A:
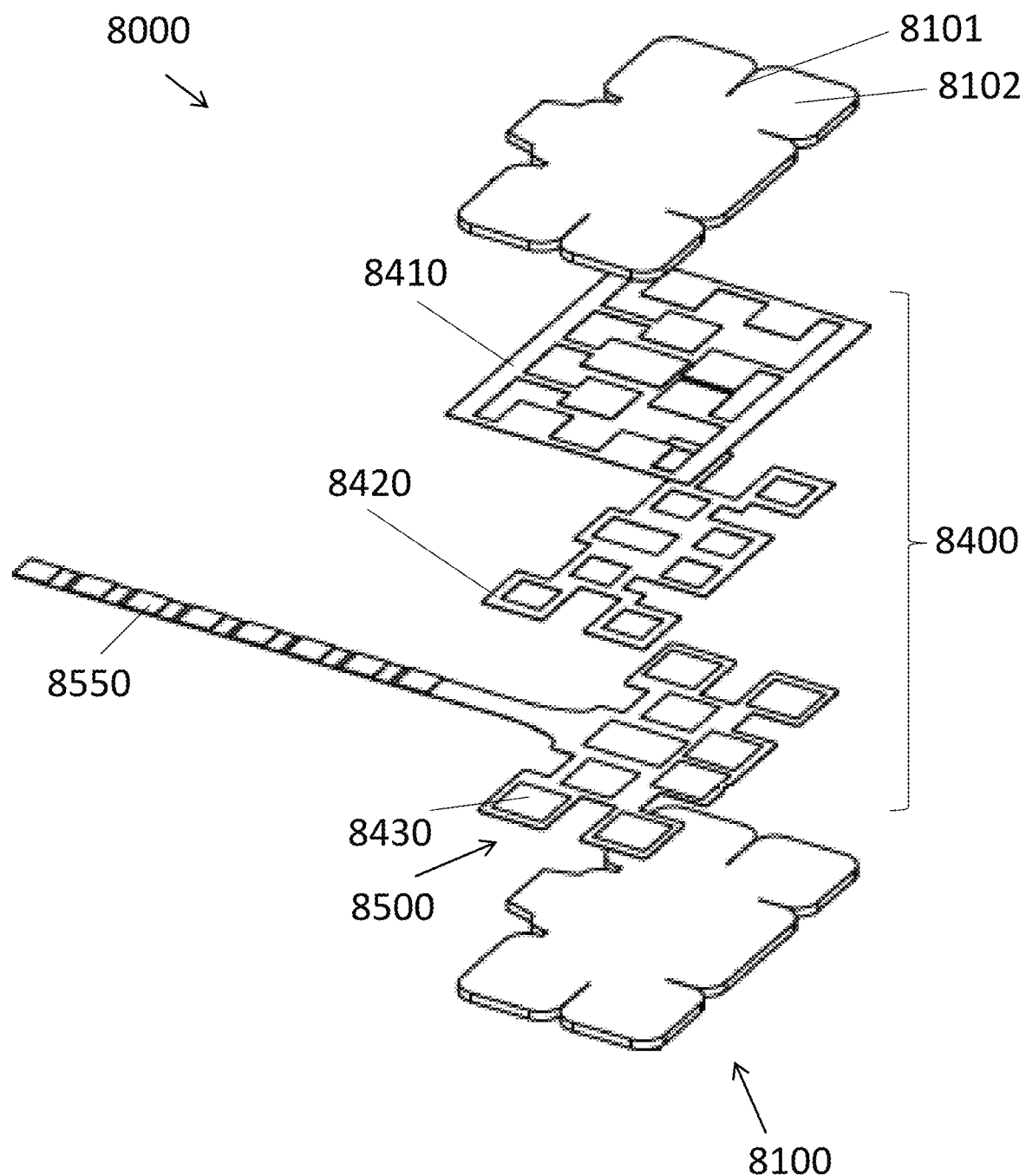
FIG. 11A is an exploded view of a sensor array according to yet a further embodiment of the disclosure.

FIG. 11A is an exploded view of another sensor array 8000 that is substantially identical to sensor arrays 5000-7000, with the main exception being the number of sensors and the shape of the sensor array. For example, sensor array 8000 may include a skin contact layer 8100, which may include individual areas 8102 between slits 8101. Skin contact layer 8100 may be formed of foam, silicone, via overmolding, or using any material or process described for skin contact layers described above. The sensor layer 8400 may include a semiconductor layer (e.g. carbon film layer) 8410, a spacer or adhesive layer 8420, and a copper layer 8430, which may be applied directly to a flex PCB layer 8500. A connector tail 8550 may extend from the flex PCB layer 8500.

Figure 11B:
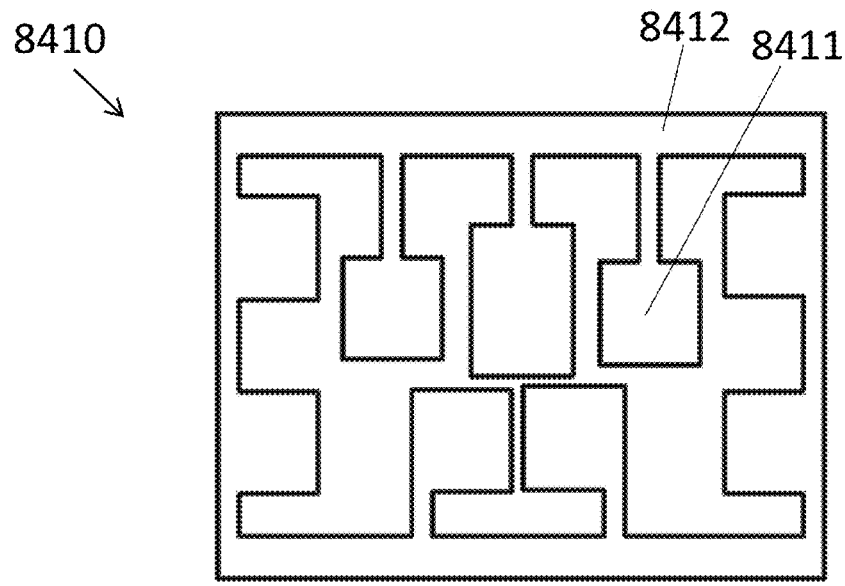
FIGS. 11B-C are plan views of components of the sensor array of FIG. 11A.
Figure 11C:
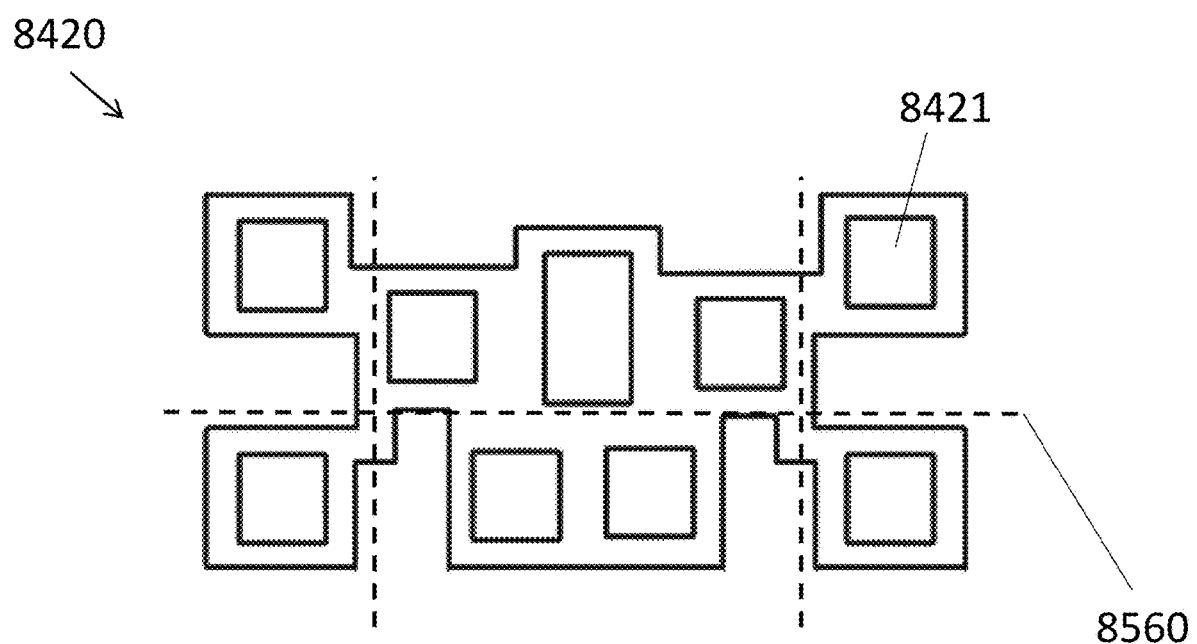

Semiconductor layer 8410 is shown in a plan view in FIG. 11B, and may include a plurality of FSR pads 8411 coupled by bridge connectors 8412, and the bridge connectors 8412 may be cut adjacent the FSR pads 8411 after assembly with the adhesive layer 8420. FIG. 11C illustrates a plan view of adhesive layer 8420, which may include a plurality of cutouts 8421 that may generally correspond to the locations of the individual FSR sensors. Sensor array 8000 may include nine sensors. FIG. 11C illustrates three exemplary trim lines 8560 that may be used to trim one or more sensors from the sensor array 8000 without losing functionality of the remaining sensors. However, it should be understood that these trim lines 8560 are only exemplary, and nearly any combination of trim lines may be followed to cut away unwanted sensors, although the at least one sensor must of course remain for the sensor array 8000 to provide sensing functionality.

Figure 12A:
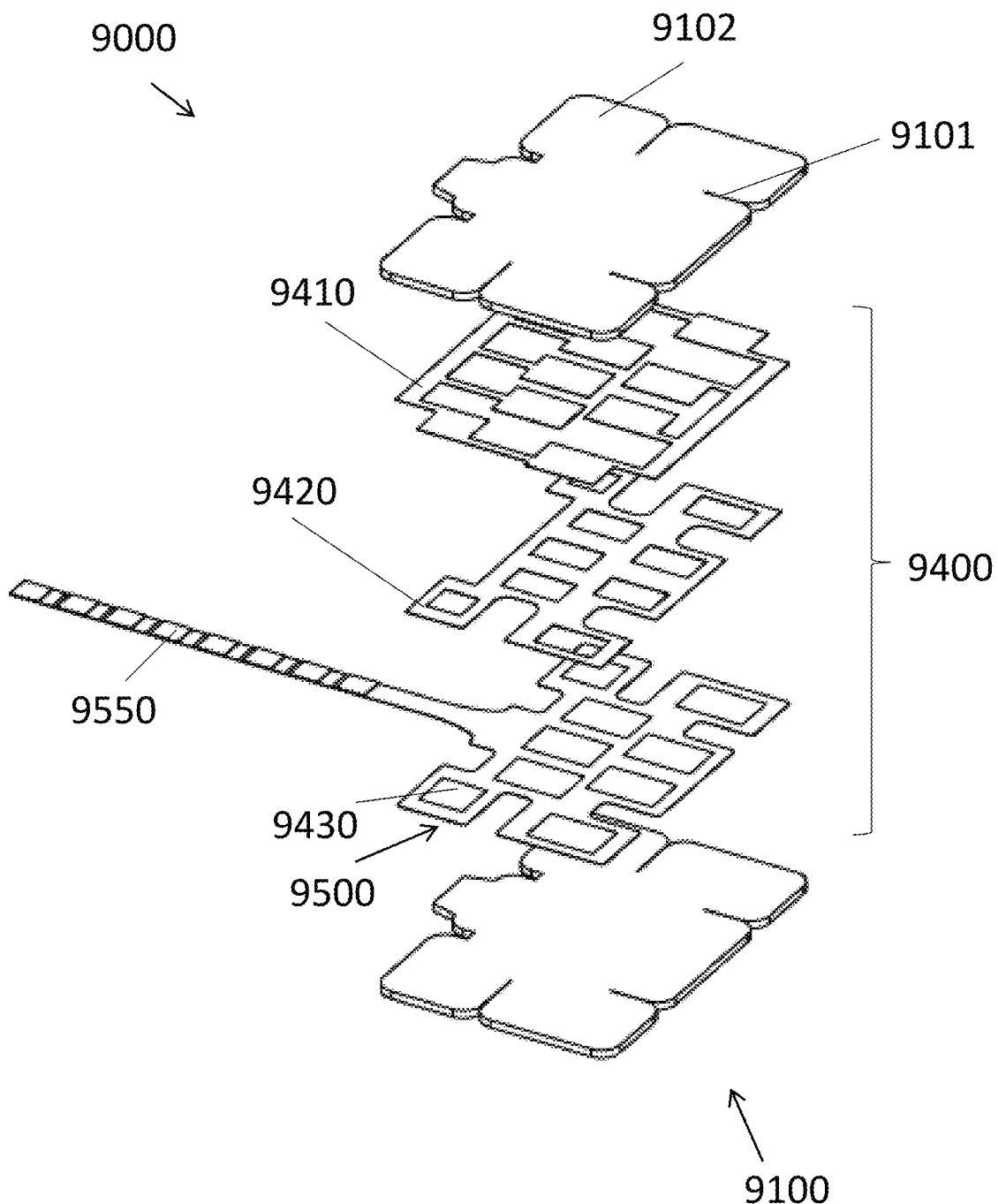
FIG. 12A is an exploded view of a sensor array according to still a further embodiment of the disclosure.

FIG. 12A is an exploded view of another sensor array 9000 that is substantially identical to sensor arrays 5000-8000, with the main exception being the number of sensors and the shape of the sensor array. For example, sensor array 9000 may include a skin contact layer 9100, which may include individual areas 9102 between slits 9101. Skin contact layer 9100 may be formed of foam, silicone, via overmolding, or using any material or process described for skin contact layers described above. The sensor layer 9400 may include a semiconductor layer (e.g. carbon film layer) 9410, a spacer or adhesive layer 9420, and a copper layer 9430, which may be applied directly to a flex PCB layer 9500. A connector tail 9550 may extend from the flex PCB layer 9500.

Figure 12B:
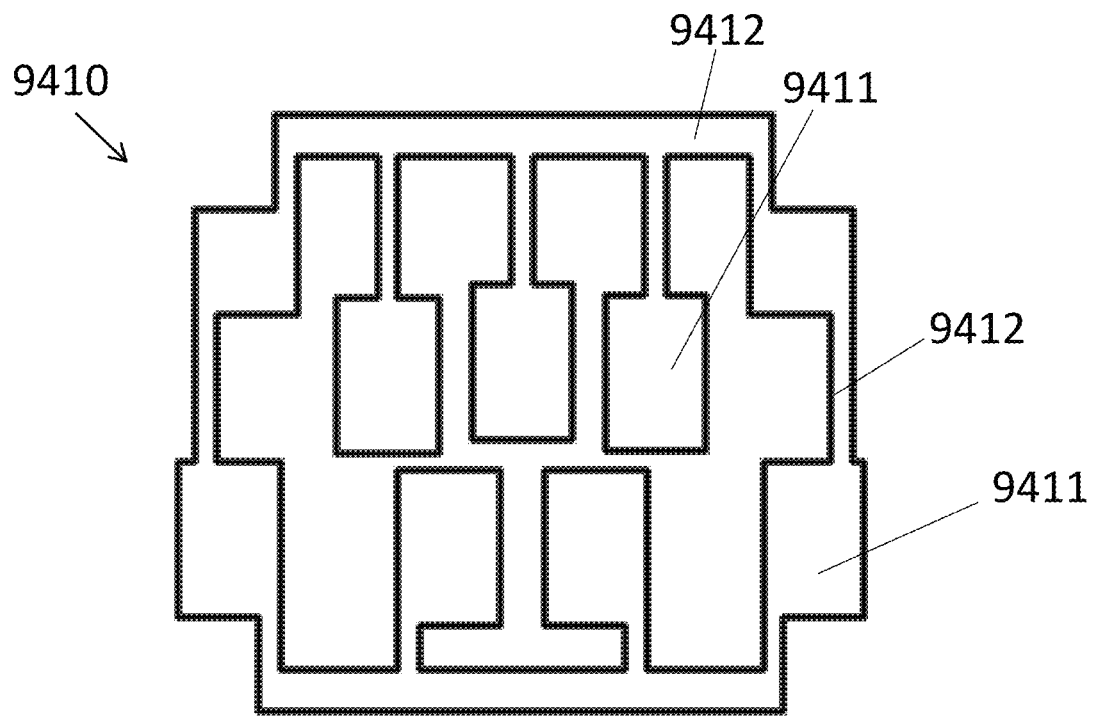
FIGS. 12B-C are plan views of components of the sensor array of FIG. 11A.
Figure 12C:
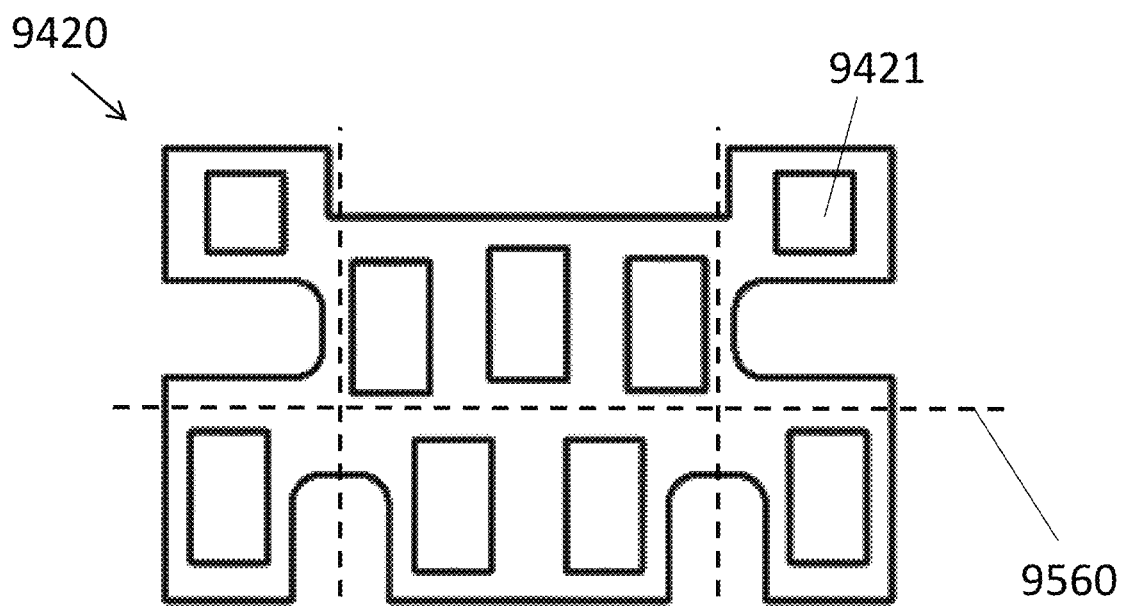

Semiconductor layer 9410 is shown in a plan view in FIG. 12B, and may include a plurality of FSR pads 9411 coupled by bridge connectors 9412, and the bridge connectors 9412 may be cut adjacent the FSR pads 9411 after assembly with the adhesive layer 9420. FIG. 12C illustrates a plan view of adhesive layer 9420, which may include a plurality of cutouts 9421 that may generally correspond to the locations of the individual FSR sensors. Sensor array 9000 may include nine sensors. FIG. 12C illustrates three exemplary trim lines 9560 that may be used to trim one or more sensors from the sensor array 9000 without losing functionality of the remaining sensors. However, it should be understood that these trim lines 9560 are only exemplary, and nearly any combination of trim lines may be followed to cut away unwanted sensors, although the at least one sensor must of course remain for the sensor array 9000 to provide sensing functionality.

Figure 13A:
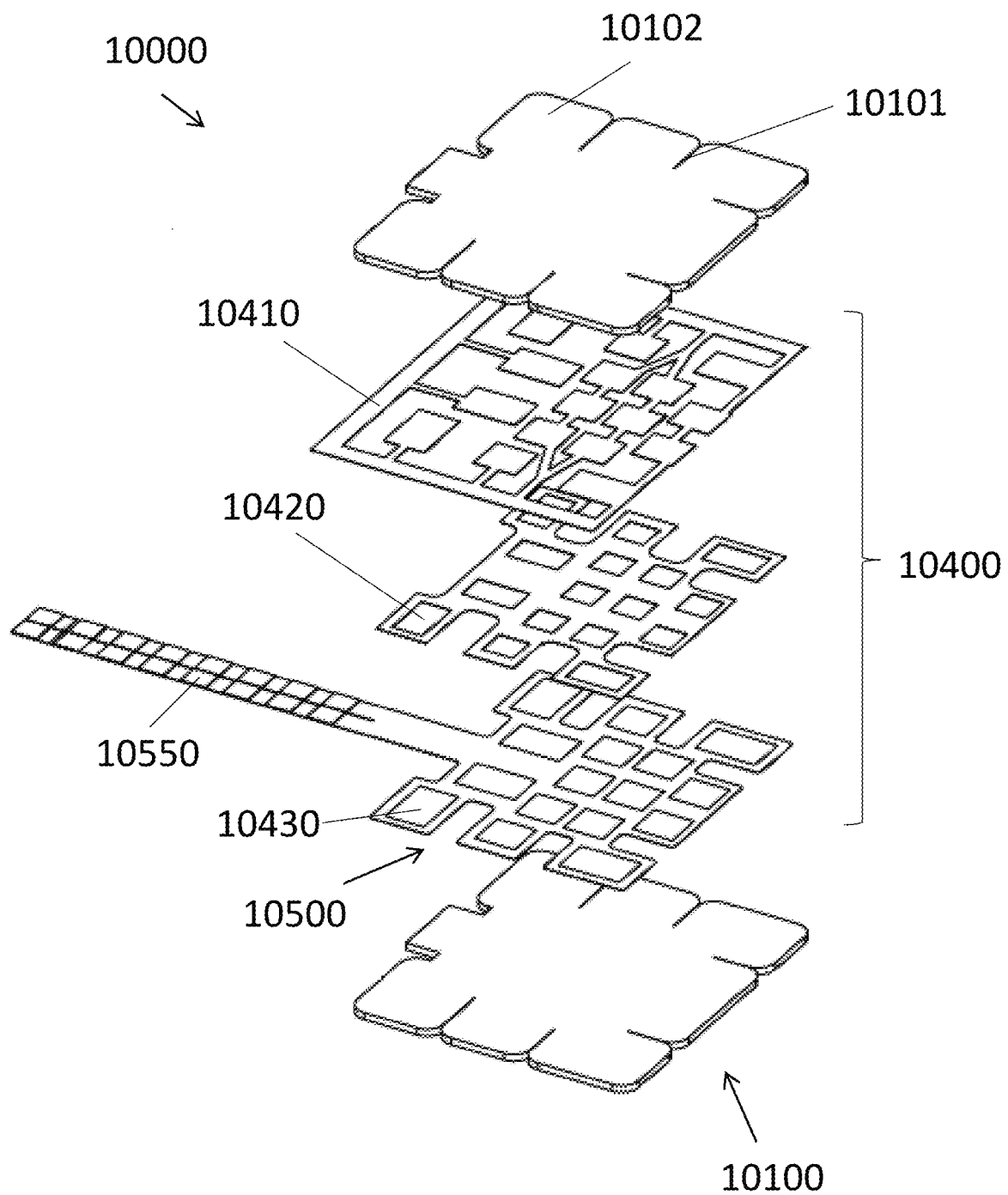
FIG. 13A is an exploded view of a sensor array according to yet a further embodiment of the disclosure.

FIG. 13A is an exploded view of another sensor array 10000 that is substantially identical to sensor arrays 5000-9000, with the main exception being the number of sensors and the shape of the sensor array. For example, sensor array 10000 may include a skin contact layer 10100, which may include individual areas 10102 between slits 10101. Skin contact layer 10100 may be formed of foam, silicone, via overmolding, or using any material or process described for skin contact layers described above. The sensor layer 10400 may include a semiconductor layer (e.g. carbon film layer) 10410, a spacer or adhesive layer 10420, and a copper layer 10430, which may be applied directly to a flex PCB layer 10500. A connector tail 10550 (which may be formed as a pair of connector tails 10550 due to the large number of sensors on the sensor array 10000) may extend from the flex PCB layer 10500.

Figure 13B:
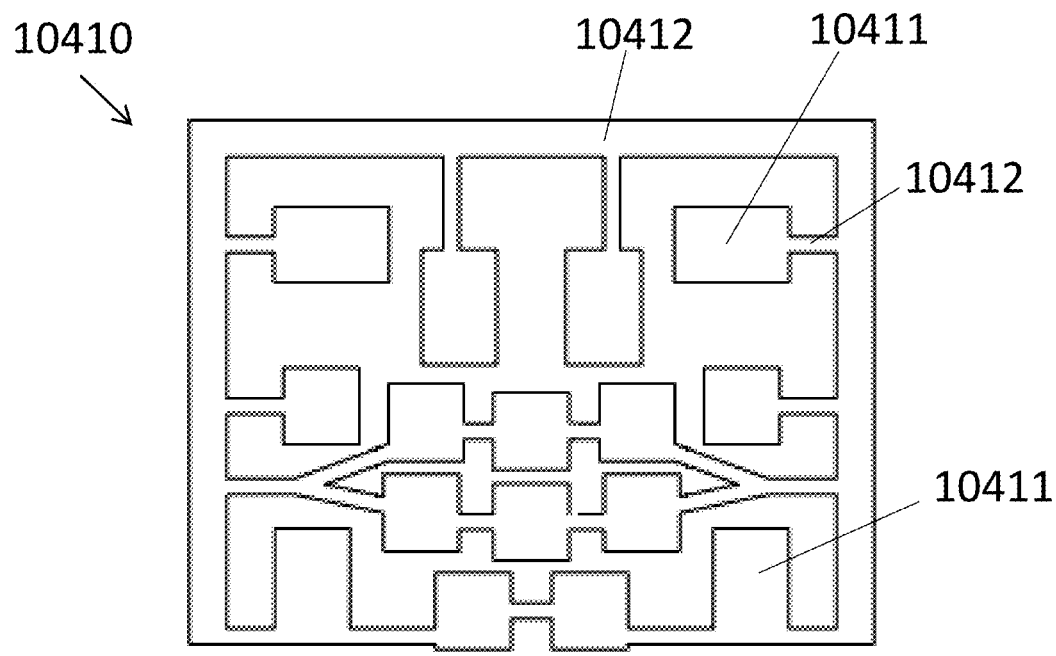
FIGS. 13B-C are plan views of components of the sensor array of FIG. 13A.
Figure 13C:
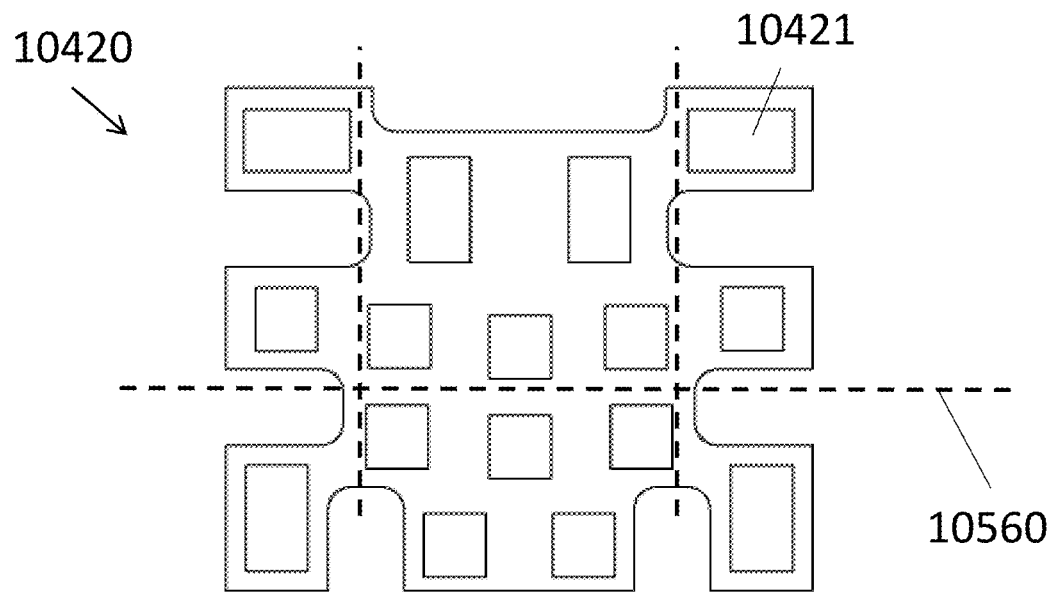

Semiconductor layer 10410 is shown in a plan view in FIG. 13B, and may include a plurality of FSR pads 10411 coupled by bridge connectors 10412, and the bridge connectors 10412 may be cut adjacent the FSR pads 10411 after assembly with the adhesive layer 10420. FIG. 13C illustrates a plan view of adhesive layer 10420, which may include a plurality of cutouts 10421 that may generally correspond to the locations of the individual FSR sensors. Sensor array 10000 may include sixteen sensors. FIG. 13C illustrates three exemplary trim lines 10560 that may be used to trim one or more sensors from the sensor array 10000 without losing functionality of the remaining sensors. However, it should be understood that these trim lines 10560 are only exemplary, and nearly any combination of trim lines may be followed to cut away unwanted sensors, although the at least one sensor must of course remain for the sensor array 10000 to provide sensing functionality.

As described above, any of the sensor arrays described herein (including the "patch" style sensor arrays) may be used with contact members similar to those described in connection with sensor array 2000, or without those contact sensors. The relative flexibility of the sensor arrays, as well as the large surface area contact between the sensor arrays and the user's body, may mitigate the need for such contact members. Even if the omission of contact members initially reduces the efficiency of signal transfer from the user's body through the sensors of the sensor array, such reduction may be compensated for via machine learning. For example, after any of the sensor arrays described above are positioned in or on a device that will contact a user's body, machine learning may be implemented to determine where along the sensor array contact with the user is strong or weak, and that information may be used to compensate for the fact that contact in certain areas is weak. The machine learning may be used to identify small patterns that occur when certain muscles contract, and those identified patterns may be utilized to better control the prosthesis. The sensors may also directly control the prosthesis.

Figure 14A:
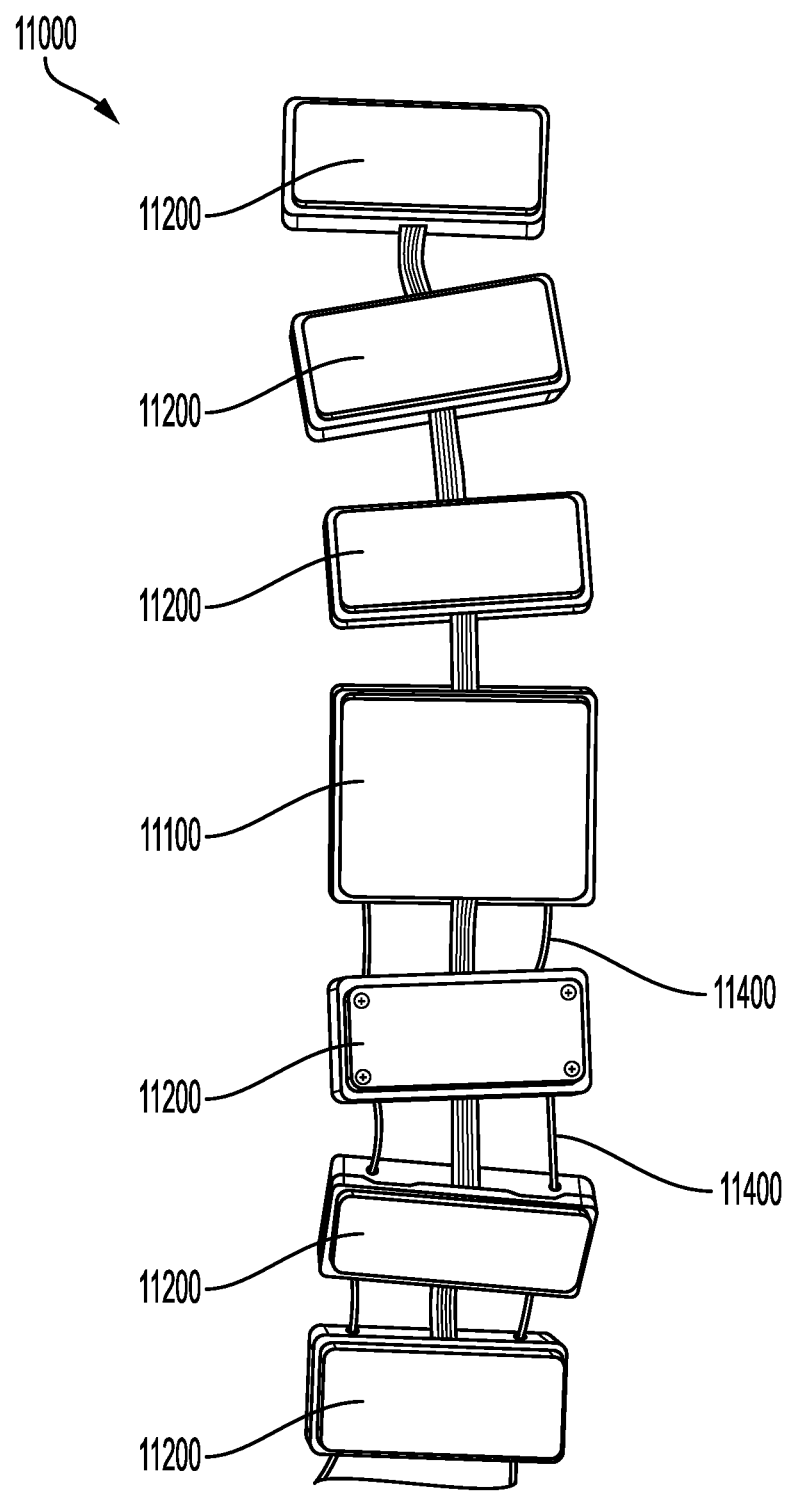
FIGS. 14A-C are various views of an armband sensor device including a plurality of sensors therein.
Figure 14B:
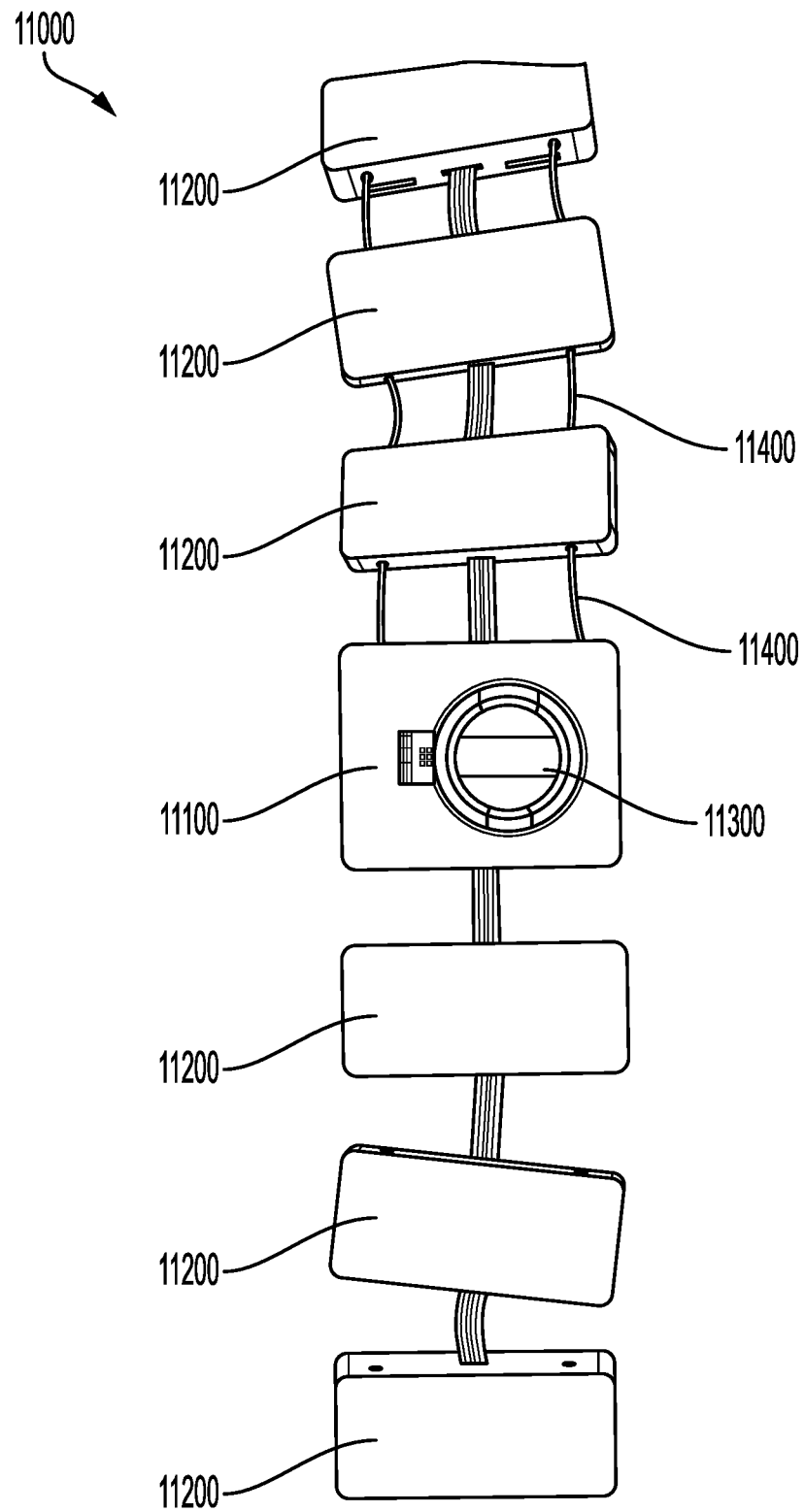
Figure 14C:
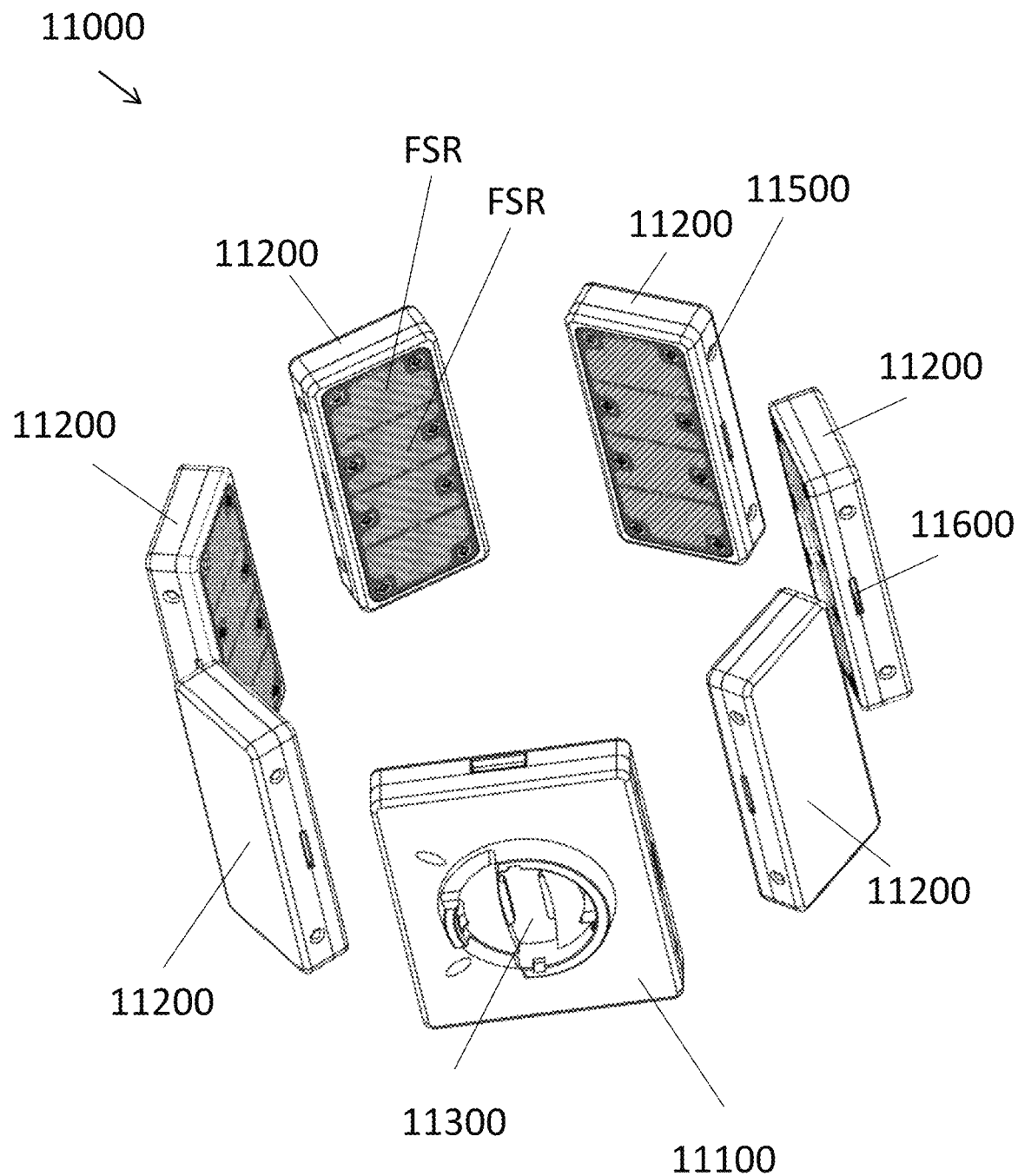

The specific examples of sensor arrays described above have been generally described in the context of an application for a socket to control a prosthetic extremity (e.g. arm, leg, hand, or foot), even though it has been made clear that the applications of the sensor arrays are not so limited. However, FIGS. 14A-C illustrate views of an armband sensor device 11000 that may be used, for example, to track muscle activity for purposes of augmented or virtual reality applications (e.g. including gaming), or for fitness tracking purposes. In the illustrated example, armband sensor device 11000 includes an electronics board within a first housing 11100. The electronics board in the first housing 11100 may include the bulk of (or all of) the non-sensor electronics, such as batteries, MCUs, ICs, etc. The armband sensor device 11000 may include a plurality of additional housings 11200. In the illustrated embodiment, the armband sensor device 11000 includes six additional housings 11200, with each housing being or including a plurality of FSR sensor arrays, for example three or four FSR sensors similar to sensor array 7000 (four FSRs illustrated in each housing 11200 in FIG. 14C). Each additional housing 11200, and the sensors provided therein, may be electrically connected (e.g. via one or more connector tails) to the electronics board in the first housing 11100, where the processing of sensor data may be performed. Because armband sensor device 11000 is intended to be used as an armband (e.g. wrapping around a forearm, upper arm, or as a leg band wrapping around an upper or lower leg), there may be slightly less constraints on the form factor, at least compared to a sensor array that must fit within a prosthetic socket. Thus, the first housing 11100 and additional housings 11200 may be formed with harder shells/housings (although it should be understood that armband sensor device 11000 may just as readily be formed from softer and more flexible materials like those described above) to provide additional robustness to the system. In use, a user may put his arm through the armband sensor 11000, for example when the armband sensor 11000 is in a circular configuration as shown in FIG. 14C. The user may then tighten the armband sensor 11000, if necessary, to ensure good contact between the user's arm and the sensor arrays that are within/on the additional housings 11200. In one example, in addition to the housings 11100 and 11200 being electrically coupled via tail connectors, additional laces or wires may connect the housings, with the wire being able to be tensioned to pull the housings into contact with the user's arm. For example, a ratcheting mechanism 11300 may be coupled to an outer surface of the first housing 11100, and the ratcheting mechanism may be coupled to one or more laces 11400. The one or more laces 11400 may be coupled to each housing 11100 and 11200, so that when the user's arm is within the armband sensor 11000, rotating the ratcheting mechanism 11300 pulls the one or more laces 11400 into the ratcheting mechanism, in turn pulling the sensor arrays in/on the additional housings 11200 into closer contact with the user's arm. FIG. 14C illustrates that each housing 11200 may include one or more apertures 11500 through which the wires/laces may be passed, as well as a center aperture 11600 for a connector tail or other electric connector to pass through. In the illustrated example, particularly if the sensors are FSRs, it may be desirable to include contact members similar to those described in connection with sensor array 2000, or otherwise providing the sensors with raised contact surfaces, since a more rigid sensor housing may generally (but need not always) correspond to less effective contact between the sensors and the user, particularly when a flat surface is in contact with a contoured body part.

The sensor arrays disclosed above have been described mainly in the context of FSRs. However, it should be clear that various other sensors besides, or in addition to, FSRs may be used with the described sensor arrays. For example, one or more of the FSRs in any of the sensor arrays described above may be swapped out or otherwise replaced with EMG sensors, temperature sensors, optical sensors, acoustic sensors, accelerometers, pressure sensors, microphones, capacitive sensors, surface tension sensors, moisture sensors, ultrasonic or ultrasound sensors, Hall Effect sensors, and the like. Still further, one or more of the sensors in the sensor array may be swapped out or otherwise replaced with other useful devices, such as haptic feedback devices, vibration devices, piezoelectric devices, ultrasonic devices, and/or electrode (or other shock-delivering) devices, to provide feedback to the user of the sensor array. For example, sensor array 4000 could be used as a bracelet type of device by wrapping the sensor array around a user's wrist for tracking fitness activities. While it may be desirable to include one or more FSRs as sensors, it may also be desirable to include accelerometers to track movement of the hand/wrist, temperature sensors to track increase in body temperature during fitness activities, moisture sensors for determining levels of sweat, and a haptic vibration device to provide the user with certain cues or other information (e.g. vibrating to confirm a threshold level of movement has been achieved).

Thus, despite the sensor arrays described herein being generally described in the context of FSRs for controlling prosthetic extremity devices, the various other applications of these sensor arrays (with or without modifications) should be clear. Wearable devices such as wristbands or watches have already been described, as well as the use of these sensor arrays to track movement and other information for use in augmented (or virtual) reality applications, such as in gaming. However, there are many other applications of these sensor arrays and the concepts described herein. The sensor arrays may interface with a human to control any other devices suitable to electronic control, including for example musical instruments with electronic controls. The sensor arrays described herein could be made in any suitable size as well. For example, large arrays of the sensor arrays described herein could be provided in or on clothing. In one particular example, elastic or other form fitting clothing, including athletic wear, could be provided with a large number of sensors (via a single large array, or more than one arrays of any desired size) in order to track athletic activity, muscle recovery, etc. And similar in concept, these sensor arrays could be provided in wrist bands, arm bands, chest straps, etc. to provide the desired effect. Further, the sensor arrays could be provided on or in pillows (or pillow coverings) in order to provide information to the user regarding sleep tracking, such as sleep quantity, quality, etc.

FSRs may be provided with different functional modes, including those known as "Shunt Mode" and "Thru Mode." Generally, a Shunt Mode FSRs are configured with a top semiconductor layer (e.g. carbon ink) and a bottom conductive layer of conductive (e.g. copper or silver) traces, and the conductive traces may be arranged into two sets of interdigitating fingers, although other particular designs may be suitable. When the top semiconductor layer is pressed into or toward the copper traces, the top layer shunts the traces, allowing current to pass. Typically, Shunt Mode FSRs are more receptive to a wider range of forces than Thru Mode FSRs. Thru Mode FSRs, on the other hand, are typically configured with two layers of conducive pads, with a carbon ink printed on top of the conductive pads. With this configuration, when the top layer is pressed into the bottom layer, current passes from the carbon layer to the copper layer on the opposite side, with more pressure resulting in more current passing through the connection. Thru Mode FSRs may typically work better with lighter forces and produce more linear outputs than Shunt Mode FSRs. Typically, when large arrays of FSRs are used, the FSRs are Thru Mode FSRs. However, the FSRs described above are generally configured as Shunt Mode FSRs, despite Shunt Mode FSRs typically being provided as single sensors. The Shunt Mode FSRs described herein may provide very high resolution and data, which may be even further tuned with software, and thus the arrays of Shunt Mode FSRs may provide significant benefits over the Thru Mode FSRs that are typically used when FSR arrays are called for.

Finally, it should be understood that components and features of embodiments described herein may be omitted from or added to other embodiments. For example, the contact members of earlier embodiments may be added to later embodiments, or omitted from the earlier embodiments. Also, the ability to trim sensors and/or the provision of actual indicia regarding where the trimming may be performed may be added or omitted from any of the embodiments described above. And while many or most embodiments described above include Shunt Mode FSR arrays, the embodiments may instead be provided with Thru Mode FSR arrays, and as should be clear from the description, the FSR sensors may be swapped out or otherwise replaced with other sensors and/or feedback mechanisms of interest, as described herein.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A sensor array system comprising:
a skin contact layer;
a flexible printed circuit board ("PCB") positioned adjacent the skin contact layer, the flexible PCB having a connector tail; and
a plurality of force sensing resistors ("FSRs"), each FSR being positioned on the flexible PCB, the connector tail adapted to electrically connect the plurality of FSRs to a signal receiving component;
wherein the flexible PCB is configured so that when one or more of the plurality of FSRs are trimmed away from the flexible PCB the connector tail is still adapted to electrically connect a remaining one or more of the plurality of FSRs to the signal receiving component, wherein the skin contact layer includes a plurality of slits extending inward from an outer edge thereof, so that a plurality of individual areas are formed between adjacent ones of the plurality of slits.

2. The sensor array system of claim 1, further comprising a plurality of indicia on at least one of the skin contact layer and the flexible PCB, the plurality of indicia indicative of pathways along which the flexible PCB is configured to be cut to remove the one or more of the plurality of FSRs from the flexible PCB so that the connector tail is still adapted to electrically connect the remaining one or more of the plurality of FSRs to the signal receiving component.

3. The sensor array system of claim 1, wherein the skin contact layer is formed with a generally rectangular shape.

4. The sensor array system of claim 1, wherein each individual area of the skin contact layer corresponds with a location of at least one of the plurality of FSRs.

5. The sensor array system of claim 1, wherein each of the plurality of slits aligns with a corresponding cutout in the flexible PCB.

6. The sensor array system of claim 1, wherein the plurality of FSRs are provided as shunt mode FSRs.

7. A prosthetic device comprising:
a socket for receiving a residual limb of a user, the socket having a plurality of panels configured to directly or indirectly contact the residual limb of the user; and
a plurality of the sensor array systems of claim 1, each of the plurality of sensor array systems of claim 1 coupled to a surface of a corresponding one of the plurality of panels.

8. The prosthetic device of claim 7, wherein the socket includes a distal linking portion configured to couple to a prosthetic limb.

9. The prosthetic device of claim 8, wherein the distal linking portion includes a recess therein, the signal receiving component being positioned within the recess.

10. The prosthetic device of claim 9, wherein the connector tail of each one of the plurality of sensor array systems of claim 1 pass through an opening in the distal linking portion of the socket and connects to the signal receiving component positioned within the recess.

11. A prosthetic device comprising:
a socket for receiving a residual limb of a user, the socket having a plurality of panels configured to directly or indirectly contact the residual limb of the user, the socket includes a distal linking portion configured to couple to a prosthetic limb, the distal linking portion includes a recess therein, a signal receiving component being positioned within the recess; and
a plurality of sensor array systems, each of the plurality of sensor array systems coupled to a surface of a corresponding one of the plurality of panels, each sensor array system comprising:
a skin contact layer;
a flexible printed circuit board ("PCB") positioned adjacent the skin contact layer, the flexible PCB having a connector tail; and
a plurality of force sensing resistors ("FSRs"), each FSR being positioned on the flexible PCB, the connector tail adapted to electrically connect the plurality of FSRs to the signal receiving component;
wherein the flexible PCB is configured so that when one or more of the plurality of FSRs are trimmed away from the flexible PCB the connector tail is still adapted to electrically connect a remaining one or more of the plurality of FSRs to the signal receiving component.

* * * * *